(12) United States Patent
Liu et al.

(10) Patent No.: US 8,592,649 B2
(45) Date of Patent: Nov. 26, 2013

(54) FUNCTIONAL EXPRESSION OF SHUFFLED YEAST NITRATE TRANSPORTER (YNT1) IN MAIZE TO IMPROVE NITRATE UPTAKE UNDER LOW NITRATE ENVIRONMENT

(75) Inventors: Lu Liu, Palo Alto, CA (US); Hoa Giang, Oakland, CA (US); Dale F. Loussaert, Clive, IA (US); Haiyin Wang, Johnston, IA (US)

(73) Assignee: Pioneer Hi Bred International Inc, Johnston, IA (US)

( * ) Notice: Subject to any disclaimer, the term of this patent is extended or adjusted under 35 U.S.C. 154(b) by 384 days.

(21) Appl. No.: 12/860,265

(22) Filed: Aug. 20, 2010

(65) Prior Publication Data

US 2011/0047647 A1    Feb. 24, 2011

Related U.S. Application Data

(60) Provisional application No. 61/235,601, filed on Aug. 20, 2009.

(51) Int. Cl.
*A01H 5/00* (2006.01)
*C12N 15/82* (2006.01)
*C12N 5/04* (2006.01)
*C07H 21/04* (2006.01)

(52) U.S. Cl.
USPC .......... 800/298; 800/278; 800/306; 800/312; 800/320; 435/419; 536/23.74

(58) Field of Classification Search
None
See application file for complete search history.

(56) References Cited

U.S. PATENT DOCUMENTS

2007/0124833 A1 * 5/2007 Abad et al. .................. 800/278
2009/0183270 A1   7/2009 Adams et al.

FOREIGN PATENT DOCUMENTS

| WO | WO 03/066847 A2 | 8/2003 |
| WO | WO 2007/022195 A2 | 2/2007 |
| WO | WO 2008/157375 A1 | 12/2008 |
| WO | WO 2009/009142 A2 | 1/2009 |

OTHER PUBLICATIONS

Woolfit et al 2007 Eukaryotic Cell, April: p. 721-733.*
Frasier et al 2000 Plant Journal 23:4 p. 489-496.*
McAllister et al 2012 Plant Biotechnology Journal p. 1-15.*
Bassham and Raikhel 2000 Plant Physiology 122: p. 999-1001.*

* cited by examiner

*Primary Examiner* — Brent T Page
*Assistant Examiner* — Matthew Keogh
(74) *Attorney, Agent, or Firm* — Pioneer Hi-Bred Int'l Inc.

(57) ABSTRACT

The present invention provides methods and compositions relating to altering NT activity, nitrogen utilization efficiency and/or uptake in plants. The invention relates to a method for the production of plants with maintained or increased yield under low nitrogen fertility. The invention provides isolated nitrate transporter variant (NT variant) nucleic acids and their encoded proteins. The invention further provides recombinant expression cassettes, host cells, and transgenic plants. Plants transformed with nucleotide sequences encoding the NT variant enzyme show improved properties, for example, increased yield.

10 Claims, 16 Drawing Sheets

```
                    1351                                                      1400
      YNT1   (1351) GCAATGGGTAACTTAGGAGGCATTTTGTTTAGTTTAGTGTTCAGGTACAC
 YNT1 R2AL   (1351) GCAATGGGTAACTTAGGAGGCATTTTGTTTAGTTTAGTGTTCAGGTACAC
 YNT1 R2C7   (1351) GCAATGGGTAACTTAGGAGGCATTTTGTTTAGTTTAGTGTTCAGGTACAC
 YNT1 R3FS   (1351) GCAATGGGTAACTTAGGAGGCATTTTGTTTAGTTTAGTGTTCAGGTACAC
 YNT1 R3LS   (1351) GCAATGGGTAACTTAGGAGGCATTTTGTTTAGTTTAGTGTTCAGGTACAC
                    1401                                                      1450
      YNT1   (1401) TATATCAAATCGAGTGAACAACTACTTCAAGCCGTTTTGGATTATAGGAA
 YNT1 R2AL   (1401) TATATCAAATGGAGTGAACAACTACTTCAAGGCGTTTTGGATTATAGGAA
 YNT1 R2C7   (1401) TATATCAAATGGAGTGAACAACTACTTCAAGGCGTTTTGGATTATAGGAA
 YNT1 R3FS   (1401) TATATCAAATGGAGTGAACAACTACTTCAAGGCGTTTTGGATTATAGGAA
 YNT1 R3LS   (1401) TATATCAAATGGAGTGAACAACTACTTCAAGGCGTTTTGGATTATAGGAA
                    1451                                                      1500
      YNT1   (1451) TTGTTTGCACTGCTGTAAATCTGGTCTGTGTGCTTATTCCAATTAGAGAG
 YNT1 R2AL   (1451) TTGTTTGCACTGCTGTAAATCTGGTCTGTGTGCTTATTCCAATTAGAGAG
 YNT1 R2C7   (1451) TTGTTTGCACTGCTGTAAACCTGGTCTGTGTGCTTGTTCCAATTAGAGAG
 YNT1 R3FS   (1451) TTGTTTGCACTGCTGTAACACTGGTCTGTGTCCTTGTTCCAATTAGAGAG
 YNT1 R3LS   (1451) TTGTTTGCACTGCTGTAAACCTGGTCTGTGTGCTTGTTCCAATTAGAGAG
                    1501           1527
      YNT1   (1501) GAGAGGCCAAGGAAAGCGGAAAATTGA
 YNT1 R2AL   (1501) GAGAGGCCAAGGAAAGCGGAAAATTGA
 YNT1 R2C7   (1501) GAGAGGCCACATAAAGCGGAAAATTGA
 YNT1 R3FS   (1501) GAGAGGCCAAGGAAAGCGGAAAATTGA
 YNT1 R3LS   (1501) GAGAGGCCAAGGAAAGCGGAAAATTGA
```

FIG. 1D

```
              1                                                  50
    YNT1   (1) MQLSTLWEPPIVNPRNLKATSIPTFNLWNVYGRNFFFGWFGPFVCFLSWF
YNT1 R2AL  (1) MQLSTLWEPPIVNPRNLKATSIPTFNLWNVYGRNFFFGWFGPFVAFLSWF
YNT1 R3FS  (1) MQLSTLWEPPIVNPRNLKATSIPTFNLWNVYGRNFFFGWFGPFVAFLSWF
YNT1 R2C7  (1) MQLSTLWEPTIVNPRNLKATSIPTFNLWNVYGRNFFFGWFGPFVAFLSWF
YNT1 R3LS  (1) MQLSTLWEPTIVNPRNLKATSIPTFNLWNVYGRNFFFGWFGPFVAFLSWF
              51                                                 100
    YNT1  (51) AFPPLLHGMLKKDLRLTAVDISNNNICGLTGTLLGRFILGPLNDKYGPRI
YNT1 R2AL (51) AFPPLLHGMLKKDLRLTAVDISNNNICGLTGTLLGRFILGPLNDKYGPRI
YNT1 R3FS (51) AFPPLLHGMLKKDLRLTAVDISNNNICGLTGTLLGRFILGPLNDKYGPRI
YNT1 R2C7 (51) AFPPLLHGMLKKDLRLTAVDISNNNICGLTGTLLGRFILGPLNDKYGPRI
YNT1 R3LS (51) AFPPLLHGMLKKDLRLTAVDISNNNICGLTGTLLGRFILGPLNDKYGPRI
              101                                                150
    YNT1 (101) TLTGVLVAGAIPTAFVPLVTNVAGLHAIRFFISFLGSSFICCSQFCAVFF
YNT1 R2AL (101) TLAGVLVAGAIPTAFVPLVTNVAGLHAIRFSISFLGSSFICCSQFCAVFF
YNT1 R3FS (101) TLAGVLVAGAIPTAFVPLVTNVAGLHAIRFIGFLGSSFICCSQFCAVFF
YNT1 R2C7 (101) TLTGVLVAGAIPTAFVPLVTNVAGLHAIRFFSFLGSSFICCSQFCAVFF
YNT1 R3LS (101) CLTGVLVAGAIPTAFVPLVTNVAGLHAIRFFISFLGSSFICCSQFCAVFF
              151                                                200
    YNT1 (151) DNNIIGTANAISAGWGNAGGGVAFFVMPAISNALENRGYSLHHSWSYSFV
YNT1 R2AL (151) DNNIVGTANAVSAGWGNAGGGVAFFVMPAISNALENRGYSLHHSWSYSFV
YNT1 R3FS (151) DNNIMGTANALSAGWGNAGGGVAFFVMPAISNALENRGYSLHHSWSYSFV
YNT1 R2C7 (151) DNNIMGTANALSAGWGNAGGGVAFFVMPAISNALENRGYSLHHSWSYSFV
YNT1 R3LS (151) DNNIVGTANAVSAGWGNAGGGVAFFVMPAISNALENRGYSLHHSWSYSFV
              201                                                250
    YNT1 (201) IGPFLILMITAILIFVFGSDCPRGRWSLRGDILGINMDNMLVKSVSVTRH
YNT1 R2AL (201) IGPFLILMITAILTFVFGSDCPRGRWSLRGDTLGINMDNMLVKSVSITRF
YNT1 R3FS (201) IGPFLILMITAILTFVFGSDCPRGRWSLRGDTLGINMDNMLVKSVSITRH
YNT1 R2C7 (201) IGPFLILMITAILISVFGSDCPRGRWSLRGDTLGINMDNMLVKSVSITRH
YNT1 R3LS (201) IGPFLILMITAILTFVFGSDCPRGRWSLRGDTLGINMDNMLVKSVSITRH
              251                                                300
    YNT1 (251) FSKEGELTSVFVEPVNAIDKVVVEPNQDQEILEVADILNGDEIIEDPSLN
YNT1 R2AL (251) FPKEGELTSVFVEPVNAIDKAVSEPNQDQEILEVADILNGDEIIEDPSLN
YNT1 R3FS (251) FSKEGELTSVFVEPVNAIDKAVSEPNQDQEILEVADILNGDEIIEDPSLN
YNT1 R2C7 (251) FSKEGELTSEFGEPVNAIDKTVVEPNQDQEILEVADILNGDEIIEDPSLN
YNT1 R3LS (251) FSKEGELTSEFAEPVNAIDKNVVEPNQDQEILEVADILNGDEIIEDPSPN
              301                                                350
    YNT1 (301) DVVKICLSPRTMLVGLCYMCSFGTELAVESIISNLFGQKMTNWSTSKAGA
YNT1 R2AL (301) DVVKILLSPRTMLVGLCYMCSFGTELAVESIISNLFGQKMTSWSTSKAGA
YNT1 R3FS (301) DVVKILLSPRTMLVGLCYMCSFGTELAVESIISNLFGQKMTNWSTSKAGA
YNT1 R2C7 (301) DVVKICLSPRTMLVGLCYMCSFGTELAIESIISNLFGQKMTNWSTSKAGA
YNT1 R3LS (301) DVVKICLSPRTMLVGLCYMCSFGTELAVESIISNLFGQKMTNWSTSKAGA
              351                                                400
    YNT1 (351) WGSMLGLLNVVARPAGGIISDELYQRFKITKAKKFWMLFTGLMQGIFLIW
YNT1 R2AL (351) WGSMLGLLNVVARPAGGIISDELYQRFKITKAKKFWMLFTGLMQGIFLIW
YNT1 R3FS (351) WGSMLGLLNVVARPAGGIISDELYQRFKIVKAKKFWMLFTGLMQGIFLIW
YNT1 R2C7 (351) WGSMLGLLNVVARPAGGIISDELYQRFKIVKAKKFWMLFTGLMQGIFLIW
YNT1 R3LS (351) WGSMLGLLNVVARPAGGIISDELYQKFKITKAKKFWMLFTGLMQGLFLIW
              401                                                450
    YNT1 (401) IGLVPELSIAGLIVSVSFLCLWFEYGNGANYACVPVVNRHFSGIVSSVTC
YNT1 R2AL (401) IGLVPELSIAGMIVSVSFLCLWFEMGNGANYACVPVVNRHFSGIVSGVVC
YNT1 R3FS (401) IGLVPELSIAGLIVSVSFLALWFEMGNGANYACVPVVNRHFSGIVSGVVC
YNT1 R2C7 (401) IGLVPELSIAGLIVSVSFLALWFEMGNGANYACVPHVNRHFSGIVSGVVC
YNT1 R3LS (401) IGLVPELSIAGAIVSVSFLCLWFEMGNGANYACVPHVNRHFSGIVSGVVC
```

FIG. 2A

```
            451                                                500
      YNT1 (451) AMGNLGGILFSLVFRYTISNGVNNYFKAFWIIGIVCTAVNLVCVLIPIRE
 YNT1 R2AL (451) AMGNLGGILFSLVFRYTISNGVNNYFKAFWIIGIVCTAVNLVCVLIPIRE
 YNT1 R3FS (451) AMGNLGGILFSLVFRYTISNGVNNYFKAFWIIGIVCTAVTLVCVLIPIRE
 YNT1 R2C7 (451) AMGNLGGILFSLVFRYTISNGVNNYFKAFWIIGIVCTAVNLVCVLVPIRE
 YNT1 R3LS (451) AMGNLGGILFSLVFRYTISNGVNNYFKAFWIIGIVCTAVNLVCVLVPIRE
            501
      YNT1 (501) ERPRKAEN
 YNT1 R2AL (501) ERPRKAEN
 YNT1 R3FS (501) ERPRKAEN
 YNT1 R2C7 (501) ERPHKAEN
 YNT1 R3LS (501) ERPRKAEN
```

FUNCTIONAL EXPRESSION OF SHUFFLED YEAST NITRATE TRANSPORTER (YNT1) IN MAIZE TO IMPROVE NITRATE UPTAKE UNDER LOW NITRATE ENVIRONMENT

CROSS-REFERENCE TO RELATED APPLICATIONS

This utility application claims the benefit U.S. Provisional Application No. 61/235,601, filed Aug. 20, 2009, which is incorporated herein in its entirety by reference.

FIELD OF THE INVENTION

The field of the disclosure relates generally to molecular biology. In particular, the invention relates to methods and compositions for improving nitrogen utilization efficiency and/or nitrogen uptake in plants.

BACKGROUND OF THE INVENTION

Nitrate is the major nitrogen source for plants to uptake from soil. To meet the demands in the global supply of food, feed, fiber, and fuel, farmers tend to apply excessive nitrogen fertilizers to increase the grain yield of crops, such as maize. To avoid the pollution by nitrate and reduce the cost of farming, there is a need for plants, particularly maize, that is more efficient in nitrate uptake/utilization to maintain grain supplies and protect our environment.

Nitrate uptake from soil into the plant root cells is an active process which is against an electrochemical potential gradient of the plasma membranes. Once in the root cells, nitrate can be: 1) reduced to nitrite by the cytoplasmic enzyme nitrate reductase then ammonium by nitrite reductase in chloroplasts and then incorporate into amino acids; 2) taken up and stored in vacuole; 3) transported to the xylem for long-distance translocation into the leaves; and 4) exported out of root cells. All steps of nitrate movements are facilitated by nitrate transporters.

Nitrate transporters can be classified into two classes based on the affinity to nitrate, low- and high-affinity nitrate transporter systems. Low-affinity nitrate transporter systems (LATS) are responsible when the soil nitrate concentration is higher than 1 mM and high-affinity nitrate transporter systems (HATS) play a major role when the soil nitrate concentration is lower than 1 mM.

High-affinity nitrate transporter systems also can be classified into two groups based on if a nitrate transporter associated protein is required for nitrate transporter functionality. Single-component HATS contain a protein with typical carrier-type structure with 12 transmembrane domains and two-component HATS include an additional small associated protein with 2 transmembrance domains (Tong Y et al., *Plant J.*, (2005) 41:442-450). Single-component HATS involved in fungi and red algae and two-component HATS have been reported in green algae and plants.

The expression of plant nitrate transporters can be constitutive or induced by nitrate. Plant nitrate transporters act as component of nitrate responsive signaling pathway and regulation of root growth independent of nitrate uptake have be reported (Little et al., PNAS (2005) 102:13693-13698). It would be desirable to improve nitrogen use efficiency and nitrate uptake of plants; however, an attempt to improve nitrate uptake by over-expressing tobacco endogenous high affinity nitrate transporters failed. (Fraisier et al., *Plant J.*, (2000) 23:489-496).

BRIEF SUMMARY OF THE INVENTION

As described herein, variants of a nitrate transporter (NT) from yeast *Pichia angusta*, YNT1, have been shown to be involved in nitrogen uptake when expressed in vivo in *Arabidopsis* and maize plants as well as in in vitro assays. The present invention provides NT variant polynucleotides, codon optimized NT variant gene coding sequences, related variant polypeptides, and all conservatively modified variants of the present NT variant sequences.

In another aspect, the present invention relates to an NT variant polynucleotide that has been substituted with one or more of the substitutions shown below in Table 3, a polynucleotide encoding a polypeptide comprising an amino acid sequence that has been substituted with one or more of the substitutions shown in Table 2, a polynucleotide that encodes any of the polypeptides of SEQ ID NOS:4, 6, 8 and 10; a polynucleotide having any of the sequences of SEQ ID NOS: 3, 5, 7, 9 and 11; a polynucleotide having at least 30 nucleotides in length which hybridizes under stringent conditions to any of the former polynucleotides. In another aspect, the present invention includes a polynucleotide having at least 80% sequence identity to any of the sequences of SEQ ID NOS: 3, 5, 7, 9 and 11. Provided herein in another aspect of the invention are isolated polynucleotides degenerate as a result of the genetic code for any of the NT variants of the present invention. In another aspect, an isolated polynucleotide is complementary to a polynucleotide of any one of the NT variants of the present invention. In another aspect, the present invention relates to an isolated polynucleotide that encodes an NT variant polypeptide that increases a plant's nitrogen utilization efficiency, yield or NT activity.

In yet another aspect, the present invention relates to a transgenic plant including a recombinant expression cassette of a promoter functional in a plant operably linked to any of the isolated polynucleotides of the present invention. The present invention also provides for transgenic seed from the transgenic plant. In another aspect, the present invention is directed to a host cell transfected with the recombinant expression cassette of a promoter functional in a plant operably linked to any of the isolated polynucleotides of the present invention.

In a further aspect, the present invention relates to an isolated NT variant polypeptide having NT activity. The NT variant polypeptide may have an amino acid sequence that has been substituted with at least one amino acid substitution shown in Table 2 below, an amino acid sequence having at least 80% sequence identity to any of the amino acid sequences set forth in SEQ ID NOS: 4, 6, 8 and 10; or a polypeptide encoded by any of the polynucleotides set forth in SEQ ID NOS: 3, 5, 7, 9 and 11. In yet another aspect, the present invention relates to a transgenic plant of a recombinant expression cassette comprising a promoter functional in a plant operably linked to an isolated polynucleotide encoding a polypeptide that has an amino acid sequence that has at least 80% sequence identity to any of the amino acid sequences set forth in SEQ ID NOS: 4, 6, 8 and 10 and has NT activity. The present invention also provides for transgenic seed from the transgenic plant. In another aspect, the present invention is directed to a host cell transfected with the recombinant expression cassette comprising a promoter functional in a plant operably linked to any of the isolated polynucleotides encoding polypeptides of the present invention.

In a further aspect, the present invention relates to a method of modulating the level of NT variant proteins in a plant cell. In one aspect, the method includes transforming a plant cell with an NT variant polynucleotide operably linked to a promoter. The polynucleotide may be in sense or antisense orientation. The method further includes expressing the polynucleotide for an amount of time sufficient to modulate the level of NT variant protein in the plant cell.

In another aspect, the present invention provides a method of modulating the activity of NT variant proteins in a plant. The method includes stably transforming a plant cell with an NT variant polynucleotide, in sense or antisense orientation, operably linked to a promoter functional in a plant cell. The method includes regenerating the transformed plant cell into a transformed plant that expresses the NT variant polynucleotide in an amount sufficient to modulate the activity of NT variant proteins in the plant.

In another aspect, the present invention relates to a method of increasing the yield of a plant or a plant's NUE or both. In one aspect, the method includes introducing into plant cells a construct comprising a polynucleotide encoding an NT variant of the present invention. The polynucleotide may be operably linked to a promoter functional in plant cells to yield transformed plant cells. The transformed plant cells are regenerated into a transgenic plant. The NT variant is expressed in the cells of the transgenic plant at levels sufficient to increase NT activity. In one aspect, the NT variant is expressed in the cells of the transgenic plant at levels sufficient to increase a plant's yield or NUE.

In another aspect, the present invention relates to polynucleotides encoding a *Porphyra perforata* nitrate reductase (PPNR), particularly polynucleotides encoding a PPNR in which the alanine at amino acid position 551 has been substituted with glycine (A551G) and a PPNR in which the alanine at amino acid position 551 has been substituted with glycine and the serine at amino acid position 561 has been substituted with aspartic acid (A551G S561D)). Such NR polynucleotides include, but are not limited to, codon optimized polynucleotides such as, for example, a maize codon optimized polynucleotide encoding PPNR A551G S561D, which is referred to herein as PPNR A551G S561D MO. The NR polynucleotides of the invention can be used to transform a plant by itself or stacked with one or more NT variant polynucleotides of the invention and used in methods to improve NUE, nitrate uptake, nitrogen assimilation, root biomass, or combinations thereof in a plant.

The present invention also provides for expression cassettes comprising at least one NT variant polynucleotide or NR polynucleotide of the present invention. In another aspect, the present invention is directed to a host cell transfected with the recombinant expression cassette comprising a promoter functional in a plant operably linked to any of the isolated polynucleotides encoding polypeptides of the present invention. Also provided are transformed plants, plant parts, plant cells, and seeds comprising at least one expression cassette of the present invention.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The invention can be more fully understood from the following detailed description and the accompanying drawing and Sequence Listing which form a part of this application.

Figure 1A:
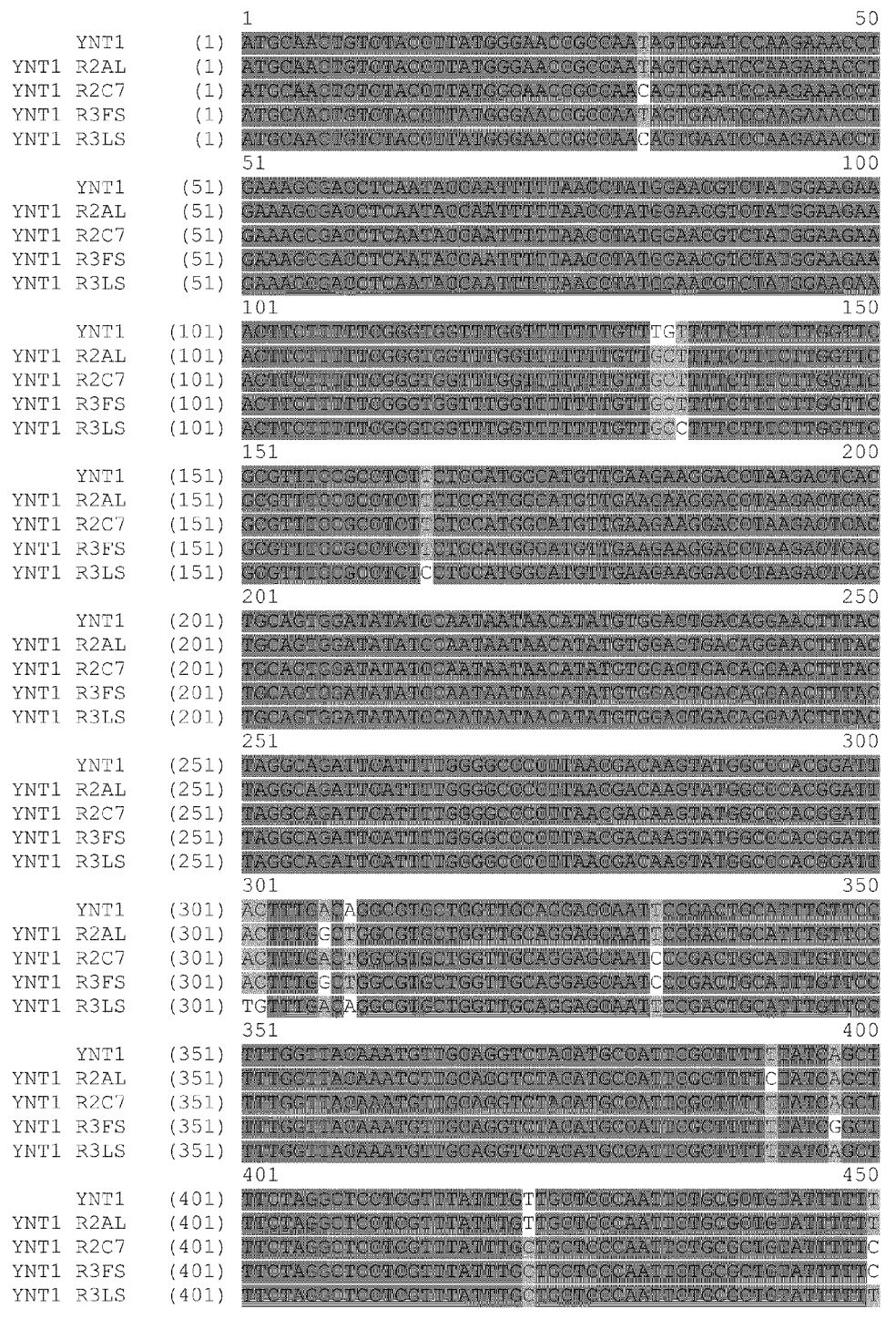
Figure 1B:
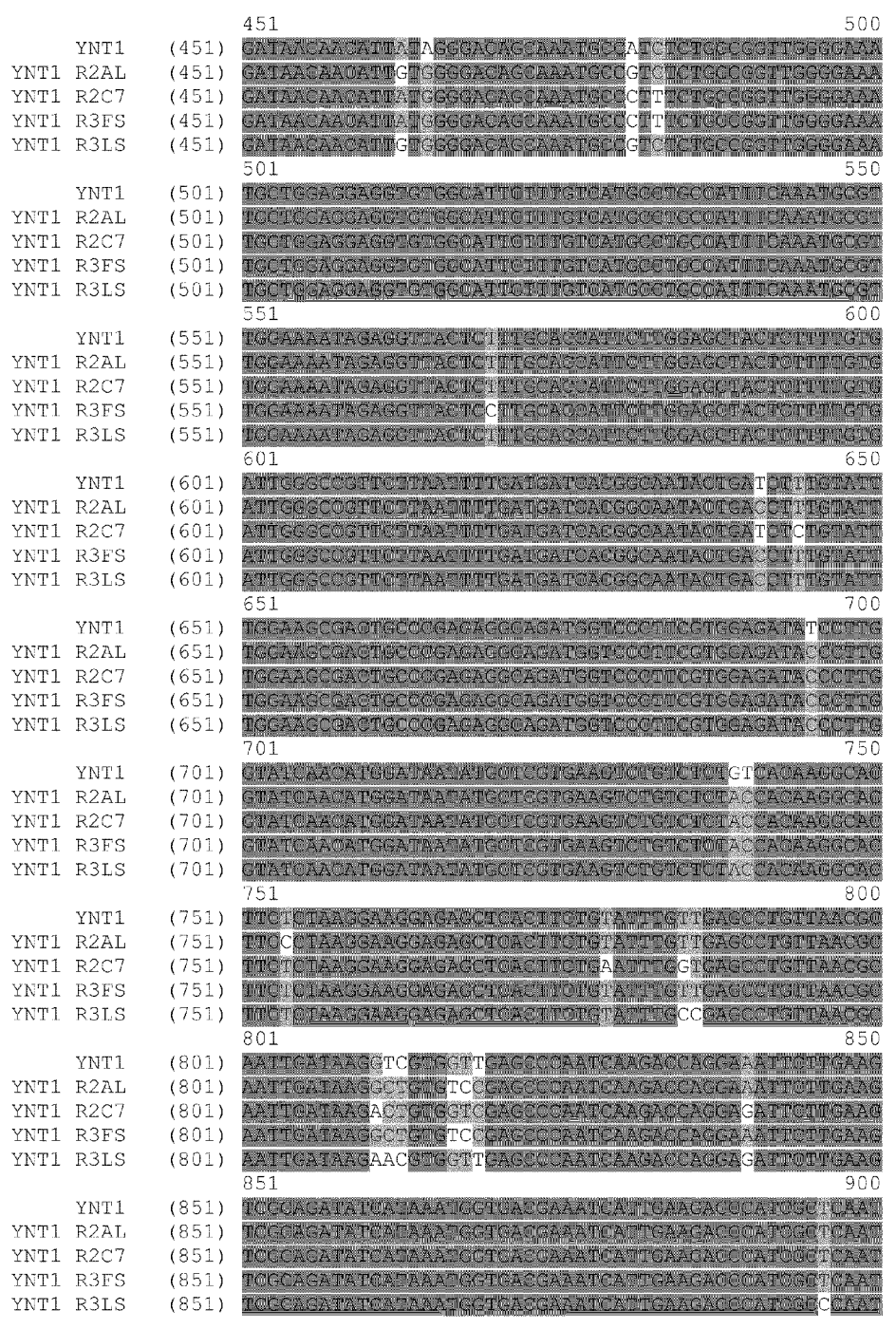
Figure 1C:
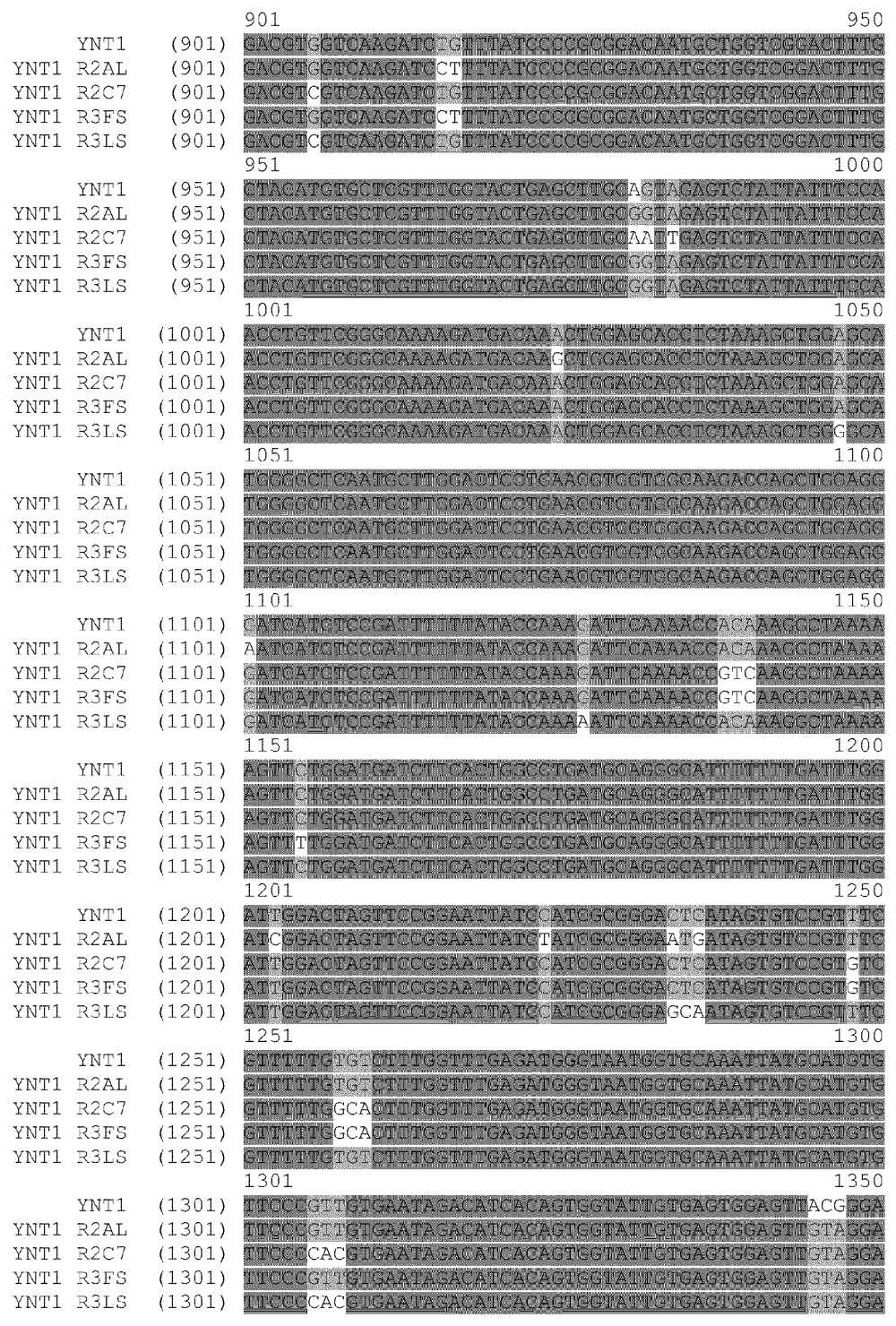

FIGS. 1A-1D show a nucleotide sequence comparison of YNT1 ORF and variants. YNT1 corresponds to SEQ ID NO: 1, YNT1 R2AL corresponds to SEQ ID NO: 3, YNT1 R2C7 corresponds to SEQ ID NO: 5, YNT1 R3FS corresponds to SEQ ID NO: 7, and YNT1 R3LS corresponds to SEQ ID NO: 11.

FIGS. 2A-2B show an amino acid sequence comparison among YNT1 and variants. YNT1 corresponds to SEQ ID NO: 2, YNT1 R2AL corresponds to SEQ ID NO: 4, YNT1 R3FS corresponds to SEQ ID NO: 8, YNT1 R2C7 corresponds to SEQ ID NO: 6, and YNT1 R3LS corresponds to SEQ ID NO: 10.

Figure 6A:
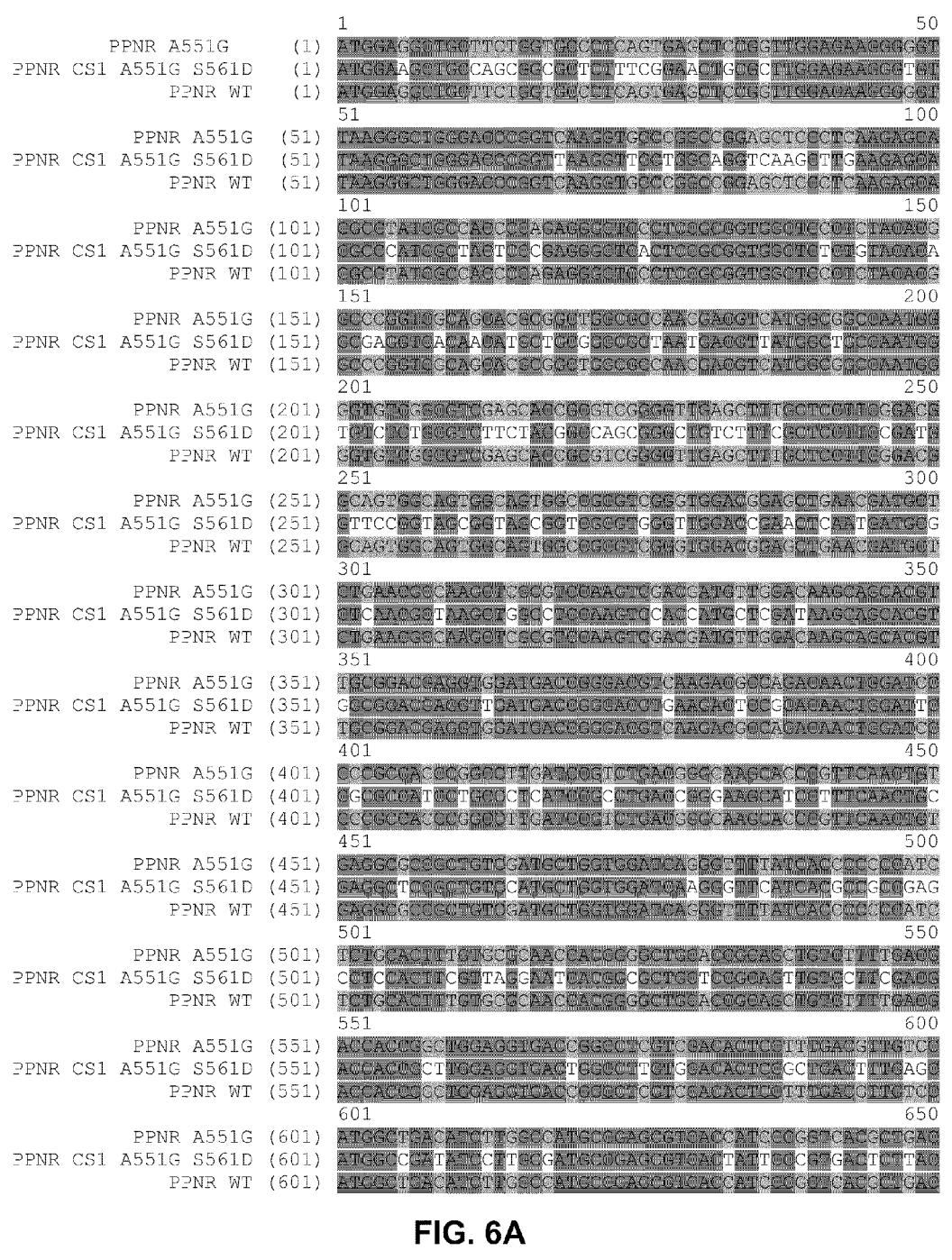
Figure 6B:
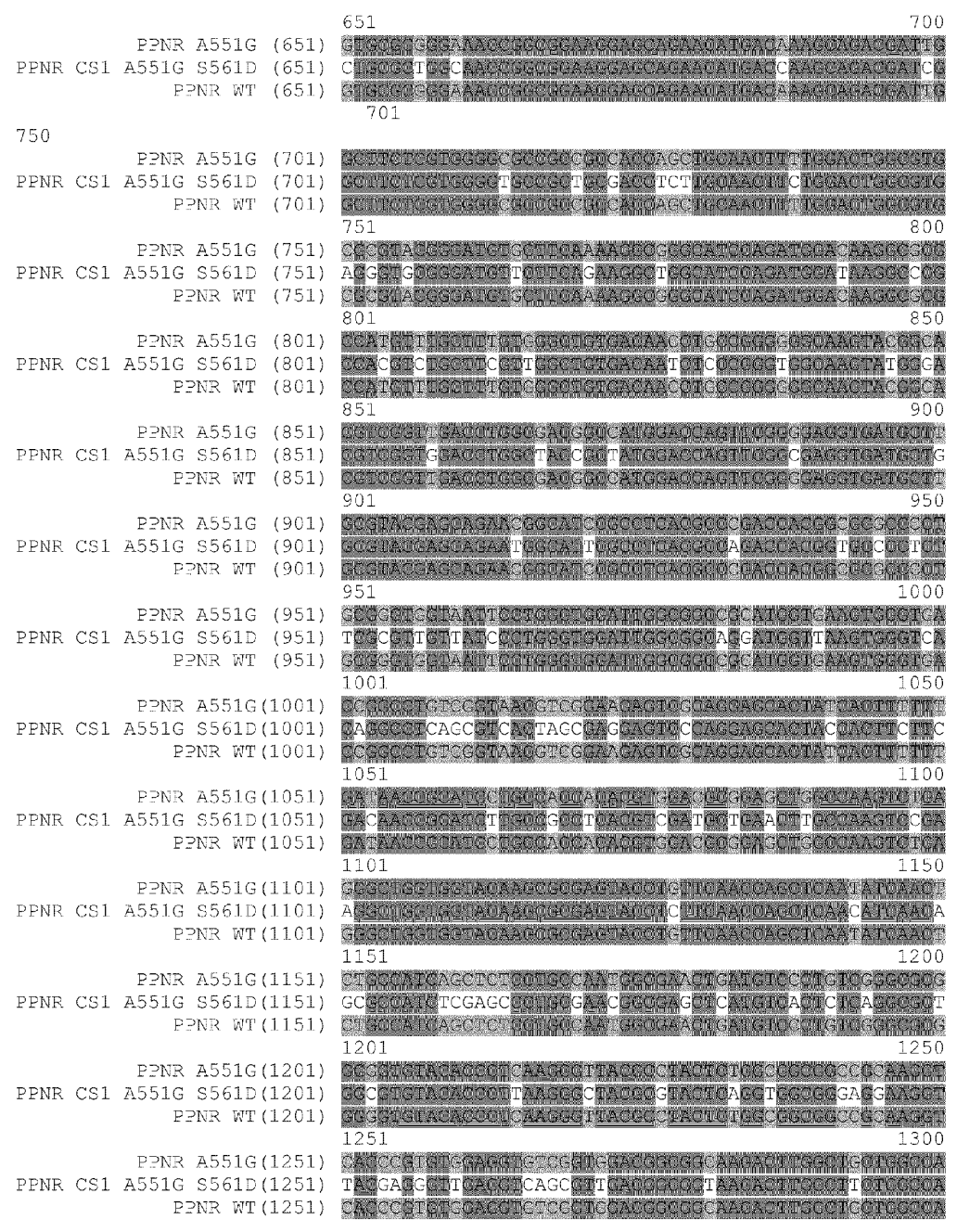
Figure 6C:
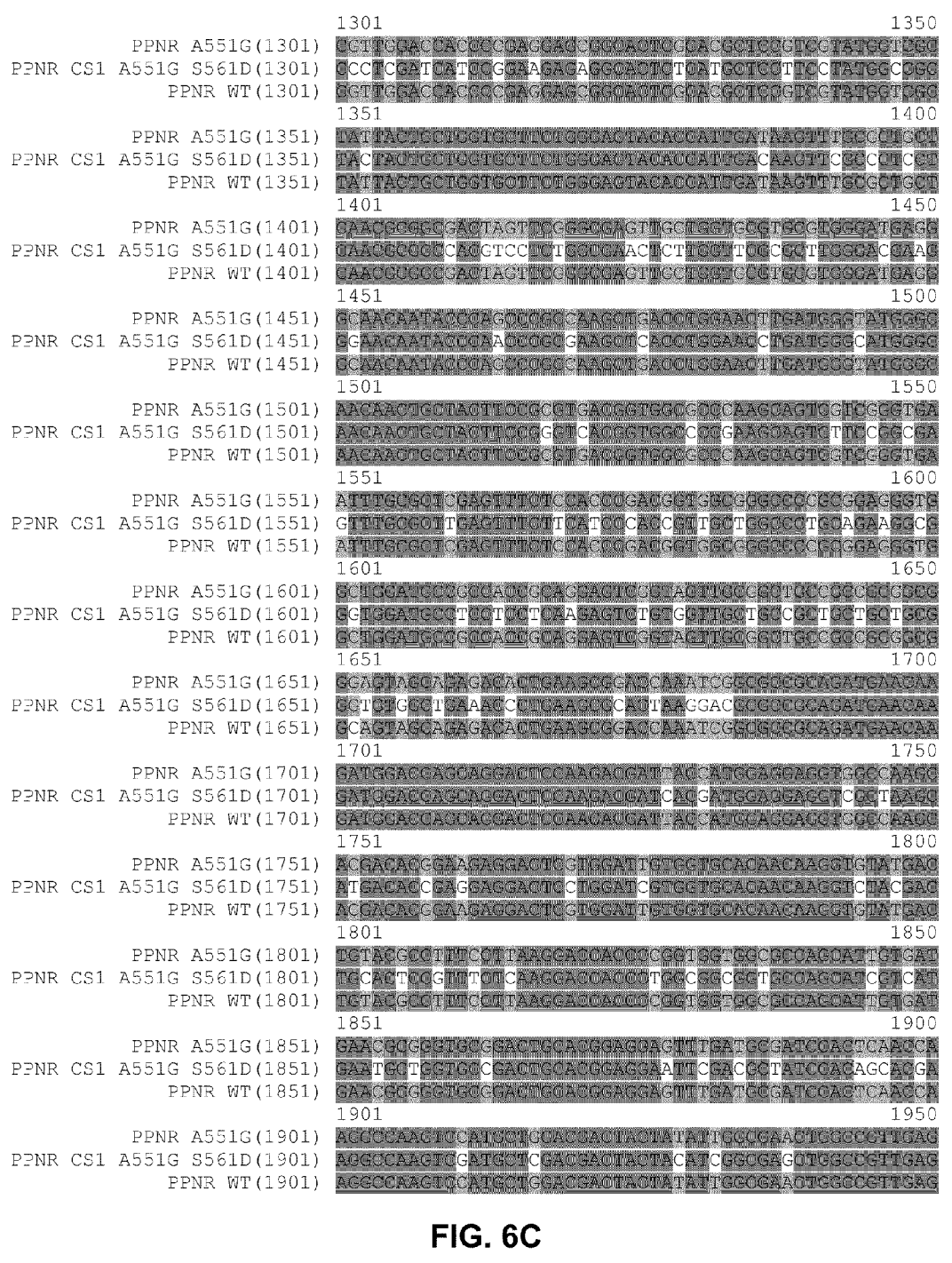
Figure 6D:
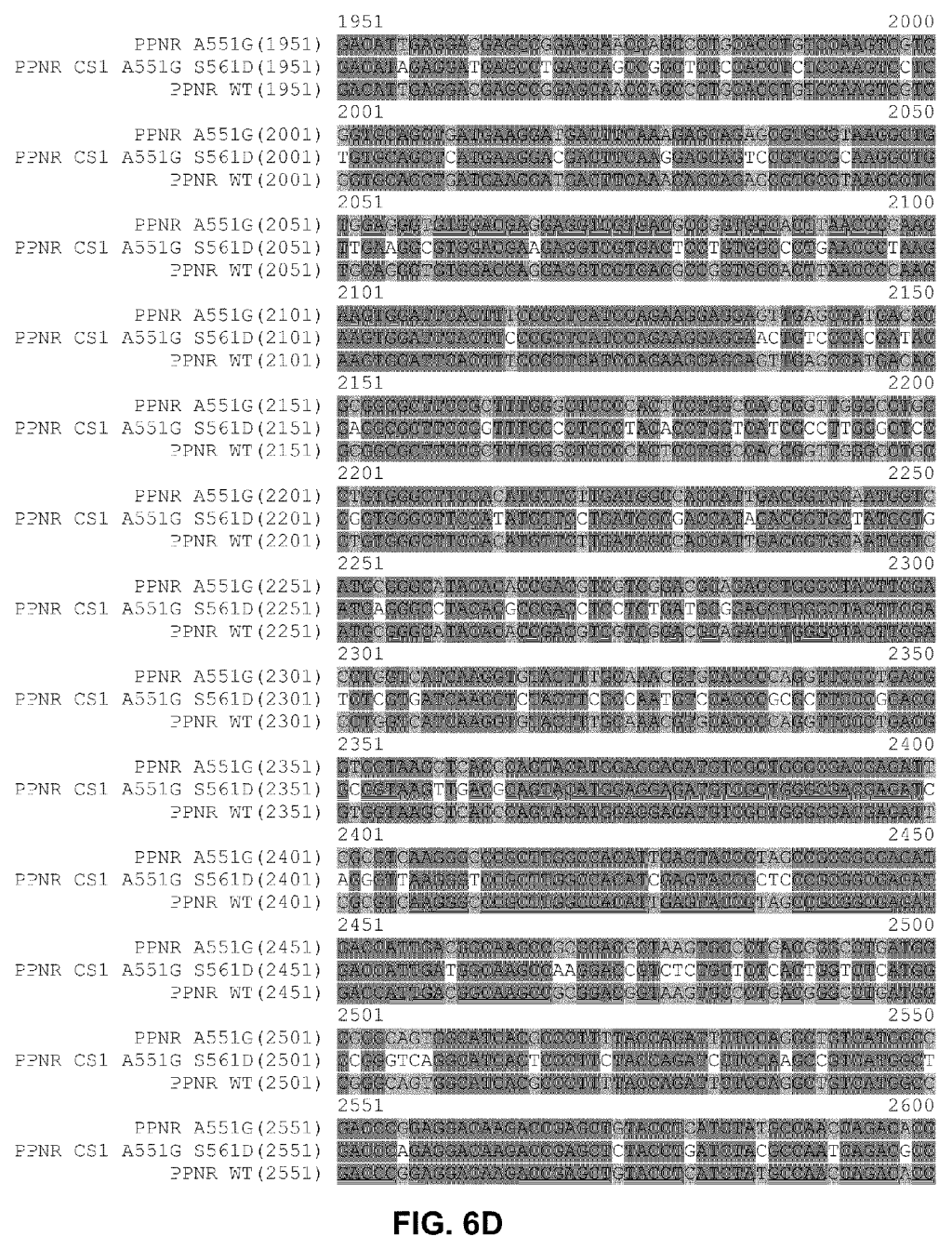
Figure 6E:
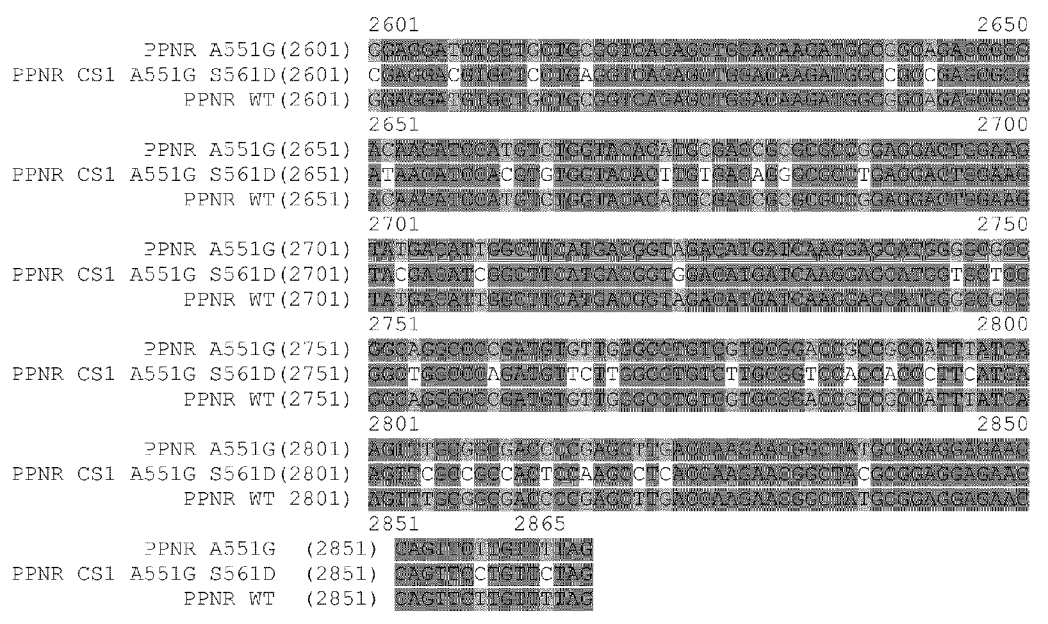

FIGS. 6A-6E show a DNA sequence comparison of wild type *Porphyra perforata* nitrate reductase (PPNR) ORF (SEQ ID NO:13), *Porphyra perforata* nitrate reductase (PPNR) A551G ORF (SEQ ID NO:12), and *Porphyra perforata* nitrate reductase (PPNR) A551G S561D MO ORF (SEQ ID NO:16).

FIGS. 7A-7B show an amino acid sequence comparison of wild type *Porphyra perforata* nitrate reductase (PPNR) (SEQ ID NO:15), *Porphyra perforata* nitrate reductase (PPNR) A551G (SEQ ID NO:14), and *Porphyra perforata* nitrate reductase (PPNR) A551G S561D MO (SEQ ID NO:17).

BRIEF DESCRIPTION OF THE SEQUENCES

Figure 3:
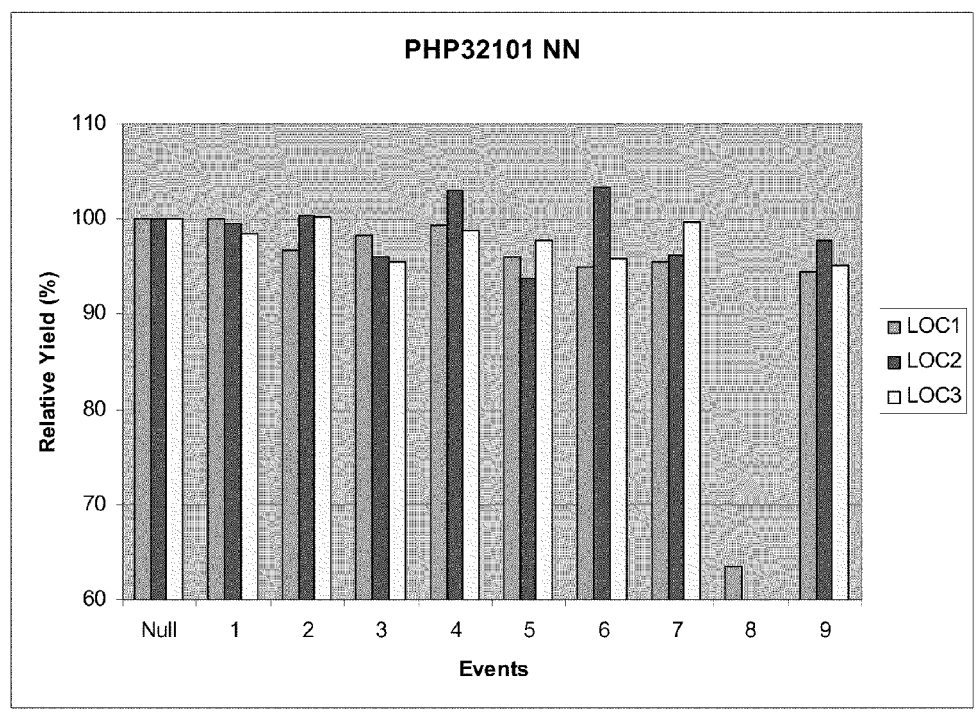
FIG. 3 is a graphical representation of the results of field yield trials of maize transgenic plants containing ZM-RM2:ADHI Intron:YNT1R3FS (PHP32101) at 3 locations under normal nitrogen (NN) conditions. Eight events were tested at 3 locations and event 8 was only tested at 1 location. The relative yield (%) to the null is presented here.

The application provides details of NT sequences and NT variants and others as shown in Tables 1-3 below.

TABLE 1

Details of NT, NR, NT variant and NR variant sequences.

| SEQ ID NO: | Polynucleotide/ polypeptide | Length | Identification |
| --- | --- | --- | --- |
| 1 | Polynucleotide | 1527 | ORF of YNT1 wild type cDNA |
| 3 | Polynucleotide | 1527 | ORF of YNT1R2AL |
| 5 | Polynucleotide | 1527 | ORF of YNT1R2C7 |
| 7 | Polynucleotide | 1527 | ORF of YNT1R3FS |
| 9 | Polynucleotide | 1527 | ORF of YNT1R3FS MO with maize preferred codon |
| 11 | Polynucleotide | 1527 | ORF of YNT1R3LS |
| 2 | polypeptide | 508 | YNT1 wild type |
| 4 | polypeptide | 508 | YNT1R2AL |
| 6 | polypeptide | 508 | YNT1R2C7 |
| 8 | polypeptide | 508 | YNT1R3FS |
| 10 | polypeptide | 508 | YNT1R3LS |
| 12 | Polynucleotide | 2865 | PPNR A551G ORF |
| 13 | Polynucleotide | 2865 | wild type PPNR ORF |
| 14 | polypeptide | 954 | PPNR A551G |
| 15 | polypeptide | 954 | wild type PPNR |
| 16 | polynucleotide | 2865 | PPNR A551G S561D MO ORF |
| 17 | polypeptide | 954 | PPNR A551G S561D MO |

TABLE 2

Amino acid substitutions in NT variants.
(Numbering is relative to NT YNT1 wild type sequence, SEQ ID NO: 2)

| SEQ ID NO. | Name | Length | Identification and position of amino acid substitution in NT variant relative to SEQ ID NO: 2 |
|---|---|---|---|
| 4 | YNT1R2AL | 508 | C45A, T103A, F131S, I155V, I161V, I214T, I232T, V247T, S252P, V271A, V273S, C306L, N342S, L412M, T449V |
| 6 | YNT1R2C7 | 508 | I11T, C45A, I155M, I161L, F215S, I232T, V247T, V260E, V262G, V271T, V328I, T380V, C420A, V436H, T449V, I496V, R504H |
| 8 | YNT1R3FS | 508 | C45A, T103A, S133G, I155M, I161L, I214T, I232T, V247T, V271A, V273S, C306L, T380V, C420A, T449V, N490T |
| 10 | YNT1R3LS | 508 | I11T, C45A, T101C, I155V, I161V, I214T, I232T, V247T, V262A, V271N, L299P, R376K, L412A, V436H, T449V, I496V |

TABLE 3

Nucleotide substitutions in NT variants.
(Numbering is relative to NT YNT1 wild type sequence, SEQ ID NO: 1).

| SEQ ID NO. | Name | Length | Identification and position of nucleotide substitution in NT variant relative to SEQ ID NO: 1 |
|---|---|---|---|
| 3 | YNT1R2AL | 1527 | t133g, g134c, a307g, a309t, t392c, a463g, a465g, a481g, t641c, t695c, g739a, t740c, t754c, t812c, c813t, g817t, t818c, t819c, t916c, g917t, a981g, a1025g, g1101a, t1203c, c1224t, c1234a, c1236g, a1345g, c1346t, g1347a |
| 5 | YNT1R2C7 | 1527 | t32c, t133g, g134c, a309t, t333c, t423c, t450c, a465g, a481c, c483t, t644c, t695c, g739a, t740c, t779a, t785g, g811a, t812c, c813t, t819c, a840g, g906c, g982a, a984t, a1138g, c1139t, a1140c, t1248g, t1258g, g1259c, t1260a, g1306c, t1307a, t1308c, a1345g, c1346t, g1347a, t1470c, a1486g, a1510c, g1511a, g1512t |
| 7 | YNT1R3FS | 1527 | t133g, g134c, a307g, a309t, t333c, a397g, t423c, t450c, a465g, a481c, c483t, t570c, t641c, t695c, g739a, t740c, t812c, c813t, g817t, t818c, t819c, t916c, g917t, a981g, a1138g, c1139t, a1140c, c1155t, t1248g, t1258g, g1259c, t1260a, a1345g, c1346t, g1347a, a1469c, t1470a |
| 9 | YNT1R3FS MO with maize preferred codon | 1527 | a6g, c7t, t16c, a18c, a24g, g27a, a30g, a33c, t39c, a42g, a43c, a45g, g51c, a54g, g57c, t61a, c62g, a63c, a66c, a69g, t72c, t75c, a81c, c90g, t93c, a96c, a97c, a99g, t108c, g114c, t120c, t123c, t126c, t129c, t132g, t133g, g134c, t135c, t138c, t141c, t142a, c143g, t144c, g153t, t156c, g159t, t162g, t165c, c168g, c174t, t178c, g180c, a192c, a193c, a195c, c196t, c198g, a204c, t210c, a213c, t214a, c215g, t219c, t222c, a228c, c231c, a234c, g237c, a240c, a243t, t247c, a249c, a252c, c255t, a256c, a258c, t265c, g267c, g270c, c273a, t276c, c279t, t288c, a294g, g297c, t300c, t303c, t304c, g306c, a307g, c312t, g315t, g318c, t321c, a324c, a327t, a320c, t333c, a342t, t345c, t351g, t352c, g354t, t357g, a360c, t363c, t366c, a369c, t372c, c373t, a375g, t384c, t387g, t390c, t393c, a397g, t402c, a405c, t409a, c410g, t412a, c413g, g414c, t417c, t420c, t423c, t427a, c428g, a432g, t441a, a444g, t447c, t450c, t453c, a462c, a465g, g468c, a471c, a474c, t477c, a481c, c483g, c489t, t492c, a498c, t504c, a507t, a510c, a519c, t525c, c528t, t534g, t540c, t541a, c542g, a543c, g549c, t550c, g552c, a555g, t558g, a559c, a561c, t564c, c567t, t568a, c569g, t570c, t571c, g573c, t579c, t580a, c581g, t582c, t592a, c593g, t594c, t597c, t603c, g606c, t613c, a615c, t618c, t619c, g621c, g630c, a633c, t636c, c637t, t641c, t645c, a648g, t651c, a654c, c663t, g666a, a673c, a675c, t679a, c680g, t684c, t687c, a690c, t693c, t695c, t699c, t702c, t714c, t717c, t730a, c731c, t732c, c735g, t736a, t737c, t738c, g739a, t740c, a744c, g747a, t754c, c755g, t756c, t762g, a765c, t775a, c776g, t777c, a780g, t783c, t786g, t792g, t795g, a801c, t804c, t807c, t812c, c813t, g816t, g817a, t818g, t819c, c825g, a831g, a840g, t843c, t846c, a849g, c852g, a855c, t858c, a864c, t867c, t870c, a876g, t882c, a885g, a891g, t892a, c893g, g894c, t900c, c909t, t916c, g917t, t918c, t919c, a921c, t922a, c923g, g927t, g930c, a933c, g939c, c942g, a945c, t948c, t961a, c962g, g963c, t966c, t969c, t972c, t978c, a981t, a984t, t993c, t996c, t997a, c998g, g1005c, g1011c, a1014g, a1023c, c1026t, t1036a, c1037g, t1038c, a1041g, a1047t, a1050c, t1057a, c1058g, a1059t, t1065c, a1068t, c1069t, c1071g, g1074c, a1086c, a1092t, a1098c, |

TABLE 3-continued

Nucleotide substitutions in NT variants.
(Numbering is relative to NT YNT1 wild type sequence, SEQ ID NO: 1).

| SEQ ID NO. | Name | Length | Identification and position of nucleotide substitution in NT variant relative to SEQ ID NO: 1 |
|---|---|---|---|
| 11 | YNT1R3LS | 1527 | g1101t, c1107t, t1108a, c1109g, t1113c, t1116c, t1117c, a1119c, a1125g, a1126c, a1128c, a1134g, a1138g, c1139t, a1140g, t1146c, a1149g, t1170c, g1176c, g1182a, t1188c, t1191c, t1192c, g1194c, t1197c, a1206c, a1209c, g1215a, a1218g, t1219c, a1221c, t1222a, c1223g, g1230c, a1233t, a1239c, g1242t, t1243a, c1244g, t1248g, t1249a, c1250g, g1251c, t1254c, t1255c, g1257c, t1258g, g1259c, t1260c, t1263c, t1269c, t1281c, t1284c, a1287c, t1290c, t1293c, a1296c, t1299c, t1302g, c1305a, t1308g, a1215c, a1317c, c1323t, t1326c, t1329c, t1332c, a1336t, g1337c, a1341c, a1345g, c1346t, a1350t, a1353t, t1359c, c1362t, t1263c, a1365c, a1368c, t1375c, g1377c, t1380c, t1383c, t1384c, a1386c, a1393c, g1395c, t1401c, a1404c, t1405a, c1406g, a1407c t1410c, a1413c, g1434c, t1437c, t1443c, a1446c, a1449c, t1452c, t1455c, c1458t, t1461c, t1464c, a1467g, a1469c, t1470c, g1473c, c1483t, t1485g, t1488c, a1491g, t1494c, a1495c, a1497g, a1504c, g1506c, a1510c, g1512c, a1515g, g1518t, a1521g, t1524c, g1526a, a1527g t32c, t133g, g134c, t135c, t165c, a301t, c302g, t423c, a463g, a465g, a481g, t641c, t695c, g739a, t740c, t785c, t786c, g811a, t812a, a840g, t896c, g906c, a981g, a1047g, g1127a, c1234g, t1235c, c1236a, g1306c, t1307a, t1308c, a1345g, c1346t, g1347a, t1470c, a1486g |

DETAILED DESCRIPTION OF THE INVENTION

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting. The following is presented by way of illustration and is not intended to limit the scope of the invention.

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., Langenheim and Thimann, (1982) *Botany: Plant Biology and Its Relation to Human Affairs*, John Wiley; *Cell Culture and Somatic Cell Genetics of Plants*, vol. 1, Vasil, ed. (1984); Stanier, et al., (1986) *The Microbial World*, 5$^{th}$ ed., Prentice-Hall; Dhringra and Sinclair, (1985) *Basic Plant Pathology Methods*, CRC Press; Maniatis, et al., (1982) *Molecular Cloning: A Laboratory Manual; DNA Cloning*, vols. I and II, Glover, ed. (1985); *Oligonucleotide Synthesis*, Gait, ed. (1984); *Nucleic Acid Hybridization*, Hames and Higgins, eds. (1984); and the series *Methods in Enzymology*, Colowick and Kaplan, eds, Academic Press, Inc., San Diego, Calif.

Definitions

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

In describing the present invention, the following terms will be employed, and are intended to be defined as indicated below.

By "microbe" is meant any microorganism (including both eukaryotic and prokaryotic microorganisms), such as fungi, yeast, bacteria, actinomycetes, algae and protozoa, as well as other unicellular structures.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, Persing, et al., eds., American Society for Microbiology, Washington, D.C. (1993). The product of amplification is termed an amplicon.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is *Micrococcus rubens*, for which GTG is the methionine codon (Ishizuka, et al., (1993) *J. Gen. Microbiol.* 139:425-32) can be modified to yield a functionally identical molecule. Accordingly, each silent variation of a nucleic acid, which encodes a polypeptide of the present invention, is implicit in each described polypeptide sequence and incorporated herein by reference.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80% or 90%, preferably 60-90% of the native protein for it's native substrate. Conservative substitution tables providing functionally similar amino acids are well known in the art.

The following six groups each contain amino acids that are conservative substitutions for one another:
  1) Alanine (A), Serine (S), Threonine (T);
  2) Aspartic acid (D), Glutamic acid (E);
  3) Asparagine (N), Glutamine (Q);
  4) Arginine (R), Lysine (K);
  5) Isoleucine (I), Leucine (L), Methionine (M), Valine (V); and
  6) Phenylalanine (F), Tyrosine (Y), Tryptophan (W).
See also, Creighton, Proteins, W.H. Freeman and Co. (1984).

As used herein, "consisting essentially of" means the inclusion of additional sequences to an object polynucleotide where the additional sequences do not selectively hybridize, under stringent hybridization conditions, to the same cDNA as the polynucleotide and where the hybridization conditions include a wash step in 0.1×SSC and 0.1% sodium dodecyl sulfate at 65° C.

By "encoding" or "encoded," with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolumn* (Yamao, et al., (1985) *Proc. Natl. Acad. Sci. USA* 82:2306-9), or the ciliate Macronucleus, may be used when the nucleic acid is expressed using these organisms. As mentioned herein, when the nucleic acid is prepared or altered synthetically, advantage can be taken of known codon preferences of the intended host where the nucleic acid is to be expressed. For example, host cells include but are not limited to maize, soybean, sunflower, sorghum, canola, wheat, alfalfa, cotton, rice, barley, tomato, and millet cells. Although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) *Nucleic Acids Res.* 17:477-98 and herein incorporated by reference). Thus, the maize preferred codon for a particular amino acid might be derived from known gene sequences from maize. Maize codon usage for 28 genes from maize plants is listed in Table 4 of Murray, et al., supra.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived or, if from the same species, one or both are substantially modified from their original form. A heterologous protein may originate from a foreign species or, if from the same species, is substantially modified from its original form by deliberate human intervention.

By "host cell" is meant a cell, which comprises a heterologous nucleic acid sequence of the invention, which contains a vector and supports the replication and/or expression of the expression vector. Host cells may be prokaryotic cells such as *E. coli*, or eukaryotic cells such as yeast, insect, plant, amphibian, or mammalian cells. Preferably, host cells are monocotyledonous or dicotyledonous plant cells, including but not limited to maize, sorghum, sunflower, soybean, wheat, alfalfa, rice, cotton, canola, barley, millet, and tomato. A particularly preferred monocotyledonous host cell is a maize host cell. In one embodiment, the host cells are non-human host cells.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" refers to material, such as a nucleic acid or a protein, which is substantially or essentially free from components which normally accompany or interact with it as found in its naturally occurring environment. The isolated material optionally comprises material not found with the material in its natural environment. Nucleic acids, which are "isolated", as defined herein, are also referred to as "heterologous" nucleic acids. Unless otherwise stated, the term "NT nucleic acid" means a nucleic acid comprising a polynucleotide ("NT polynucleotide") encoding a full length or partial length NT polypeptide. Unless otherwise stated, the term "NT variant nucleic acid" means a nucleic acid comprising a polynucleotide ("NT variant polynucleotide") encoding a full length or partial length NT variant polypeptide. The term "NT polypeptide" refers to one or more amino acid sequences. The term is also inclusive of fragments, variants, homologs, alleles or precursors (e.g., preproproteins or proproteins) thereof. A "NT protein" comprises a NT polypeptide. The term "NT variant polypeptide" refers to one or more amino acid sequences. A "NT variant protein" comprises a NT variant polypeptide. The term is also inclusive of fragments, variants, homologs, alleles or precursors (e.g., preproproteins or proproteins) thereof.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, (1987) *Guide To Molecular Cloning Techniques*, from the series *Methods in Enzymology*, vol. 152, Academic Press, Inc., San Diego, Calif.; Sambrook, et al., (1989) *Molecular Cloning: A Laboratory Manual, 2$^{nd}$ ed.*, vols. 1-3; and *Current Protocols in Molecular Biology*, Ausubel, et al., eds, Current Protocols, a joint venture between Greene Publishing Associates, Inc. and John Wiley & Sons, Inc. (1994 Supplement).

As used herein "operably linked" includes reference to a functional linkage between a first sequence, such as a promoter, and a second sequence, wherein the promoter sequence initiates and mediates transcription of the DNA corresponding to the second sequence. Generally, operably linked means that the nucleic acid sequences being linked are contiguous and, where necessary to join two protein coding regions, contiguous and in the same reading frame. As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen, and microspores. The class of plants, which can be used in the methods of the invention, is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium*, and *Triticum*. Plants of the invention include, but are not limited to, rice, wheat, peanut, sugarcane, sorghum, corn, cotton, soybean, vegetable, ornamental, conifer, alfalfa, spinach, tobacco, tomato, potato, sunflower, canola, barley or millet *Brassica* sp., safflower, sweet potato, cassava, coffee, coconut, pineapple, citrus trees, cocoa, tea, banana, palm, avocado, fig, guava, mango, olive, papaya, cashew, *macadamia*, almond, sugar beet, sugarcane, buckwheat, triticale, spelt, linseed, sugar cane, oil seed rape, canola, cress, *Arabidopsis*, cabbages, soya, pea, beans, eggplant, bell pepper, Tagetes, lettuce, *Calendula*, melon, pumpkin, squash and zucchini or oat plant. A particularly preferred plant is *Zea mays*.

As used herein, "yield" may include reference to bushels per acre of a grain crop at harvest, as adjusted for grain moisture (15% typically for maize, for example), and the volume of biomass generated (for forage crops such as alfalfa, and plant root size for multiple crops). Grain moisture is measured in the grain at harvest. The adjusted test weight of grain is determined to be the weight in pounds per bushel, adjusted for grain moisture level at harvest. Biomass is measured as the weight of harvestable plant material generated.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such *Agrobacterium* or *Rhizobium*. Examples are promoters that preferentially initiate transcription in certain tissues, such as leaves, roots, seeds, fibres, xylem vessels, tracheids, or sclerenchyma. Such promoters are referred to as "tissue preferred." A "cell type" specific promoter primarily drives expression in certain cell types in one or more organs, for example, vascular cells in roots or leaves. An "inducible" or "regulatable" promoter is a promoter, which is under environmental control. Examples of environmental conditions that may effect transcription by inducible promoters include anaerobic conditions or the presence of light. Another type of promoter is a developmentally regulated promoter, for example, a promoter that drives expression during pollen development. Tissue preferred, cell type specific, developmentally regulated, and inducible promoters constitute the class of "non-constitutive" promoters. A "constitutive" promoter is a promoter, which is active under most environmental conditions, for example, the ubiquitin gene promoter Ub1 (GenBank accession no S94464).

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention; or may have reduced or eliminated expression of a native gene. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant polynucleotide" is a polynucleotide that is produced by recombinant DNA technology such as, for example, the shuffled polynucleotides disclosed herein. A "recombinant polypeptide" is a polypeptide encoded by a recombinant polynucleotide. Preferably, the recombinant polynucleotides of the invention do not have the same nucleotide sequence as that of a naturally occurring polynucleotide. Preferably, the recombinant polypeptides of the invention do not have the same amino acid sequence as that of a naturally occurring polypeptide.

As used herein, a "recombinant expression cassette" is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity, and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, (1984) *Anal. Biochem.*, 138:267-84: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, part I, chapter 2, "Overview of principles of hybridization and the strategy of nucleic acid probe assays," Elsevier, New York (1993); and *Current Protocols in Molecular Biology*, chapter 2, Ausubel, et al., eds, Greene Publishing and Wiley-Interscience, New York (1995). Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides or polypeptides: (a) "reference sequence," (b) "comparison window," (c) "sequence identity," (d) "percentage of sequence identity," and (e) "substantial identity."

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (BESTFIT) of Smith and Waterman, (1981) *Adv. Appl. Math* 2:482, may conduct optimal alignment of sequences for comparison; by the homology alignment algorithm (GAP) of Needleman and Wunsch, (1970) *J. Mol. Biol.* 48:443-53; by the search for similarity method (Tfasta and Fasta) of Pearson and Lipman, (1988) *Proc. Natl. Acad. Sci. USA* 85:2444; by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Version 8 (available from Genetics Computer Group (GCG®) programs (Accelrys, Inc., San Diego, Calif.).). The CLUSTAL program is well described by Higgins and Sharp, (1988) *Gene* 73:237-44; Higgins and Sharp, (1989) *CABIOS* 5:151-3; Corpet, et al., (1988) *Nucleic Acids Res.* 16:10881-90; Huang, et al., (1992) *Computer Applications in the Biosciences* 8:155-65, and Pearson, et al., (1994) *Meth. Mol. Biol.* 24:307-31. The preferred program to use for optimal global alignment of multiple sequences is PileUp (Feng and Doolittle, (1987) *J. Mol. Evol.*, 25:351-60 which is similar to the method described by Higgins and Sharp, (1989) *CABIOS* 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel et al., eds., Greene Publishing and Wiley-Interscience, New York (1995).

GAP uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) *Proc. Natl. Acad. Sci. USA* 89:10915).

Unless otherwise stated, sequence identity/similarity values provided herein refer to the value obtained using the BLAST 2.0 suite of programs using default parameters (Altschul, et al., (1997) *Nucleic Acids Res.* 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) *Comput. Chem.* 17:149-63) and XNU (Claverie and States, (1993) *Comput. Chem.* 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.* 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90%, and most preferably at least 95%, compared to a reference sequence using one of the alignment programs described using standard parameters.

One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90%, and most preferably at least 95%.

Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

A "subject plant or plant cell" is one in which genetic alteration, such as transformation, has been effected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A "control plant or plant cell" may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

The terms "substantial identity" in the context of a peptide indicates that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm of Needleman and Wunsch, supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides, which are "substantially similar" share sequences as, noted above except that residue positions, which are not identical, may differ by conservative amino acid changes.

"Variants" is intended to include substantially similar sequences. For polynucleotides, a variant comprises a deletion and/or addition of one or more nucleotides at one or more sites within the parental polynucleotide, e.g. a native polynucleotide from a fungus or plant, that may be codon-optimized, and/or a substitution of one or more nucleotides at one or more sites in the parental polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the NT variant polypeptides of the invention. Naturally occurring variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode an NT variant protein employed in the invention. Generally, variants of a particular polynucleotide of the invention will have at least about 50%, 55%, 50%, 55%, 60%, 65%, 70%, 75%, 80%, 85%, 90%, 91%, 92%, 93%, 95%, 95%, 96%, 97%, 98%, 99% or more sequence identity to a particular reference polynucleotide, e.g., native NT polynucleotide or template NT polynucleotide, as determined by sequence alignment programs and parameters described elsewhere herein. Accordingly, NT variant polynucleotides that have 50%, 55%, 50%, 55%, 60%, 65%, 70%, 75%, 80%, 85%, 90%, 91%, 92%, 93%, 95%, 95%, 96%, 97%, 98%, 99% or more sequence identity to a polynucleotide of SEQ ID NO: 3, 5, 7, 9, or 11 are contemplated.

Variants of a particular polynucleotide employed in the invention (i.e., the reference or parental polynucleotide) can also be evaluated by comparison of the sequence identity between the polypeptide encoded by a variant polynucleotide and the polypeptide encoded by the reference or parental polynucleotide. Thus, for example, an isolated polynucleotide that encodes a polypeptide with a given percent sequence identity to any one of the polypeptides of SEQ ID NOS: 2, 4, 6, 8, or 10 is encompassed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 50%, 55%, 50%, 55%, 60%, 65%, 70%, 75%, 80%, 85%, 90%, 91%, 92%, 93%, 95%, 95%, 96%, 97%, 98%, 99% or more sequence identity.

"Variant" protein is intended to include a protein derived from the native or parental protein by deletion, substitution or addition of one or more amino acids at one or more sites in the native or parental protein and/or substitution of one or more amino acids at one or more sites in the native or parental protein. Variant proteins encompassed by the present invention are biologically active, that is they continue to possess the desired biological activity of the native or parental protein, that is, NT activity as described herein. Such variants may result from, for example, genetic polymorphism or from human manipulation. Biologically active NT variants of the invention will have at least about 50%, 55%, 60%, 65%, 70%, 75%, 80%, 85%, 90%, 91%, 92%, 93%, 95%, 95%, 96%, 97%, 98%, 99% or more sequence identity to the amino acid sequence for the variant protein as determined by sequence alignment programs and parameters described elsewhere herein. Encompassed herein are NT variant polypeptides that have 50%, 55%, 50%, 55%, 60%, 65%, 70%, 75%, 80%, 85%, 90%, 91%, 92%, 93%, 95%, 95%, 96%, 97%, 98%, 99% or more sequence identity to a polypeptide of SEQ ID NO: 4, 6, 8, or 10.

A biologically active variant of a protein of the invention may differ from that protein by 50 or more amino acid residues, 30-50 residues, 15-30 amino acid residues, as few as 1-15 amino acid residues, as few as 1-10, such as 6-10, as few as 5, as few as 5, 3, 2, or even 1 amino acid residue. As used herein, the term "nitrate transporter variants" or "NT variants" includes but is not limited to the sequences or polymorphisms disclosed herein, their conservatively modified variants, regardless of source and any other variants which retain or increase the biological properties of the NT or NT variant, for example, NT activity as disclosed herein.

Figure 4:
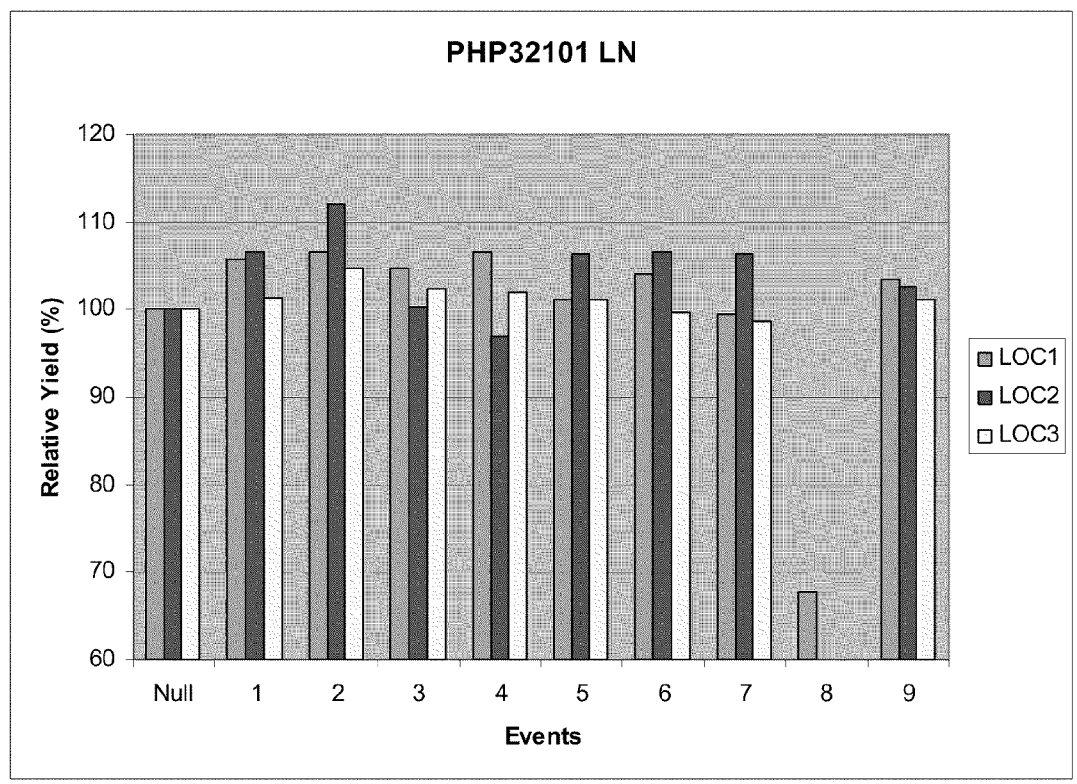
FIG. 4 is a graphical representation of the results of field yield trials of maize transgenic plants containing ZM-RM2:ADHI Intron:YNT1R3FS (PHP32101) at 3 locations under low nitrogen (LN) conditions. Eight events were tested at 3 locations and event 8 was only tested at 1 location. The relative yield (%) to the null is presented here.

The present invention relates to the expression of a nitrate transporter variant in plants. While other attempts to improve nitrate uptake in a plant by over-expressing a nitrate transporter have failed (See, for example, Fraisier et al., *Plant J.*, (2000) 23:489-496), it is shown herein that maize transgenic lines expressing variants of a yeast nitrate transporter (YNT1) driven by a root-preferred promoter have improved yield compared to the non-transgenic siblings (null) under low nitrogen yield trials in the field and have improved yield potential compared to the null under low nitrogen conditions in greenhouse. See FIGS. 3 and 4, and Examples 10 and 11 respectively.

Accordingly, plants expressing NT variants as described herein may have improved nitrate uptake when grown under normal or limited nitrogen fertility or enhance nitrogen use efficiency (NUE) of the plants. Advantageously, plants expressing NT variants as described herein may provide the customer increased revenue by lowering input costs or increasing yields with a significant reduction in applied nitrogen fertilizer or both. Furthermore, yields may be maintained or increased in plants expressing an NT variant as described herein even under non-favorable growth conditions, for example, where nitrogen is in limited supply.

As described elsewhere herein, the methods include expressing in a plant an NT variant polynucleotide as described herein. As used herein, the term nitrate transporter variant (NT variant) includes but is not limited to the sequences disclosed herein, such as NT variants described in Tables 1-3, their conservatively modified variants, regardless of source and any other variants which retain the biological properties of the NT, for example, NT activity as described herein. Such polynucleotides include those that encode NT variants, codon optimized NT variant coding sequences for NT variants, and conservative variants of these sequences. For example, suitable NT variants for use in the methods described herein include the coding portions of NT variant sequences which are optimized for expression in a particular plant, such as maize. The NT variants, including those derived from yeast NT's specific plant optimized and partially optimized NT variants, may be tested for expression level of the cognate NT variant protein using a transient expression assay, e.g. a maize transient expression assay such as that described in Example 26. Using the maize optimized NT variant polynucleotides of the present invention, the level of expression of the NT variant protein may be increased at least about 2 fold, 5 fold, 10 fold, 20 fold, 30 fold, 40 fold, 50 fold, 60 fold, 70 fold, 80 fold, 90 fold, or 100 fold as compared to a non-optimized NT variant polynucleotide.

Modulation of the expression level and/or activity of the NT variants described herein would provide a mechanism for manipulating a plant's nitrogen utilization efficiency (NUE). Accordingly, the present invention provides methods, polynucleotides, and polypeptides for the production of plants with maintained or improved yield under limited nitrogen supply or normal nitrogen conditions or both. In one aspect, the methods include introducing into a plant cell, plant tissue or plant one or more polynucleotides encoding NT variant polypeptides described herein having NT activity. This may be accomplished by introducing into the plant nuclear genome the NT variant polynucleotide driven by a suitable promoter, for example, a constitutive promoter or a root-preferred promoter. Exemplary suitable promoters are described elsewhere herein.

Figure 5:
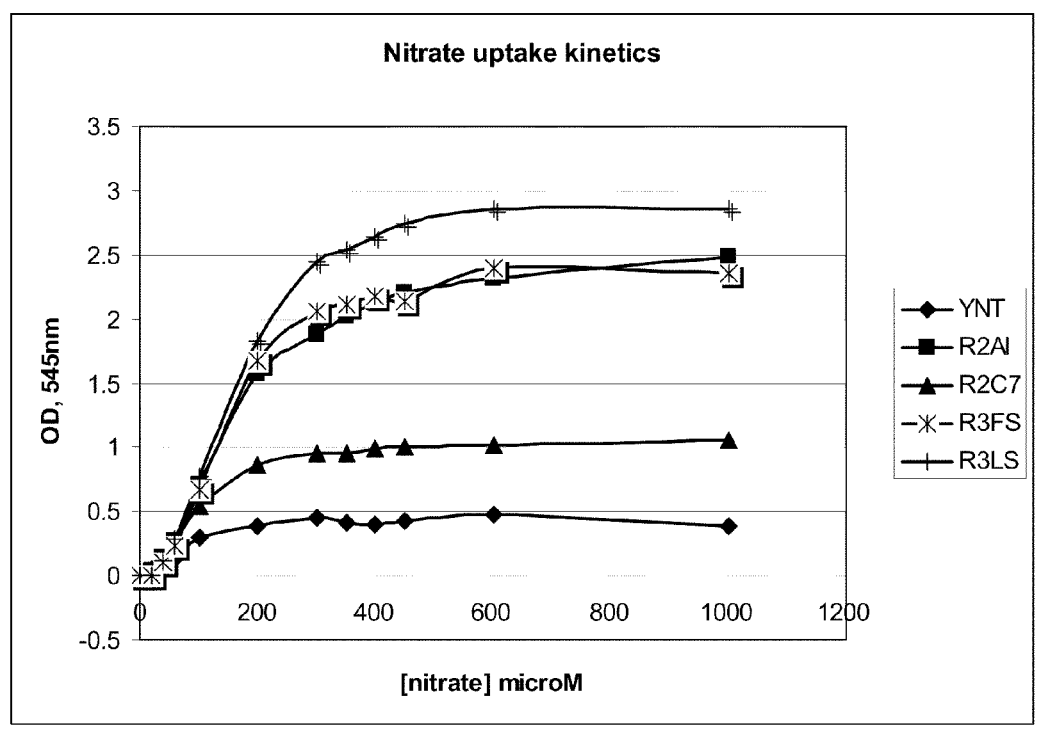
FIG. 5 is a graphical representation of the results of the nitrate uptake kinetic comparison among wt NT and four shuffled variants under normalized assay conditions. In this case, the most consistent kinetic parameters are maximal uptake velocities.

Disclosed herein are NT variants that have maintained or increased NT activity. As used interchangeably herein, a "NT activity", "biological activity of NT" or "functional activity of NT", refers to an activity exerted by a NT protein, polypeptide or portion thereof as determined in vivo, or in vitro, according to standard techniques. In one embodiment, NT activity is at least one or more of the following activities: (a) maintaining or increasing the uptake of nitrate as compared to the nitrate uptake of a control, (b) maintaining or increasing nitrate specificity, for example, decreased $K_m$ for nitrate, maintaining or increasing velocity ($V_{max}$) for nitrate uptake, maintaining or increasing turnover rate for nitrate, and the like as compared to the $K_m$, $V_{max}$, or turnover of a wild type NT, such as YNT1 (c) maintaining or increasing nitrogen use efficiency (NUE) of a plant as compared to the NUE of a control plant, (d) maintaining or increasing plant productivity/yield, as compared to the productivity/yield of a control plant, or (e) any of the activities of (a) to (d). The activity of an NT of the present invention may be compared with an appropriate control, for example, in vitro in a yeast system expressing an individual functional plant NT or in vivo, e.g. in a plant having an NT of the invention as compared to a control plant, a plant not transgenic for an NT of the present invention and/or transformed with a null construct. As shown in Example 2 below and in FIG. 5, the NT variants of YNT1R2AL, YNT1R2C7, YNT1R3FS and YNT1R3LS, have 2 to 5-fold higher catalytic efficiency compared to wild type YNT1.

The expression level of the NT variant polypeptide may be measured directly, for example, by measuring the level of the NT variant polypeptide by Western in the plant, or indirectly, for example, by measuring the NT activity of the NT variant polypeptide in the plant. Methods for determining the NT activity may be determined using known methods such as mutant complementation with a known NT, including the evaluation of the expression of the putative NT gene or activity in various expression systems, for example of *Xenopus* oocytes (See Miller, A. J. and Zhou, J. J., *Xenopus* Oocytes as an Expression System for Plant Transporters, Biochimica et Biophysica Acta. (2000). 1465: 343-358.) or in a yeast system of *Pichia pastoris* described in U.S. patent application Ser. No. 12/136,173. See, for example, *Accumulation of nitrate in the shoot acts as a signal to regulate shoot: root allocation in tobacco*. Plant J. 11: 671-691. See also, for example, a pH dye based system for measuring nitrate uptake in U.S. patent application Ser. No. 12/166,476, U.S. Patent Application Publication No. 2009/0011516. Methods for determining the reduction of nitrate to nitrite, nitrate reduction rate and/or specificity for nitrate, may be determined using standard techniques such as a Griess reaction colorimetric assay and those described in Hageman et al., *Methods Enzymol*. (1971) 23:491-503, Tucker D E, Allen D J Ort D R (2004). *Control of nitrate reductase by circadium and diurnal rhythms in tomato*. Planta 219:277-285. and Scheible W R, Lauerer M, Schultze E D, Caboche M, Stitt M (1997), Fiddler R M, *Collaborative Study of Modified AOAC Method of Analysis for Nitrite in Meat and Meat Products*, J. AOAC, 60, 594-99, (1977).

NT activity may also include evaluation of phenotypic changes, such as increased or maintained yield or NUE in a plant grown under nitrate limiting conditions such as lower nitrogen fertility. Examples of phenotypic changes include but are not limited to increased ear size in maize, increased shoot biomass, increased ear growth rate, increased biomass, higher grain yields, synchronous flowering so that pollen is shed at approximately the same time as silking, enhanced root growth, enhanced root structures, increased seed size, increased seed weight, seed with increased embryo size, increased leaf size, increased seedling vigor, enhanced silk emergence, and greater chlorophyll content (greener).

The NUE may inferred or determined by evaluating any number of components of NUE, including but not limited to remobilization of N, seed filling stage, stay green (chlorophyll content), senescence, the amount of nitrogen uptake, rate of nitrogen uptake under conditions of non-limiting or limiting N conditions. Assays for use in determining various aspects of NUE are described in Examples 7-15 and in U.S. patent application Ser. No. 12/136,173 and include but are not limited to Icoria Root NUE, NUE soil assay of *Arabidopsis*, TTC assay as described in U.S. patent application Ser. No. 61/227,276, biomass evaluation, and chlorophyll content (SPAD) assays. Additional assays for measuring NUE aspects will be known to one skilled in the art.

In one aspect, the invention includes an isolated or recombinant polypeptide with increased NT activity relative to naturally occurring enzymes involved in nitrate transport, e.g., a wild type NT enzyme. Generally, such polypeptides are NT's. For example, isolated or recombinant polypeptides of the invention have an NT activity that is at least about 1-fold, 1.5-fold, 2.0-fold, 2.5-fold, 3-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10.0-fold, 11-fold, 11.5-fold, 12.0-fold, 12.5-fold, 13-fold, 13.5-fold, 14.0-fold, 14.5-fold, 15.0-fold, 15.5-fold, 16.0-fold, 16.5-fold, 17.0-fold, 17.5-fold, 18.0-fold, 18.5-fold, 19.0-fold, 19.5-fold, 20.0-fold, 21-fold, 21.5-fold, 22.0-fold, 22.5-fold, 23-fold, 23.5-fold, 24.0-fold, 24.5-fold, 25.0-fold, 25.5-fold, 26.0-fold, 26.5-fold, 27.0-fold, 27.5-fold, 28.0-fold, 28.5-fold, 29.0-fold, 29.5-fold, 30.0-fold, or greater than a naturally occurring (native or wild-type) enzyme, such as exemplified by SEQ ID NO:2 of YNY1 NT or as described elsewhere herein.

For example, maintained or increased NT activity of an NT variant polypeptide can be conferred by alterations in the binding of, or alterations in the conversion activity of, an NT substrate such as nitrate. For example, the polypeptide of the invention having an increased NT activity can have a higher $k_{cat}$ than any of the naturally occurring enzymes, e.g., exemplified by or achieved by SEQ ID NO:2 (YNT1). Alternatively, or in addition, the polypeptide of the invention may have a lower or decreased $K_M$ than any of the naturally occurring enzymes, e.g. SEQ ID NO:2. Compositions include plants having altered levels of NT variants and/or activities of an NT enzyme. Further provided are plants having an altered level of NT variant polypeptides or an active variant or fragment thereof and/or maintained or increased NT activity. Also included are NT variants having maintained or increased activity than the activity of the wild-type or codon-optimized NT, such as YNT1. In one aspect, the plants comprise the NT variant polypeptide encoded by a polynucleotide having one or more of the substitutions shown in Table 3 or produced using any of the methods of the present invention.

In specific compositions, the plants have an altered level of an NT variant polypeptide of the present invention or an active variant or fragment thereof. These, include, but are not limited to NT variant polypeptides having one or more of the amino acid substitutions listed in Table 2 or combinations thereof. The variant may have maintained or increased NT activity compared to the wild type or native NT, for example, that results in a plant having increased yield or NUE or both. In another aspect, the plants have an altered level of NT activity when an NT variant polypeptide of the present invention or produced by the methods of the present invention or an active variant or fragment thereof is expressed in a plant cell. The variants can be tested to determine NT activity as described elsewhere herein.

The NT variants may be generated using shuffling or site-directed mutagenesis or other methods known to one skilled in the art. The variants, including NT variant polypeptides or polynucleotides, may be assayed for NT activity in vitro or in vivo.

In one aspect, shuffled gene variants can be screened for NT activity in a *Pichia pastoris* host as described in U.S. patent application Ser. No. 12/136,173 or any other suitable host. The variants with NT activity or increased NT activity can then be used to transform a plant cell to test for affect on yield or NUE, for example.

In addition, the present invention provides novel compositions and methods for modulating, for example, increasing or decreasing, the expression level or activity of NT protein in a plant cell or plant. In particular, the variant polynucleotides and polypeptides of the present invention can be used to generate transgenic plants expressing NT variants of the present invention. Modulation of the NT variants of the present invention would provide a mechanism for increasing a plant's nitrate uptake, NUE, yield or combinations thereof. Thus, one embodiment provides methods for modulating, for example, increasing or decreasing, a plant's nitrate uptake, NUE, or yield using NT variant polynucleotides and polypeptides of the present invention or produced by methods of the present invention. Variants of NT polynucleotides of the present invention encoding NT variants having amino acid substitutions and maintained or increased NT activity may be created by any number of methods, including but not limited to shuffling, site-directed mutagenesis, and the like. Such methods and techniques are described elsewhere herein.

Maintained or increased yield may be achieved through the NT variants described herein. Thus, modulation of NT activity in a plant cell using the NT variants described herein provides a novel strategy for maintaining or increasing yield or NUE of a plant grown under limited nitrogen supply or lower nitrogen fertility Accordingly, the present invention further provides plants having increased yield or a maintained yield when grown under limited nitrogen fertility. In some embodiments, the plants having an increased or maintained yield when grown under limited nitrogen fertility have a modulated expression level of NT or NT activity or both.

Compositions

Nucleic Acids

The present invention provides, inter alia, isolated nucleic acids of RNA, DNA, and analogs and/or chimeras thereof, comprising a NT variant polynucleotide. The present invention also includes variant polynucleotides optimized for expression in different organisms. For example, for expression of the variant polynucleotide in a maize plant, the sequence can be altered to account for specific codon preferences and to alter GC content as according to Murray, et al, supra. Codon optimization is described below.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, shuffled. amplified, or otherwise constructed from a fungus or bacteria. Shuffling or other techniques may be used to substitute 1, 2, 3, 4, 5, 6, 7, 8, 9, 10, 11, 12, 13, 14, 15, 16, 17, 18, 19, 20, 25, 30, 35, 40, 45, 50, 55 or nucleotides in an NT polynucleotide so that the resulting NT variant polypeptide differs from the polypeptide encoded by the parental or template NT or NT variant polynucleotide.

The nucleic acids may conveniently comprise sequences in addition to a variant polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated variant polynucleotide of the present invention. For example, a hexa-histidine marker sequence provides a convenient means to purify the proteins of the present invention. The nucleic acid of the present invention—excluding the variant polynucleotide sequence—is optionally a vector, adapter, or linker for cloning and/or expression of a variant polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known in the art. Exemplary nucleic acids include such vectors as: M13, lambda ZAP Express, lambda ZAP II, lambda gt10, lambda gt11, pBK-CMV, pBK-RSV, pBluescript II, lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3'SS, pGEM, pSK+/−, pGEX, pSPORTI and II, pOPRSVI CAT, pOPI3 CAT, pXT1, pSG5, pPbac, pMbac, pMC1neo, pOG44, pOG45, pFRTβGAL, pNEOβGAL, pRS403, pRS404, pRS405, pRS406, pRS413, pRS414, pRS415, pRS416, lambda MOSSlox, and lambda MOSElox. Optional vectors for the present invention, include but are not limited to, lambda ZAP II, and pGEX. For a description of various nucleic acids see, e.g., Stratagene Cloning Systems, Catalogs 1995, 1996, 1997 (La Jolla, Calif.); and, Amersham Life Sciences, Inc, Catalog '97 (Arlington Heights, Ill.).

Synthetic Methods for Constructing Nucleic Acids

The isolated nucleic acids of the present invention can also be prepared by direct chemical synthesis by methods such as the phosphotriester method of Narang, et al., (1979) *Meth. Enzymol.* 68:90-9; the phosphodiester method of Brown, et al., (1979) *Meth. Enzymol.* 68:109-51; the diethylphosphoramidite method of Beaucage, et al., (1981) *Tetra. Letts.* 22(20): 1859-62; the solid phase phosphoramidite triester method described by Beaucage, et al., supra, e.g., using an automated synthesizer, e.g., as described in Needham-VanDevanter, et al., (1984) *Nucleic Acids Res.* 12:6159-68; and, the solid support method of U.S. Pat. No. 4,458,066. Chemical synthesis generally produces a single stranded oligonucleotide. This may be converted into double stranded DNA by hybridization with a complementary sequence or by polymerization with a DNA polymerase using the single strand as a template. One of skill will recognize that while chemical synthesis of DNA is limited to sequences of about 100 bases, longer sequences may be obtained by the ligation of shorter sequences.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) *Nucleic Acids Res.* 15:8125) and the 5<G>7 methyl GpppG RNA cap structure (Drummond, et al., (1985) *Nucleic Acids Res.* 13:7375). Negative elements include stable intramolecular 5' UTR stem-loop structures (Muesing, et al., (1987) *Cell* 48:691) and AUG sequences or short open reading frames preceded by an appropriate AUG in the 5' UTR (Kozak, supra, Rao, et al., (1988) *Mol. and Cell. Biol.* 8:284). Accordingly, the present invention provides 5' and/or 3' UTR regions for modulation of translation of heterologous coding sequences.

As mentioned above, the polypeptide-encoding segments of the variant polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Expression may be optimized for the specific plant by engineering the variant polynucleotide sequence so that it uses the plant preferred codon. As used herein, the preferred codon refers to the preference exhibited by a specific host cell in the usage of nucleotide codons to specify a given amino acid. The preferred codon for an amino acid for a particular host is the single codon which most frequently encodes that amino acid in that host. The maize preferred codon for a particular amino acid may be derived from known gene sequences from maize. For example, when the plant is maize, the preferred codon usage may be determined by evaluating known genes from maize plants and determining how frequently a particular codon is used. See also Table 4 of Murray et al., Nucleic Acids Research, 17:477-498 (1989). For instance, the maize preferred codon for alanine is GCC, since, according to pooled sequences of 26 maize genes in Murray et al., supra, that codon encodes alanine 36% of the time, compared to GCG (24%), GCA (13%), and GCT (27%) Table 4 of Murray et al. is reproduced below.

In some cases, each codon in the NT variant sequence will be optimized for expression in maize using maize preferred codons, for example, where the NT variant sequence of the polynucleotide comprises 100 percent of the maize preferred codon sequences for the particular NT variant polypeptide. For example, the NT variant polynucleotide of SEQ ID NO:9 (YNT1R3FSMO) has a nucleotide sequence that comprises 100 percent maize preferred codon sequences and encodes a polypeptide with the same amino acid sequence as that produced by the YNT1R3FS protein (SEQ ID NO:8). Accordingly, the sequence of the NT variant polynucleotide is modified for optimized maize expression. In some cases, the NT variant polynucleotide sequence may be modified so that the overall G+C content of the ORF of polynucleotide is 60%, 65%, 70%, 75%, 80%, 85%, 90% or more of the total length of the sequence coding for the open-reading frame of the NT variant. In another aspect, the NT variant sequence may be modified so that restriction sites, cryptic intron donor or acceptor sites or both, RNA instability sites, and long homogenous base stretches or combinations thereof are eliminated.

In some aspects, the NT variant polynucleotide may be partially optimized for the plant cell in which it is to be expressed. For example, when the NT variant polynucleotide is to be expressed in maize, the maize NT variant polynucleotide is comprised of sequences which have been in part optimized for expression in maize. The partially optimized NT variant polynucleotide expresses the NT variant protein at a level sufficient to increase NT activity, for example, increase the yield of the plant, and such expression may be at a higher level than achieved as compared to a control, e.g. a corresponding wild type NT or NT variant polynucleotide sequence whose sequence has not been modified for expression in maize to include maize preferred codons. Partially plant optimized sequences include those in which, with respect to the entire length of the sequence, the sequence contains at least about 30%, 40%, 50% 60%, 70%, 80%, 90% or 100% of the plant-preferred codons. Accordingly, when the partially plant optimized sequence is for a maize plant, the sequence may include an overall sequence that contains at least about 30%, 40%, 50% 60%, 70%, 80%, 90% or 100% of the maize-preferred codons.

Codon usage in the coding regions of the polynucleotides of the present invention can be analyzed statistically using commercially available software packages such as "Codon Preference" available from the University of Wisconsin Genetics Computer Group. See, Devereaux, et al., (1984) *Nucleic Acids Res.* 12:387-395); or MacVector 4.1 (Eastman Kodak Co., New Haven, Conn.). Thus, the present invention provides a codon usage frequency characteristic of the coding region of at least one of the variant polynucleotides of the present invention. The number of polynucleotides (3 nucleotides per amino acid) that can be used to determine a codon usage frequency can be any integer from 3 to the number of polynucleotides of the present invention as provided herein. Optionally, the polynucleotides will be full-length sequences. An exemplary number of sequences for statistical analysis can be at least 1, 5, 10, 20, 50 or 100.

Sequence Shuffling

The present invention provides methods for sequence shuffling using polynucleotides of the present invention, and compositions resulting therefrom. Sequence shuffling is described in PCT publication No. 96/19256. See also, Zhang, et al., (1997) *Proc. Natl. Acad. Sci. USA* 94:4504-9; and Zhao, et al., (1998) *Nature Biotech* 16:258-61. Generally, sequence shuffling provides a means for generating libraries of polynucleotides having a desired characteristic, which can be selected or screened for. NT variant polynucleotides may be generated by any suitable shuffling method, for example, from one or more parental NT sequences or a combination thereof. The shuffling may optionally include mutagenesis, in vitro manipulation, in vivo manipulation of one or more sequences or in silico manipulation of sequences. The resultant shuffled polynucleotides may be introduced into a suitable host cell, typically in the form of expression cassettes wherein the shuffled polynucleotide sequence encoding the NT variant may be operably linked to a transcriptional regulatory sequence and any necessary sequences for ensuring transcription, translation, and processing of the encoded NT variant protein.

In one aspect, the parental or template polynucleotide is endogenous to a fungal organism or plant. The parental or template polynucleotide may be a wild type fungal NT, for example, NT polynucleotides from a fungi, such as the *Pichia angusta*, such as YNT1. Additionally, putative homologs or orthologs of the YNT1 sequences may be identified and isolated from other microbes and used in gene shuffling to increase sequence diversity.

The NT polynucleotides may be codon-optimized for a particular plant, e.g. maize or soybean, prior to or subsequent to shuffling.

Each such expression cassette or its shuffled NT variant encoding sequence can be referred to as a "library member" composing a library of shuffled NT variant sequences. In one aspect, E. coli or Pichia pastoris libraries may be constructed from single gene shuffling or semi-synthetic shuffling or combinations thereof in which the oligonucleotides are "spiked" to contain amino acid substitutions that differ from wild type NT's endogenous to a plant cell. See Example 2 as described herein. The library may be introduced into a population of host cells, such that individual host cells receive substantially one or a few species of library member(s), to form a population of shufflant host cells expressing a library of shuffled NT variant species.

A variety of NT genomic, cDNA, mRNA sources are known and can be used in the recombination processes herein. Coding sequences for NT for various species are disclosed in the literature and Genbank, among other public sources, and may be obtained by cloning, PCR, or from deposited materials. For example, as noted, a variety of references herein describe such genes. See, for example, Tsay Y F et al. *Nitrate transporters & Peptide Transporters,* 2007, FEBS lett. 581:2290-2300 and references within.

A protein with nitrate transporter activity which is particularly appreciated is YNT1 of *Pichia angusa*. Taking into account the degeneracy of the genetic code, a large number of nucleotide sequences encoding nitrate transporter exist which can also be used for the purposes of the invention. Examples of public databases that include NT sources include: Genbank: ncbi.nlm.nih.gov/genbank/: EMBL: ebi.ac.uk.embl/: as well as, e.g., the protein databank, Brookhaven Laboratories; the University of Wisconsin Biotechnology Center, the DNA databank of Japan, Laboratory of genetic Information Research, Misuina, Shizuda, Japan. With respect to NT sequences, over hundred different NT homologues are available in Genbank alone, including but not limited to confirmed and putative NT sequences from *Aspergillus nidulans* (XP_658612), *Tuber borchii* (AAQ04819), *Neurospora Crassa* (CAD71077) etc. Many NT sequences in the above mentioned databases can be used as diversity imputs for shuffling purposes.

The following publications describe a variety of recursive recombination procedures and/or methods which can be incorporated into such procedures, e.g., for shuffling of NT polynucleotides and/or fragments: Stemmer, et al., (1999) "Molecular breeding of viruses for targeting and other clinical properties. Tumor Targeting" 4:1-4; Ness et al. (1999) "DNA Shuffling of subgenomic sequences of subtilisin" Nature Biotechnology 17:893-896; Chang et al. (1999) "Evolution of a cytokine using DNA family shuffling" Nature Biotechnology 17:793-797; Minshull and Stemmer (1999) "Protein evolution by molecular breeding" Current Opinion in Chemical Biology 3:284-290; Christians et al. (1999) "Directed evolution of thymidine kinase for AZT phosphorylation using DNA family shuffling" Nature Biotechnology 17:259-264; Crameri et al. (1998) "DNA shuffling of a family of genes from diverse species accelerates directed evolution" Nature 391:288-291; Crameri et al. (1997) "Molecular evolution of an arsenate detoxification pathway by DNA shuffling," Nature Biotechnology 15:436-438; Zhang et al. (1997) "Directed evolution of an effective fucosidase from a galactosidase by DNA shuffling and screening" Proceedings of the National Academy of Sciences, U.S.A. 94:4504-4509; Patten et al. (1997) "Applications of DNA Shuffling to Pharmaceuticals and Vaccines" Current Opinion in Biotechnology 8:724-733; Crameri et al. (1996) "Construction and evolution of antibody-phage libraries by DNA shuffling" Nature Medicine 2:100-103; Crameri et al. (1996) "Improved green fluorescent protein by molecular evolution using DNA shuffling", Nature Biotechnology 14:315-319; Gates et al. (1996) "Affinity selective isolation of ligands from peptide libraries through display on a lac repressor 'headpiece dimer'" "Journal of Molecular Biology 255:3732 386; Stemmer (1996) "Sexual PCR and Assembly PCR" In: The Encyclopedia of Molecular Biology. VCH Publishers, New York. pp. 447-457; Crameri and Stemmer (1995) "Combinatorial multiple cassette mutagenesis creates all the permutations of mutant and wildtype cassettes" BioTechniques 18:194-195; Stemmer et al., (1995) "Single-step assembly of a gene and entire plasmid form large numbers of oligodeoxyribonucleotides" Gene, 164:49-53; Stemmer (1995) "The Evolution of Molecular Computation" Science 270:1510; Stemmer (1995) "Searching Sequence Space" Bio/Technology 13:549-553; Stemmer (1994) "Rapid evolution of a protein in vitro by DNA shuffling" Nature 370:389-391; and Stemmer (1994) "DNA shuffling by random fragmentation and reassembly: in vitro recombination for molecular evolution." Proceedings of the National Academy of Sciences. U.S.A. 91:10747-10751.

In addition, details and formats for DNA shuffling are found in a variety of PCT and foreign patent application publications, including: Stemmer and Crameri, "DNA Mutagenesis by Random Fragmentation and Reassembly" WO95/22625; Stemmer and Lipschutz "End Complementary Polymerase Chain Reaction" WO96/33207; Stemmer and Crameri "Methods for Generating Polynucleotides Having Desired Characteristics by Iterative Selection and Recombination" WO97/0078; Minshul and Stemmer, "Methods and Compositions for Cellular and Metabolic Engineering" WO97/35966; Punnonen et al. "Targeting of Genetic Vaccine Vectors" WO99/41402; Punnonen et al. "Antigen Library Immunization" WO99/41383; Punnonen et al. "Genetic Vaccine Vector Engineering" WO99/41369; Punnonen et al. "Optimization of Immunomodulatory Properties of Genetic Vaccines" WO99/41368; Stemmer and Crameri, "DNA Mutagenesis by Random Fragmentation and Reassembly" EP 0934999; Stemmer "Evolving Cellular DNA Uptake by Recursive Sequence Recombination" EP 0932670; Stemmer et al., "Modification of Virus Tropism and Host Range by Viral Genome Shuffling" WO99/23107; Apt et al., "Human Papillomavirus Vectors" WO99/21979; Del Cardayre et al. "Evolution of Whole Cells and Organisms by Recursive Sequence Recombination" WO98/31837; Patten and Stemmer, "Methods and Compositions for Polypeptide Engineering" WO98/27230; Stemmer et al., and "Methods for Optimization of Gene Therapy by Recursive Sequence Shuffling and Selection" WO98/13487.

As review of the foregoing publications, patents, published applications and U.S. patent applications reveals, recursive recombination and selection of polynucleotides to provide new NT variant polynucleotides with maintained or increased NT activity can be carried out by a number of established methods. Any of these methods can be adapted to the present invention to evolve NT or NT variant coding polynucleotides or homologues to produce new NT variant polypeptides with maintained or increased NT activity. Both the methods of making such enzymes and the enzymes or enzyme coding libraries produced by these methods are encompassed by the present invention.

A number of different general classes of recombination methods may be used to generate NT variants of the present invention. First, polynucleotides can be recombined in vitro by any of a variety of techniques discussed in the references above, including e.g., DNAse digestion of polynucleotides to be recombined followed by ligation and/or PCR reassembly of the polynucleotides. Second, polynucleotides can be recursively recombined in vivo, e.g., by allowing recombination to occur between polynucleotides in cells. Third, whole cell genome recombination methods can be used in which whole genomes of cells are recombined, optionally including spiking of the genomic or recombination mixtures so that they encode the desired amino acid substitutions shown to produce functional NT enzymes. See Example 2. Fourth, synthetic recombination methods can be used, in which oligonucleotides corresponding to different NT homologues are synthesized and reassembled in PCR or ligation reactions which include oligonucleotides which correspond to more than one parental polynucleotide, thereby generating new recombined polynucleotides. Oligonucleotides can be made by standard nucleotide addition methods, or can be made, e.g., by trinucleotide synthetic approaches. Fifth, in silico methods of recombination can be affected in which genetic algorithms are used in a computer to recombine sequence strings which correspond to NT homologues. The resulting recombined sequence strings are optionally converted into polynucleotides by synthesis of polynucleotides which correspond to the recombined sequences, e.g., in concert with oligonucleotide synthesis/gene reassembly techniques. Any of the preceding general recombination formats can be practiced in a reiterative fashion to generate a more diverse set of recombinant polynucleotides.

Combinations of in vitro and in vivo shuffling may be used to enhance combinatorial diversity. As mentioned previously, "in silico" shuffling may be used to generate NT variant polynucleotides using computer algorithms to perform "virtual" shuffling using genetic operators in a computer. In silico shuffling may be described in detail in Selifonov and Stemmer in "Methods for Making Character Strings, Polynucleotides & Polypeptides Having Desired Characteristics" filed Feb. 5, 1999, U.S. Ser. No. 60/118,854 and "Methods for Making Character Strings, Polynucleotides & Polypeptides Having Desired Characteristics" by Selifonov et al. filed Oct. 12, 1999 (U.S. Ser. No. 09/416,375).

One advantage of oligonucleotide-mediated recombination may be the ability to recombine homologous polynucleotides with low sequence similarity, or even non-homologous polynucleotides. In these low-homology oligonucleotide shuffling methods, one or more set of fragmented polynucleotides (e.g., oligonucleotides corresponding to multiple NT polynucleotides) are recombined, e.g., with a set of crossover family diversity oligonucleotides. Each of these crossover oligonucleotides have a plurality of sequence diversity domains corresponding to a plurality of sequence diversity domains from homologous or non-homologous polynucleotides with low sequence similarity. The fragmented oligonucleotides, which are derived by comparison to one or more homologous or non-homologous polynucleotides, can hybridize to one or more region of the crossover oligonucleotides, facilitating recombination.

When recombining homologous polynucleotides, sets of overlapping family gene shuffling oligonucleotides (which are derived by comparison of homologous polynucleotides, by synthesis of corresponding oligonucleotides) are hybridized and elongated (e.g., by reassembly PCR or ligation), providing a population of recombined polynucleotides, which can be selected for a desired trait or property. The set of overlapping family shuffling gene oligonucleotides includes a plurality of oligonucleotide member types which have consensus region subsequences derived from a plurality of homologous target polynucleotides.

In one aspect, family gene shuffling oligonucleotides that include one or more NT polynucleotide(s) are provided by aligning homologous polynucleotide sequences to select conserved regions of sequence identity and regions of sequence diversity. A plurality of family gene shuffling oligonucleotides may be synthesized (serially or in parallel) which correspond to at least one region of sequence diversity.

Sets of fragments, or subsets of fragments used in oligonucleotide shuffling approaches can be provided by cleaving one or more homologous polynucleotides (e.g., with a DNase), or, more commonly, by synthesizing a set of oligonucleotides corresponding to a plurality of regions of at least one polynucleotide (typically oligonucleotides corresponding to a full-length polynucleotide may be provided as members of a set of polynucleotide fragments). Cleavage fragments may be used in conjunction with family gene shuffling oligonucleotides, e.g., in one or more recombination reaction to produce recombinant NT polynucleotide(s).

Another approach of shuffling may be found in "Shuffling of Codon Altered Genes" by Patten et al. filed Sep. 29, 1998, (U.S. Ser. No. 60/102,362), Jan. 29, 1999 (U.S. Ser. No. 60/117,729), and Sep. 28, 1999, PCT/US99/22588. One way of generating diversity in a set of polynucleotides to be shuffled (i.e., as applied to the present invention, NT polynucleotides), may be to provide "spiked" polynucleotides containing mutations to decrease $K_M$, increase $K_{cat}$ by synthesizing polynucleotides in which the nucleotides which encode certain amino acid residues are altered, it may be possible to access a completely different mutational spectrum upon subsequent mutation of the polynucleotide. This increases the sequence diversity of the starting polynucleotides for shuffling protocols, which alters the rate and results of forced evolution procedures. Codon modification procedures can be used to modify any NT polynucleotide or shuffled polynucleotide, e.g., prior to performing DNA shuffling.

The above references provide these and other basic recombination formats as well as many modifications of these formats. Regardless of the format which may be used, the variant polynucleotides of the invention can be recombined (with each other or with related or even unrelated) polynucleotides to produce a diverse set of recombinant polynucleotides, including homologous polynucleotides.

Thus, in a general aspect, a sequence shuffling method provides for generating libraries or cells containing recombinant NT polynucleotides that may be screened for NT activity, for example, increased NT activity. Libraries of recombinant polynucleotides are generated from a population of related-sequence polynucleotides which comprise sequence regions which have substantial sequence identity and can be homologously recombined in vitro or in vivo. In the method, at least two species of the related-sequence polynucleotides are combined in a recombination system suitable for generating sequence-recombined polynucleotides, wherein said sequence-recombined polynucleotides comprise a portion of at least one first species of a related-sequence polynucleotide with at least one adjacent portion of at least one second species of a related-sequence polynucleotide. Recombination systems suitable for generating sequence-recombined polynucleotides can be either: (1) in vitro systems for homologous recombination or sequence shuffling via amplification or other formats or (2) in vivo systems for homologous recombination or site-specific recombination.

The population of sequence-recombined NT variant polynucleotides comprises a subpopulation of polynucleotides which are suspected of encoding polypeptides with NT activity, preferably increased NT activity. The selected sequence-recombined polynucleotides may be subjected to at least one recursive cycle wherein at least one selected sequence-recombined polynucleotide may be combined with at least one distinct species of related-sequence polynucleotide (which may itself be a selected sequence-recombined polynucleotide) in a recombination system suitable for generating sequence-recombined polynucleotides, such that additional generations of sequence-recombined polynucleotide sequences are generated from the selected sequence-recombined polynucleotides obtained by the selection or screening method employed. In this manner, recursive sequence recombination generates library members which are sequence-recombined NT polynucleotides possessing increased NT activity.

Polynucleotide sequence shuffling may be a method for recursive in vitro or in vivo homologous or non-homologous recombination of pools of NT polynucleotide fragments or polynucleotides (e.g., genes from fungal organisms or portions thereof). Mixtures of related NT polynucleotide sequences or polynucleotides are randomly or pseudorandomly fragmented, and reassembled to yield a library or mixed population of recombinant polynucleotides or polypeptides having NT activity. In an embodiment, the polynucleotides are fungal NT polynucleotides or combinations thereof.

The present invention may be directed to a method for generating a selected NT polynucleotide sequences or population of selected polynucleotide sequences, typically in the form of amplified and/or cloned polynucleotides, whereby the selected polynucleotide sequence(s) encode an NT variant polypeptide that can be selected for, and whereby the selected polypeptide sequences have NT activity, for example, maintained or increased NT activity.

In a general aspect, the invention provides a method for generating libraries of recombinant polynucleotides having a subpopulation of library members which encode an NT variant protein having maintained or increased NT activity. Libraries of recombinant polynucleotides may be generated from a population of related-sequence NT polynucleotides which comprise sequence regions which have substantial sequence identity and can be homologously recombined in vitro or in vivo. In another aspect, the libraries may be "spiked" to contain mutations not found in wild type plant NT's and that are found to produce functional NT enzymes and/or increased NT activity.

In one aspect, NT polynucleotides are combined in a recombination system suitable for generating sequence-recombined polynucleotides. In one aspect, the method includes an NT endogenous to the host cell as a template, for example, a shuffling template. In one aspect, the template is an NT gene or cDNA or other nucleotide sequence from *Pichia* or a species of *Pichia* or other fungal gene, such as a NT variant. In a preferred embodiment, the polynucleotides are from the *Pichia angusta*. Additionally, putative homologs of the *Pichia angusta* sequences identified and isolated from other microbes may be used in gene shuffling to increase sequence diversity. The polynucleotides may be from different organisms or species if desired. Recombination systems suitable for generating sequence-recombined polynucleotides can be either: (1) in vitro systems for homologous recombination or sequence shuffling via amplification or other formats described herein, or (2) in vivo systems for homologous recombination or site-specific recombination as described herein, or template-switching of a retroviral genome replication event. The population of sequence-recombined polynucleotides comprises a subpopulation of NT polynucleotides which possess desired or advantageous enzymatic characteristics and which can be selected by a suitable selection or screening method. The selected sequence-recombined polynucleotides, which may be related-sequence NT polynucleotides, can then be subjected to at least one recursive cycle wherein at least one selected sequence-recombined NT polynucleotide may be combined with another related-sequence NT polynucleotide (which may itself be a selected sequence-recombined polynucleotide) in a recombination system suitable for generating sequence-recombined polynucleotides with NT activity, such that additional generations of sequence-recombined polynucleotide sequences are generated from the selected sequence-recombined polynucleotides obtained by the selection or screening method employed. In this manner, recursive sequence recombination generates library members which are sequence-recombined polynucleotides possessing maintained or increased NT activity.

In one aspect, NT polynucleotides, e.g. library members, may be fragmented and homologously recombined by PCR in vitro. Fragment generation may be by nuclease digestion, partial extension PCR amplification, PCR stuttering, or other suitable fragmenting means, such as described herein and in WO95/22625 published Aug. 24, 1995, and in commonly owned U.S. Ser. No. 08/621,859 filed Mar. 25, 1996, PCT/US96/05480 filed Apr. 18, 1996, which are incorporated herein by reference. Stuttering may be fragmentation by incomplete polymerase extension of templates. A recombination format based on very short PCR extension times can be employed to create partial PCR products, which continue to extend off a different template in the next (and subsequent) cycle(s), and effect de facto fragmentation. Template-switching and other formats which accomplish sequence shuffling between a plurality of NT sequence-related polynucleotides-can be used. Such alternative formats will be apparent to those skilled in the art.

In one aspect, NT polynucleotides, e.g. library members, may be fragmented in vitro, the resultant fragments transferred into a host cell or organism and homologously recombined to form shuffled polynucleotides, in vivo. In one aspect, NT polynucleotides, e.g. library members, may be cloned or amplified on episomally replicable vectors, a multiplicity of said vectors may be transferred into a cell and homologously recombined to form NT polynucleotides, e.g. library members, in vivo.

In one aspect, NT polynucleotides, e.g. library members, may be not fragmented, but may be cloned or amplified on an episomally replicable vector as a direct repeat or indirect (or inverted) repeat, which each repeat comprising a distinct species of selected NT polynucleotide sequences, said vector may be transferred into a cell and homologously recombined by intra-vector or inter-vector recombination to form shuffled library members in vivo.

In one aspect, combinations of in vitro and in vivo shuffling are provided to enhance combinatorial diversity. The recombination cycles (in vitro or in vivo) can be performed in any order desired by the practitioner. In one aspect, the first plurality of selected library members may be fragmented and homologously recombined by PCR in vitro. Fragment generation may be by nuclease digestion, partial extension PCR amplification, PCR stuttering, or other suitable fragmenting means, such as described herein and in the documents incorporated herein by reference. Stuttering may be fragmentation by incomplete polymerase extension of templates.

In one aspect, NT polynucleotides, e.g. library members, may be fragmented in vitro, the resultant fragments transferred into a host cell or organism and homologously recombined to form shuffled polynucleotides, e.g. library members, in vivo. In an aspect, the host cell may be a unicellular photosynthetic eukaryotic organism or a plant cell. In one aspect, the plant cell has been engineered to contain enhanced recombination systems, such as an enhanced system for general homologous recombination (e.g., a plant expressing a recA protein or a plant recombinase from a transgene or plant virus) or a site-specific recombination system (e.g., a cre/LOX or frt/FLP system encoded on a transgene or plant virus).

In one aspect, NT polynucleotides, e.g. library members, may be cloned or amplified on episomally replicable vectors, a multiplicity of said vectors may be transferred into a cell and homologously recombined to form shuffled library members in vivo in a plant cell, algae cell, fungal, yeast, or bacterial cell. Other cell types may be used, if desired.

NT polynucleotides, e.g. library members, may not be fragmented, but may be cloned or amplified on an episomally replicable vector as a direct repeat or indirect (or inverted) repeat, which each repeat comprising a distinct species of NT polynucleotide sequences, said vector may be transferred into a cell and homologously recombined by intra-vector or inter-vector recombination to form shuffled library members in vivo in a plant cell, or microorganism.

At least one parental polynucleotide sequence that encodes an NT variant or an NT of a fungus, such as for example and not limitation, a polynucleotide sequence, for example, gene or cDNA sequence from *Pichia angusta*, among others having NT activity. The parental NT or NT variant polynucleotide may be subjected to mutagenesis and/or shuffling or combinations thereof to generate a population of mutagenized NT polynucleotides which have substantial sequence identity to the parental NT or NT variant polynucleotide sequence. The population of mutagenized polynucleotides may be transferred into a population of host cells wherein the mutagenized polynucleotides are expressed and the resultant transformed host cell population (transformants) may be selected or screened for NT activity, maintained or increased, or a phenotype thereof. The increase in such properties can be at least 10%, 20%, 30%, 40%, 50%, 60%, 70%, 80%, 90, 100%, 110%, 120%, 130%, 140%, 150% or greater than of the wild-type value.

A variety of suitable host cells for shuffling or determining NT sequences will be apparent to those skilled in the art. Any suitable host cell may be used so long as the host cell allows for the proper folding and processing of the NT. The host cell may be a plant cell, for example, *Arabidopsis*, soybean or an algae cell, fungal cell, yeast cell, or bacterial cell.

Recombinant Expression Cassettes

The present invention further provides recombinant expression cassettes comprising a nucleic acid of the present invention. A nucleic acid sequence coding for the desired variant polynucleotide of the present invention, for example a cDNA or a genomic sequence encoding a polypeptide long enough to code for an active protein of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A number of promoters can be used in the practice of the invention, including a native promoter of an endogenous NT polynucleotide sequence of the crop plant of interest. The promoters can be selected based on the desired outcome. The nucleic acids can be combined with constitutive, tissue-preferred, inducible, or other promoters for expression in plants.

A plant promoter or promoter fragment can be employed which will direct expression of a variant polynucleotide of the present invention in all tissues of a regenerated plant. Such promoters are referred to herein as "constitutive" promoters and are active under most environmental conditions and states of development or cell differentiation. Examples of constitutive promoters include the 1'- or 2'-promoter derived from T-DNA of *Agrobacterium tumefaciens*, the Smas promoter, the cinnamyl alcohol dehydrogenase promoter (U.S. Pat. No. 5,683,439), the Nos promoter, the rubisco promoter, the GRP1-8 promoter, the 35S promoter from cauliflower mosaic virus (CaMV), as described in Odell, et al., (1985) *Nature* 313:810-2; rice actin (McElroy, et al., (1990) *Plant Cell* 163-171); ubiquitin (Christensen, et al., (1992) *Plant Mol. Biol.* 12:619-632 and Christensen, et al., (1992) *Plant Mol. Biol.* 18:675-89); pEMU (Last, et al., (1991) *Theor. Appl. Genet.* 81:581-8); MAS (Velten, et al., (1984) *EMBO J.* 3:2723-30); and maize H3 histone (Lepetit, et al., (1992) *Mol. Gen. Genet.* 231:276-85; and Atanassvoa, et al., (1992) *Plant Journal* 2(3):291-300); ALS promoter, as described in PCT Application No. WO 96/30530; and other transcription initiation regions from various plant genes known to those of skill. For the present invention, a root-preferred promoter, the maize ubiquitin promoter, or a viral promoter such as banana streak virus promoter truncated version (BSV (TR) PRO) and full version (BSV PRO) are the preferred promoter for expression in monocot plants.

Tissue-preferred promoters can be utilized to target enhanced NT variant expression within a particular plant tissue. By "tissue-preferred" is intended to mean that expression is predominately in a particular tissue, albeit not necessarily exclusively in that tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 255(3):337-353; Russell et al. (1997) *Transgenic Res.* 6(2):157-168; Rinehart et al. (1996) *Plant Physiol.* 112(3):1331-1351; Van Camp et al. (1996) *Plant Physiol.* 112(2):525-535; Canevascini et al. (1996) *Plant Physiol.* 112(2):513-525; Yamamoto et al. (1995) *Plant Cell Physiol.* 35(5):773-778; Lam (1995) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 5(3):595-505. Such promoters can be modified, if necessary, for weak expression. See, also, U.S. Patent Application No. 2003/0074698, herein incorporated by reference.

A mesophyllic cell preferred promoter includes but is not limited to promoters such as known phosphoenopyruvate decarboxylase (PEPC) promoters or putative PEPC promoters from any number of species, for example, *Zea mays, Oryza sativa, Arabidopsis thaliana, Glycine max*, or *Sorghum bicolor*. Examples include *Zea mays* PEPC of GenBank accession no. gi:116268332_HTG AC190686, and gCAT GSS composite sequence; *Oryza sativa* PEPC of GenBank accession no. gi|20804452|dbj|AP003052.3|; *Arabidopsis thaliana* PEPC of GenBank accession nos. gi|5541653|dbj|AP000370.1|AP000370; gi:7769847; or gi|20198070|gb|AC007087.7; *Glycine max* (GSS contigs); or *Sorghum bicolor* (JGI assembly scaffold_832, 89230 bp., JGI assembly scaffold_1632. (1997) *Plant J.* 12(2):255-265; Kwon et al. (1995) *Plant Physiol.* 105:357-67; Yamamoto et al. (1995) *Plant Cell Physiol.* 35(5):773-778; Gotor et al. (1993) *Plant J.* 3:509-18; Orozco et al. (1993) *Plant Mol. Biol.* 23(6):1129-1138; Baszczynski et al. (1988) *Nucl. Acid Res.* 16:5732; Mitra et al. (1995) *Plant Molecular Biology* 26:35-93; Kayaya et al. (1995) *Molecular and General Genetics* 258:668-675; and Matsuoka et al. (1993) *Proc. Natl. Acad. Sci. USA* 90(20):9586-9590. Senescence regulated promoters are also of use, such as, SAM22 (Crowell et al. (1992) *Plant Mol. Biol.* 18:559-566). See also U.S. Pat. No. 5,589,052, herein incorporated by reference.

Shoot-preferred promoters include, shoot meristem-preferred promoters such as promoters disclosed in Weigal et al. (1992) *Cell* 69:853-859; Accession No. AJ131822; Accession No. Z71981; Accession No. AF059870, the ZAP promoter (U.S. patent application Ser. No. 10/387,937), the maize tb1 promoter (Wang et al. (1999) *Nature* 398:236-239, and shoot-preferred promoters disclosed in McAvoy et al. (2003) *Acta Hort.* (ISHS) 625:379-385.

Root-preferred promoters are known and can be selected from the many available from the literature or isolated de novo from various compatible species. Exemplary root-preferred promoters include but are not limited to root-preferred promoter, e.g. maize root metallothionein promoter (ZM-RM2 PRO), maize NAS2 promoter, and viral promoters such as banana streak virus promoter truncated version (BSV (TR) PRO) and full version (BSV (FL) PRO). See U.S. Pat. No. 7,214,855 issued May 8, 2007 for ZM-RM2 promoter, and U.S. patent application Ser. No. 61/184,043 filed Jun. 4, 2009, for BSV TR (BSV truncated) promoter, incorporated herein in their entirety. See also, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 15(3):533-553 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-651, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):353-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(5):759-772); rolB promoter (Capana et al. (1995) *Plant Mol. Biol.* 25(5):681-691; and the CRWAQ81 root-preferred promoter with the ADH first intron (U.S. Pat. No. 7,411,112, filed Oct. 9, 2003, herein incorporated by reference). See also U.S. Pat. Nos. 5,837,876; 5,750,386; 5,633,363; 5,559,252; 5,501,836; 5,110,732; and 5,023,179.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter, which is inducible by hypoxia or cold stress, the Hsp70 promoter, which is inducible by heat stress, and the PPDK promoter, which is inducible by light.

Examples of promoters under developmental control include promoters that initiate transcription only, or preferentially, in certain tissues, such as leaves, roots, fruit, seeds, or flowers. The operation of a promoter may also vary depending on its location in the genome. Thus, an inducible promoter may become fully or partially constitutive in certain locations.

If polypeptide expression is desired, it is generally desirable to include a polyadenylation region at the 3'-end of a polynucleotide coding region. The polyadenylation region can be derived from a variety of plant genes, or from T-DNA. The 3' end sequence to be added can be derived from, for example, the nopaline synthase or octopine synthase genes, or alternatively from another plant gene, or less preferably from any other eukaryotic gene. Examples of such regulatory elements include, but are not limited to, 3' termination and/or polyadenylation regions such as those of the *Agrobacterium tumefaciens* nopaline synthase (nos) gene (Bevan, et al., (1983) *Nucleic Acids Res.* 12:369-85); the potato proteinase inhibitor II (PINII) gene (Keil, et al., (1986) *Nucleic Acids Res.* 14:5641-50; and An, et al., (1989) *Plant Cell* 1:115-22); and the CaMV 19S gene (Mogen, et al., (1990) *Plant Cell* 2:1261-72).

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, (1988) *Mol. Cell Biol.* 8:4395-4405; Callis, et al., (1987) *Genes Dev.* 1:1183-200). Such intron enhancement of gene expression is typically greatest when placed near the 5' end of the transcription unit. Use of maize introns Adh1-S intron 1, 2 and 6, the Bronze-1 intron are known in the art. See generally, *The Maize Handbook*, Chapter 116, Freeling and Walbot, eds., Springer, New York (1994).

Plant signal sequences, including, but not limited to, signal-peptide encoding DNA/RNA sequences which target proteins to the extracellular matrix of the plant cell (Dratewka-Kos, et al., (1989) *J. Biol. Chem.* 264:4896-900), such as the *Nicotiana plumbaginifolia* extension gene (DeLoose, et al., (1991) *Gene* 99:95-100); signal peptides which target proteins to the vacuole, such as the sweet potato sporamin gene (Matsuka, et al., (1991) *Proc. Natl. Acad. Sci. USA* 88:834) and the barley lectin gene (Wilkins, et al., (1990) *Plant Cell,* 2:301-13); signal peptides which cause proteins to be secreted, such as that of PRIb (Lind, et al., (1992) *Plant Mol. Biol.* 18:47-53) or the barley alpha amylase (BAA) (Rahmatullah, et al., (1989) *Plant Mol. Biol.* 12:119, and hereby incorporated by reference), or signal peptides which target proteins to the plastids such as that of rapeseed enoyl-Acp reductase (Verwaert, et al., (1994) *Plant Mol. Biol.* 26:189-202) are useful in the invention.

The vector comprising the sequences from a polynucleotide of the present invention will typically comprise a marker gene, which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, and the ALS gene encodes resistance to the herbicide chlorsulfuron. Additional selectable markers include phenotypic markers such as β-galactosidase and fluorescent proteins such as red fluorescent protein (RFP), green fluorescent protein (GFP) (Su et al. (2005) *Biotechnol Bioeng* 85:610-9 and Fetter et al. (2005) *Plant Cell* 16:215-28), cyan florescent protein (CYP) (Bolte et al. (2005) *J. Cell Science* 117:953-55 and Kato et al. (2002) *Plant Physiol* 129:913-52), and yellow florescent protein (PhiYFP™ from Evrogen, see, Bolte et al. (2005) *J. Cell Science* 117:953-55).

Typical vectors useful for expression of genes in higher plants are well known in the art and include vectors derived from the tumor-inducing (Ti) plasmid of *Agrobacterium tumefaciens* described by Rogers, et al. (1987), *Meth. Enzymol.* 153:253-77. These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl, et al., (1987) *Gene* 61:1-11, and Berger, et al., (1989) *Proc. Natl. Acad. Sci. USA*, 86:8402-6. Another useful vector herein is plasmid pBI101.2 that is available from CLONTECH Laboratories, Inc. (Palo Alto, Calif.).

Expression of Proteins in Host Cells

Using the nucleic acids of the present invention, one may express a variant protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a variant protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a variant protein of the present invention. To obtain high level expression of a cloned gene, it is desirable to construct expression vectors which contain, at the minimum, a strong promoter, such as ubiquitin, to direct transcription, a ribosome binding site for translational initiation, and a transcription/translation terminator. Constitutive promoters are classified as providing for a range of constitutive expression. Thus, some are weak constitutive promoters, and others are strong constitutive promoters. Generally, by "weak promoter" is intended a promoter that drives expression of a coding sequence at a low level. By "low level" is intended at levels of about $1/10,000$ transcripts to about $1/100,000$ transcripts to about $1/500,000$ transcripts. Conversely, a "strong promoter" drives expression of a coding sequence at a "high level," or about $1/10$ transcripts to about $1/100$ transcripts to about $1/1,000$ transcripts.

One of skill would recognize that modifications could be made to a variant protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang, et al., (1977) *Nature* 198:1056), the tryptophan (trp) promoter system (Goeddel, et al., (1980) *Nucleic Acids Res.* 8:4057) and the lambda derived P L promoter and N-gene ribosome binding site (Shimatake, et al., (1981) *Nature* 292:128). The inclusion of selection markers in DNA vectors transfected in *E. coli* is also useful. Examples of such markers include genes specifying resistance to ampicillin, tetracycline, or chloramphenicol.

The vector is selected to allow introduction of the gene of interest into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a variant protein of the present invention are available using *Bacillus* sp. and *Salmonella* (Palva, et al., (1983) *Gene* 22:229-35; Mosbach, et al., (1983) *Nature* 302:543-5). The pGEX-4T-1 plasmid vector from Pharmacia is the preferred *E. coli* expression vector for the present invention.

Expression in Eukaryotes

A variety of eukaryotic expression systems such as yeast, insect cell lines, plant and mammalian cells, are known to those of skill in the art. As explained briefly below, the present invention can be expressed in these eukaryotic systems. In some embodiments, transformed/transfected plant cells, as discussed infra, are employed as expression systems for production of the variant proteins of the instant invention.

Synthesis of heterologous proteins in yeast is well known. Sherman, et al., (1982) *Methods in Yeast Genetics*, Cold Spring Harbor Laboratory is a well recognized work describing the various methods available to produce the protein in yeast. Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A variant protein of the present invention, once expressed, can be isolated from yeast by lysing the cells and applying standard protein isolation techniques to the lysates or the pellets. The monitoring of the purification process can be accomplished by using Western blot techniques or radioimmunoassay of other standard immunoassay techniques.

The sequences encoding variant proteins of the present invention can also be ligated to various expression vectors for use in transfecting cell cultures of, for instance, mammalian, insect, or plant origin. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen, et al., (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of variant proteins of the present invention are available, for instance, from the American Type Culture Collection Catalogue of Cell Lines and Hybridomas (7$^{th}$ ed., 1992).

Appropriate vectors for expressing variant proteins of the present invention in insect cells are usually derived from the SF9 baculovirus. Suitable insect cell lines include mosquito larvae, silkworm, armyworm, moth, and *Drosophila* cell lines such as a Schneider cell line (see, e.g., Schneider, (1987) *J. Embryol. Exp. Morphol.* 27:353-65).

As with yeast, when higher animal or plant host cells are employed, polyadenlyation or transcription terminator sequences are typically incorporated into the vector. An example of a terminator sequence is the polyadenlyation sequence from the bovine growth hormone gene. Other useful terminators for practicing this invention include, but are not limited to, pinII (See An et al. (1989) *Plant Cell* 1(1):115-122), glb1 (See Genbank Accession #L22345), gz (See gzw64a terminator, Genbank Accession #S78780), and the nos terminator from *Agrobacterium*.

Sequences for accurate splicing of the transcript may also be included. An example of a splicing sequence is the VP1 intron from SV40 (Sprague et al., *J. Virol.* 45:773-81 (1983)). Additionally, gene sequences to control replication in the host cell may be incorporated into the vector such as those found in bovine papilloma virus type-vectors (Saveria-Campo, "Bovine Papilloma Virus DNA a Eukaryotic Cloning Vector," in *DNA Cloning: A Practical Approach*, vol. II, Glover, ed., IRL Press, Arlington, Va., pp. 213-38 (1985)).

In addition, the NT variant polynucleotide placed in the appropriate plant expression vector can be used to transform plant cells. The polypeptide can then be isolated from plant callus or the transformed cells can be used to regenerate transgenic plants. Such transgenic plants can be harvested, and the appropriate tissues (seed or leaves, for example) can be subjected to large scale protein extraction and purification techniques.

Plant Transformation Methods

Numerous methods for introducing foreign genes into plants are known and can be used to insert an NT variant polynucleotide into a plant host, including biological and physical plant transformation protocols. See, e.g., Miki et al., "Procedure for Introducing Foreign DNA into Plants," in *Methods in Plant Molecular Biology and Biotechnology*, Glick and Thompson, eds., CRC Press, Inc., Boca Raton, pp. 67-88 (1993). The methods chosen vary with the host plant, and include chemical transfection methods such as calcium phosphate, microorganism-mediated gene transfer such as *Agrobacterium* (Horsch et al., *Science* 227:1229-31 (1985)), electroporation, micro-injection, and biolistic bombardment.

Expression cassettes and vectors and in vitro culture methods for plant cell or tissue transformation and regeneration of plants are known and available. See, e.g., Gruber et al., "Vectors for Plant Transformation," in *Methods in Plant Molecular Biology and Biotechnology*, supra, pp. 89-119.

The isolated polynucleotides or polypeptides may be introduced into the plant by one or more techniques typically used for direct delivery into cells. Such protocols may vary depending on the type of organism, cell, plant or plant cell, i.e. monocot or dicot, targeted for gene modification. Suitable methods of transforming plant cells include microinjection (Crossway, et al., (1986) *Biotechniques* 4:320-334; and U.S. Pat. No. 6,300,543), electroporation (Riggs, et al., (1986) *Proc. Natl. Acad. Sci. USA* 83:5602-5606, direct gene transfer (Paszkowski et al., (1984) *EMBO J.* 3:2717-2722), and ballistic particle acceleration (see, for example, Sanford, et al., U.S. Pat. No. 4,945,050; WO 91/10725; and McCabe, et al., (1988) *Biotechnology* 6:923-926). Also see, Tomes, et al., "Direct DNA Transfer into Intact Plant Cells Via Microprojectile Bombardment". pp. 197-213 in *Plant Cell, Tissue and Organ Culture, Fundamental Methods*. eds. O. L. Gamborg & G. C. Phillips. Springer-Verlag Berlin Heidelberg New York, 1995; U.S. Pat. No. 5,736,369 (meristem); Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); WO 91/10725 (maize); Klein, et al., (1988) *Plant Physiol.* 91:440-444 (maize); Fromm, et al., (1990) *Biotechnology* 8:833-839; and Gordon-Kamm, et al., (1990) *Plant Cell* 2:603-618 (maize); Hooydaas-Van Slogteren & Hooykaas (1984) *Nature* (London) 311:763-764; Bytebierm, et al., (1987) *Proc. Natl. Acad. Sci. USA* 84:5345-5349 (Liliaceae); De Wet, et al., (1985) *In The Experimental Manipulation of Ovule Tissues*, ed. G. P. Chapman, et al., pp. 197-209. Longman, NY (pollen); Kaeppler, et al., (1990) *Plant Cell Reports* 9:415-418; and Kaeppler, et al., (1992) *Theor. Appl. Genet.* 84:560-566 (whisker-mediated transformation); U.S. Pat. No. 5,693,512 (sonication); D'Halluin, et al., (1992) *Plant Cell* 4:1495-1505 (electroporation); Li, et al., (1993) *Plant Cell Reports* 12:250-255; and Christou and Ford, (1995) *Annals of Botany* 75:407-413 (rice); Osjoda, et al., (1996) *Nature Biotech.* 14:745-750; *Agrobacterium* mediated maize transformation (U.S. Pat. No. 5,981,840); silicon carbide whisker methods (Frame, et al., (1994) *Plant J.* 6:941-948); laser methods (Guo, et al., (1995) *Physiologia Plantarum* 93:19-24); sonication methods (Bao, et al., (1997) *Ultrasound in Medicine & Biology* 23:953-959; Finer and Finer, (2000) *Lett Appl Microbiol.* 30:406-10; Amoah, et al., (2001)

*J Exp Bot* 52:1135-42); polyethylene glycol methods (Krens, et al., (1982) *Nature* 296:72-77); protoplasts of monocot and dicot cells can be transformed using electroporation (Fromm, et al., (1985) *Proc. Natl. Acad. Sci. USA* 82:5824-5828) and microinjection (Crossway, et al., (1986) *Mol. Gen. Genet.* 202:179-185); all of which are herein incorporated by reference.

*Agrobacterium*-Mediated Transformation

The most widely utilized method for introducing an expression vector into plants is based on the natural transformation system of *Agrobacterium*. *A. tumefaciens* and *A. rhizogenes* are plant pathogenic soil bacteria, which genetically transform plant cells. The Ti and Ri plasmids of *A. tumefaciens* and *A. rhizogenes*, respectively, carry genes responsible for genetic transformation of plants. See, e.g., Kado, (1991) *Crit. Rev. Plant Sci.* 10:1. Descriptions of the *Agrobacterium* vector systems and methods for *Agrobacterium*-mediated gene transfer are provided in Gruber, et al., supra; Miki, et al., supra; and Moloney, et al., (1989) *Plant Cell Reports* 8:238.

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, (1989) *Science* 244:174-81. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658,082; U.S. Pat. No. 913,914, filed Oct. 1, 1986, as referenced in U.S. Pat. No. 5,262,306, issued Nov. 16, 1993; and Simpson, et al., (1986) *Plant Mol. Biol.* 6:403-15 (also referenced in the '306 patent); all incorporated by reference in their entirety.

Once constructed, these plasmids can be placed into *A. rhizogenes* or *A. tumefaciens* and these vectors used to transform cells of plant species, which are ordinarily susceptible to *Fusarium* or *Alternaria* infection. Several other transgenic plants are also contemplated by the present invention including but not limited to soybean, corn, sorghum, alfalfa, rice, clover, cabbage, banana, coffee, celery, tobacco, cowpea, cotton, melon and pepper. The selection of either *A. tumefaciens* or *A. rhizogenes* will depend on the plant being transformed thereby. In general *A. tumefaciens* is the preferred organism for transformation. Most dicotyledonous plants, some gymnosperms, and a few monocotyledonous plants (e.g., certain members of the Liliales and Arales) are susceptible to infection with *A. tumefaciens*. *A. rhizogenes* also has a wide host range, embracing most dicots and some gymnosperms, which includes members of the Leguminosae, Compositae, and Chenopodiaceae. Monocot plants can now be transformed with some success. European Patent Application No. 604 662 A1 discloses a method for transforming monocots using *Agrobacterium*. European Application No. 672 752 A1 discloses a method for transforming monocots with *Agrobacterium* using the scutellum of immature embryos. Ishida, et al., discuss a method for transforming maize by exposing immature embryos to *A. tumefaciens* (*Nature Biotechnology* 14:745-50 (1996)).

Once transformed, these cells can be used to regenerate transgenic plants. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, (1985) *Theor. Appl. Genet.* 69:235-40; U.S. Pat. No. 4,658,082; Simpson, et al., supra; and U.S. Pat. Nos. 913,913 and 913,914, both filed Oct. 1, 1986, as referenced in U.S. Pat. No. 5,262,306, issued Nov. 16, 1993, the entire disclosures therein incorporated herein by reference.

Direct Gene Transfer

Despite the fact that the host range for *Agrobacterium*-mediated transformation is broad, some major cereal crop species and gymnosperms have generally been recalcitrant to this mode of gene transfer, even though some success has recently been achieved in rice (Hiei, et al., (1994) *The Plant Journal* 6:271-82). Several methods of plant transformation, collectively referred to as direct gene transfer, have been developed as an alternative to *Agrobacterium*-mediated transformation.

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes (Sanford, et al., (1987) *Part. Sci. Technol.* 5:27; Sanford, (1988) *Trends Biotech* 6:299; Sanford, (1990) *Physiol. Plant* 79:206; and Klein, et al., (1992) *Biotechnology* 10:268).

Another method for physical delivery of DNA to plants is sonication of target cells as described in Zang, et al., (1991) *BioTechnology* 9:996. Alternatively, liposome or spheroplast fusions have been used to introduce expression vectors into plants. See, e.g., Deshayes, et al., (1985) *EMBO J.* 4:2731; and Christou, et al., (1987) *Proc. Natl. Acad. Sci. USA* 84:3962. Direct uptake of DNA into protoplasts using $CaCl_2$ precipitation, polyvinyl alcohol, or poly-L-ornithine has also been reported. See, e.g., Hain, et al., (1985) *Mol. Gen. Genet.* 199:161; and Draper, et al., (1982) *Plant Cell Physiol.* 23:451.

Electroporation of protoplasts and whole cells and tissues has also been described. See, e.g., Donn, et al., (1990) *Abstracts of the VIIth Int'l. Congress on Plant Cell and Tissue Culture IAPTC*, A2-38, p. 53; D'Halluin, et al., (1992) *Plant Cell* 4:1495-505; and Spencer, et al., (1994) *Plant Mol. Biol.* 24:51-61.

Increasing the Activity and/or Level of a NT Variant Polypeptide

Methods are provided to increase the activity and/or level of the NT variant polypeptide of the invention. An increase in the level and/or activity of the NT variant polypeptide of the invention can be achieved by providing to the plant a NT variant polypeptide. The NT variant polypeptide can be provided by introducing the amino acid sequence encoding the NT variant polypeptide into the plant, introducing into the plant a nucleotide sequence encoding a NT variant polypeptide or alternatively by modifying a genomic locus to insert a polynucleotide encoding the NT variant polypeptide of the invention.

As discussed elsewhere herein, many methods are known the art for providing a polypeptide to a plant including, but not limited to, direct introduction of the polypeptide into the plant, introducing into the plant (transiently or stably) a polynucleotide construct encoding a polypeptide of the present invention having increased NT activity. It is also recognized that the methods of the invention may employ a polynucleotide that is not capable of directing, in the transformed plant, the expression of a protein or an RNA. Thus, the level and/or activity of a NT variant polypeptide may be increased by altering the genome to encode a NT variant polypeptide.

Reducing the Activity and/or Level of a NT Polypeptide

Methods are provided o reduce or eliminate the activity of an enodgenous NT in plant cells, involving the use of NT polynucleotide or polypeptide variants in conjunction with, but not limited to, transgenic expression, antisense suppression, co-suppression, RNA interference, gene activation or suppression using transcription factors and/or repressors, mutagenesis including transposon tagging, directed and site-specific mutagenesis, chromosome engineering (see Nobrega et. al., Nature 431:988-993(04)), homologous recombination, and TILLING.

In accordance with the present invention, the expression of NT polypeptide is inhibited if the protein level of the NT polypeptide is less than 70% of the protein level of the same NT polypeptide in a plant that has not been genetically modified or mutagenized to inhibit the expression of that NT polypeptide. In particular embodiments of the invention, the protein level of the NT polypeptide in a modified plant according to the invention is less than 60%, less than 50%, less than 40%, less than 30%, less than 20%, less than 10%, less than 5%, or less than 2% of the protein level of the same NT polypeptide in a plant that is not a mutant or that has not been genetically modified to inhibit the expression of that NT polypeptide. The expression level of the NT polypeptide may be measured directly, for example, by assaying for the level of NT polypeptide expressed in the plant cell or plant, or indirectly, for example, by measuring the nitrogen uptake activity of the NT polypeptide in the plant cell or plant, or by measuring the phenotypic changes in the plant. Techniques and methods for performing such assays are described elsewhere herein and are familiar to one skilled in the art.

Methods for increasing the level and/or activity of NT polypeptides in a plant are discussed elsewhere herein. Briefly, such methods comprise providing a NT polypeptide of the invention to a plant and thereby increasing the level and/or activity of the NT variant polypeptide. In other embodiments, a NT variant nucleotide sequence encoding a NT variant polypeptide can be provided by introducing into the plant a polynucleotide comprising a NT variant nucleotide sequence of the invention, expressing the NT variant sequence, increasing the activity of the NT variant polypeptide, and thereby decreasing the number of tissue cells in the plant or plant part. In other embodiments, the NT variant nucleotide construct introduced into the plant is stably incorporated into the genome of the plant.

As discussed above, one of skill will recognize the appropriate promoter to use to modulate the level/activity of a NT in the plant. Exemplary promoters for this embodiment have been disclosed elsewhere herein.

In other embodiments, such plants have stably incorporated into their genome a nucleic acid molecule comprising a NT variant nucleotide sequence of the invention operably linked to a promoter that drives expression in the plant cell.

Modulating Root Development

Methods for modulating root development in a plant are provided. By "modulating root development" is intended any alteration in the development of the plant root when compared to a control plant. Such alterations in root development include, but are not limited to, alterations in the growth rate of the primary root, the fresh root weight, the extent of lateral and adventitious root formation, the vasculature system, meristem development, or radial expansion.

Methods for modulating root development in a plant are provided. The methods comprise modulating the level and/or activity of the NT variant polypeptide in the plant. In one method, a NT variant sequence of the invention is provided to the plant. In another method, the NT variant nucleotide sequence is provided by introducing into the plant a polynucleotide comprising a NT variant nucleotide sequence of the invention, expressing the NT variant sequence, and thereby modifying root development. In still other methods, the NT variant nucleotide construct introduced into the plant is stably incorporated into the genome of the plant.

In other methods, root development is modulated by altering the level or activity of the NT variant polypeptide in the plant. A change in NT activity can result in at least one or more of the following alterations to root development, including, but not limited to, alterations in root biomass and length.

As used herein, "root growth" encompasses all aspects of growth of the different parts that make up the root system at different stages of its development in both monocotyledonous and dicotyledonous plants. It is to be understood that enhanced root growth can result from enhanced growth of one or more of its parts including the primary root, lateral roots, adventitious roots, etc.

Methods of measuring such developmental alterations in the root system are known in the art. See, for example, U.S. Application No. 2003/0074698 and Werner, et al., (2001) *PNAS* 18:10487-10492, both of which are herein incorporated by reference.

As discussed above, one of skill will recognize the appropriate promoter to use to modulate root development in the plant. Exemplary promoters for this embodiment include constitutive promoters and root-preferred promoters. Exemplary root-preferred promoters have been disclosed elsewhere herein.

Furthermore, higher root biomass production due to NT activity has a direct effect on the yield and an indirect effect of production of compounds produced by root cells or transgenic root cells or cell cultures of said transgenic root cells. One example of an interesting compound produced in root cultures is shikonin, the yield of which can be advantageously enhanced by said methods.

Accordingly, the present invention further provides plants having modulated root development when compared to the root development of a control plant. In some embodiments, the plant of the invention has an increased level/activity of the NT variant polypeptide of the invention and has enhanced root growth and/or root biomass. In other embodiments, such plants have stably incorporated into their genome a nucleic acid molecule comprising a NT variant nucleotide sequence of the invention operably linked to a promoter that drives expression in the plant cell.

Modulating Shoot and Leaf Development

Methods are also provided for modulating shoot and leaf development in a plant. By "modulating shoot and/or leaf development" is intended any alteration in the development of the plant shoot and/or leaf. Such alterations in shoot and/or leaf development include, but are not limited to, alterations in shoot meristem development, in leaf number, leaf size, leaf and stem vasculature, internode length, and leaf senescence. As used herein, "leaf development" and "shoot development" encompasses all aspects of growth of the different parts that make up the leaf system and the shoot system, respectively, at different stages of their development, both in monocotyledonous and dicotyledonous plants. Methods for measuring such developmental alterations in the shoot and leaf system are known in the art. See, for example, Werner, et al., (2001) *PNAS* 98:10487-10492 and U.S. Application No. 2003/0074698, each of which is herein incorporated by reference.

The method for modulating shoot and/or leaf development in a plant comprises modulating the activity and/or level of a NT variant polypeptide of the invention. In one embodiment, a NT variant sequence of the invention is provided. In other embodiments, the NT variant nucleotide sequence can be provided by introducing into the plant a polynucleotide comprising a NT variant nucleotide sequence of the invention, expressing the NT variant sequence, and thereby modifying shoot and/or leaf development. In other embodiments, the NT variant nucleotide construct introduced into the plant is stably incorporated into the genome of the plant.

In specific embodiments, shoot or leaf development is modulated by altering the level and/or activity of the NT variant polypeptide in the plant. A change in NT activity can result in at least one or more of the following alterations in shoot and/or leaf development, including, but not limited to, changes in leaf number, altered leaf surface, altered vasculature, internodes and plant growth, and alterations in leaf senescence, when compared to a control plant.

As discussed above, one of skill will recognize the appropriate promoter to use to modulate shoot and leaf development of the plant. Exemplary promoters for this embodiment include constitutive promoters, shoot-preferred promoters, shoot meristem-preferred promoters, and leaf-preferred promoters. Exemplary promoters have been disclosed elsewhere herein.

Increasing NT activity and/or level in a plant may result in altered internodes and growth. Thus, the methods of the invention find use in producing modified plants. In addition, as discussed above, NT activity in the plant modulates both root and shoot growth. Thus, the present invention further provides methods for altering the root/shoot ratio. Shoot or leaf development can further be modulated by altering the level and/or activity of the NT variant polypeptide in the plant.

Accordingly, the present invention further provides plants having modulated shoot and/or leaf development when compared to a control plant. In some embodiments, the plant of the invention has an increased level/activity of the NT variant polypeptide of the invention. In other embodiments, the plant of the invention has a decreased level/activity of the NT variant polypeptide of the invention.

Modulating Reproductive Tissue Development

Methods for modulating reproductive tissue development are provided. In one embodiment, methods are provided to modulate floral development in a plant. By "modulating floral development" is intended any alteration in a structure of a plant's reproductive tissue as compared to a control plant in which the activity or level of the NT variant polypeptide has not been modulated. "Modulating floral development" further includes any alteration in the timing of the development of a plant's reproductive tissue (i.e., a delayed or a accelerated timing of floral development) when compared to a control plant in which the activity or level of the NT variant polypeptide has not been modulated. Macroscopic alterations may include changes in size, shape, number, or location of reproductive organs, the developmental time period that these structures form, or the ability to maintain or proceed through the flowering process in times of environmental stress. Microscopic alterations may include changes to the types or shapes of cells that make up the reproductive organs.

The method for modulating floral development in a plant comprises modulating NT activity in a plant. In one method, a NT variant sequence of the invention is provided. A NT variant nucleotide sequence can be provided by introducing into the plant a polynucleotide comprising a NT variant nucleotide sequence of the invention, expressing the NT variant sequence, and thereby modifying floral development. In other embodiments, the NT variant nucleotide construct introduced into the plant is stably incorporated into the genome of the plant.

In specific methods, floral development is modulated by increasing the level or activity of the NT variant polypeptide in the plant. A change in NT activity can result in at least one or more of the following alterations in floral development, including, but not limited to, altered flowering, changed number of flowers, modified male sterility, and altered seed set, when compared to a control plant. Inducing delayed flowering or inhibiting flowering can be used to enhance yield in forage crops such as alfalfa. Methods for measuring such developmental alterations in floral development are known in the art. See, for example, Mouradov, et al., (2002) *The Plant Cell* S111-S130, herein incorporated by reference.

As discussed above, one of skill will recognize the appropriate promoter to use to modulate floral development of the plant. Exemplary promoters for this embodiment include constitutive promoters, inducible promoters, shoot-preferred promoters, and inflorescence-preferred promoters.

In other methods, floral development is modulated by altering the level and/or activity of the NT variant sequence of the invention. Such methods can comprise introducing a NT variant nucleotide sequence into the plant and changing the activity of the NT variant polypeptide. In other methods, the NT variant nucleotide construct introduced into the plant is stably incorporated into the genome of the plant. Altering expression of the NT variant sequence of the invention can modulate floral development during periods of stress. Such methods are described elsewhere herein. Accordingly, the present invention further provides plants having modulated floral development when compared to the floral development of a control plant. Compositions include plants having a altered level/activity of the NT variant polypeptide of the invention and having an altered floral development. Compositions also include plants having a modified level/activity of the NT variant polypeptide of the invention wherein the plant maintains or proceeds through the flowering process in times of stress.

Methods are also provided for the use of the NT variant sequences of the invention to increase seed size and/or weight. The method comprises increasing the activity of the NT variant sequences in a plant or plant part, such as the seed. An increase in seed size and/or weight comprises an increased size or weight of the seed and/or an increase in the size or weight of one or more seed part including, for example, the embryo, endosperm, seed coat, aleurone, or cotyledon.

As discussed above, one of skill will recognize the appropriate promoter to use to increase seed size and/or seed weight. Exemplary promoters of this embodiment include constitutive promoters, inducible promoters, seed-preferred promoters, embryo-preferred promoters, and endosperm-preferred promoters.

The method for altering seed size and/or seed weight in a plant comprises increasing NT activity in the plant. In one embodiment, the NT variant nucleotide sequence can be provided by introducing into the plant a polynucleotide comprising a NT variant nucleotide sequence of the invention, expressing the NT variant sequence, and thereby decreasing seed weight and/or size. In other embodiments, the NT variant nucleotide construct introduced into the plant is stably incorporated into the genome of the plant.

It is further recognized that increasing seed size and/or weight can also be accompanied by an increase in the speed of growth of seedlings or an increase in early vigor. As used herein, the term "early vigor" refers to the ability of a plant to grow rapidly during early development, and relates to the successful establishment, after germination, of a well-developed root system and a well-developed photosynthetic apparatus. In addition, an increase in seed size and/or weight can also result in an increase in plant yield when compared to a control.

Accordingly, the present invention further provides plants having an increased seed weight and/or seed size when compared to a control plant. In other embodiments, plants having an increased vigor and plant yield are also provided. In some embodiments, the plant of the invention has a modified level/activity of the NT variant polypeptide of the invention and has an increased seed weight and/or seed size. In other embodiments, such plants have stably incorporated into their genome a nucleic acid molecule comprising a NT variant nucleotide sequence of the invention operably linked to a promoter that drives expression in the plant cell.

Method of Use for NT Variant Polynucleotide, Expression Cassettes, and Additional Polynucleotides In certain embodiments the nucleic acid sequences of the present invention can be stacked with any combination of polynucleotide sequences of interest in order to create plants with a desired phenotype. The combinations generated may include multiple copies of any one of the polynucleotides of interest. For example, a variant polynucleotide of the present invention may be stacked with any other variant polynucleotide(s) of the present invention. The variant polynucleotides of the present invention may be stacked with any gene or combination of genes to produce plants with a variety of desired trait combinations, including but not limited to traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,409); barley high lysine (Williamson, et al., (1987) *Eur. J. Biochem.* 165:99-106; and WO 98/20122); and high methionine proteins (Pedersen, et al., (1986) *J. Biol. Chem.* 261:6279; Kirihara, et al., (1988) *Gene* 71:359; and Musumura, et al., (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,737,514; 5,723,756; 5,593,881; Geiser, et al., (1986) *Gene* 48:109); lectins (Van Damme, et al., (1994) *Plant Mol. Biol.* 24:825); fumonisin detoxification genes (U.S. Pat. No. 5,792,931); avirulence and disease resistance genes (Jones, et al., (1994) *Science* 266:789; Martin, et al., (1993) *Science* 262:1432; Mindrinos, et al., (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert, et al., (1988) *J. Bacteriol.* 170:5837-5847) facilitate expression of polyhydroxyalkanoates (PHAs)), the disclosures of which are herein incorporated by reference. One could also combine the variant polynucleotides of the present invention with polynucleotides affecting agronomic traits such as male sterility (e.g., see U.S. Pat. No. 5,583,210), stalk strength, flowering time, or transformation technology traits such as cell cycle regulation or gene targeting (e.g., WO 99/61619; WO 00/17364; WO 99/25821), the disclosures of which are herein incorporated by reference.

In one embodiment, the variant polynucleotides of the present invention may be stacked with one or more polynucleotides that improve NUE, nitrate uptake, nitrogen assimilation, root biomass, or combinations thereof. Such polynucleotides include genes or the coding regions of, including but not limited to, nitrate transporters, nitrate reductases and/or root genes. Exemplary nitrate transporters include without limitation YNT1, optimized or partially optimized YNT1 and variants thereof, such as those disclosed herein. Exemplary nitrate reductases include without limitation YNR1 and PPNR A551G which are described elsewhere herein. Exemplary root genes include without limitation maize genomic clone of cytokinin oxidase/dehydrogenase gene (ZM-CKXg).

In one embodiment, sequences of interest improve plant growth and/or crop yields. For example, sequences of interest include agronomically important genes that result in improved primary or lateral root systems. Such genes include, but are not limited to, nutrient/water transporters and growth induces. Examples of such genes, include but are not limited to, maize plasma membrane $H^+$-ATPase (MHA2) (Frias, et al., (1996) *Plant Cell* 8:1533-44); AKT1, a component of the potassium uptake apparatus in *Arabidopsis*, (Spalding, et al., (1999) *J Gen Physiol* 113:909-18); RML genes which activate cell division cycle in the root apical cells (Cheng, et al., (1995) *Plant Physiol* 108:881); maize glutamine synthetase genes (Sukanya, et al., (1994) *Plant Mol Biol* 26:1935-46) and hemoglobin (Duff, et al., (1997) *J. Biol. Chem* 27:16749-16752, Arredondo-Peter, et al., (1997) *Plant Physiol.* 115:1259-1266; Arredondo-Peter, et al., (1997) *Plant Physiol* 114:493-500 and references sited therein). The sequence of interest may also be useful in expressing antisense nucleotide sequences of genes that that negatively affects root development.

Additional, agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson, et al., (1987) *Eur. J. Biochem.* 165:99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley, et al., (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen, et al., (1986) *J. Biol. Chem.* 261:6279; Kirihara, et al., (1988) *Gene* 71:359; both of which are herein incorporated by reference); and rice (Musumura, et al., (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser, et al., (1986) *Gene* 48:109); and the like.

Genes encoding disease resistance traits include detoxification genes, such as against fumonosin (U.S. Pat. No. 5,792,931); avirulence (avr) and disease resistance (R) genes (Jones, et al., (1994) *Science* 266:789; Martin, et al., (1993) *Science* 262:1432; and Mindrinos, et al., (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802, and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see, Schubert, et al., (1988) *J. Bacteriol.* 170:5837-5847) facilitate expression of polyhyroxyalkanoates (PHAs).

Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

Genes or coding sequences that are stacked with the NT variants described herein may be driven by any suitable promoter that expresses the polynucleotide in the desired temporal, spatial pattern and level within the plant or plant cell. Modification of gene expression in nitrate assimilation pathway, e.g. nitrate reductase and/or root genes along with NT may improve NUE more efficiently. Exemplary stacking constructs include but are not limited to the following set forth below:

TABLE 4

Exemplary stacking constructs.

| promoter | Coding sequence or gene of NT variant | Promoter for expression of stacked gene | Additional Coding sequence or gene | Promoter for expression of stacked gene | Additional Coding sequence or gene |
| --- | --- | --- | --- | --- | --- |
| ZM-RM2[1] ADHI Intron | An NT variant of the present invention | ZM-PEPC | PPNR A551G | | |
| ZM-RM2 ADHI Intron | An NT variant of the present invention | ZM-PEPC | PPNR A551G S561D MO | | |
| BSV (TR): ADHI Intron | An NT variant of the present invention | ZM-PEPC | PPNR A551G | | |

TABLE 4-continued

Exemplary stacking constructs.

| promoter | Coding sequence or gene of NT variant | Promoter for expression of stacked gene | Additional Coding sequence or gene | Promoter for expression of stacked gene | Additional Coding sequence or gene |
|---|---|---|---|---|---|
| ZM-RM2: ADHI Intron | An NT variant of the present invention | BSV (TR): ADHI Intron | ZM-CKXg | ZM-PEPC | PPNR A551G |

Figure 7A:
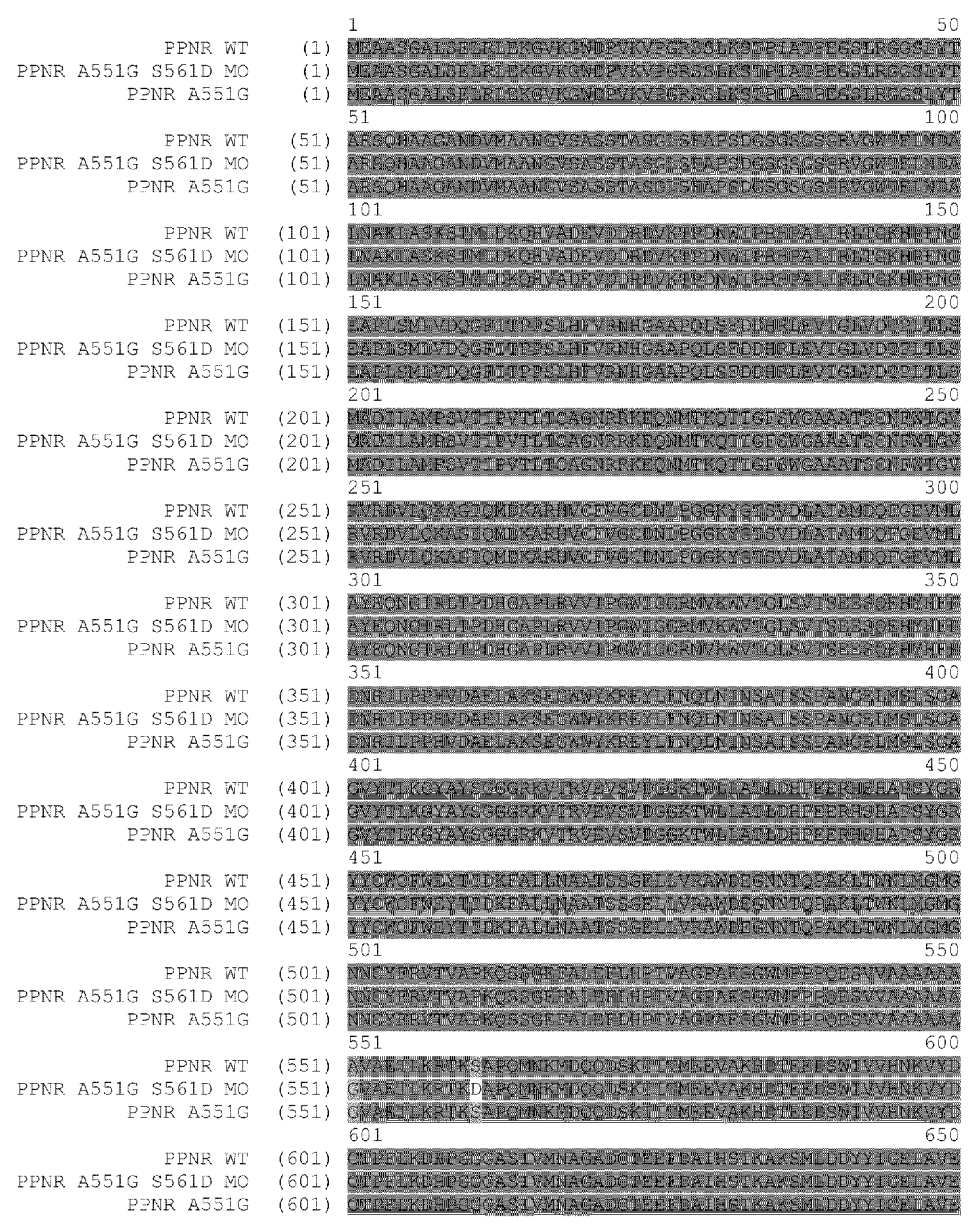
Figure 7B:
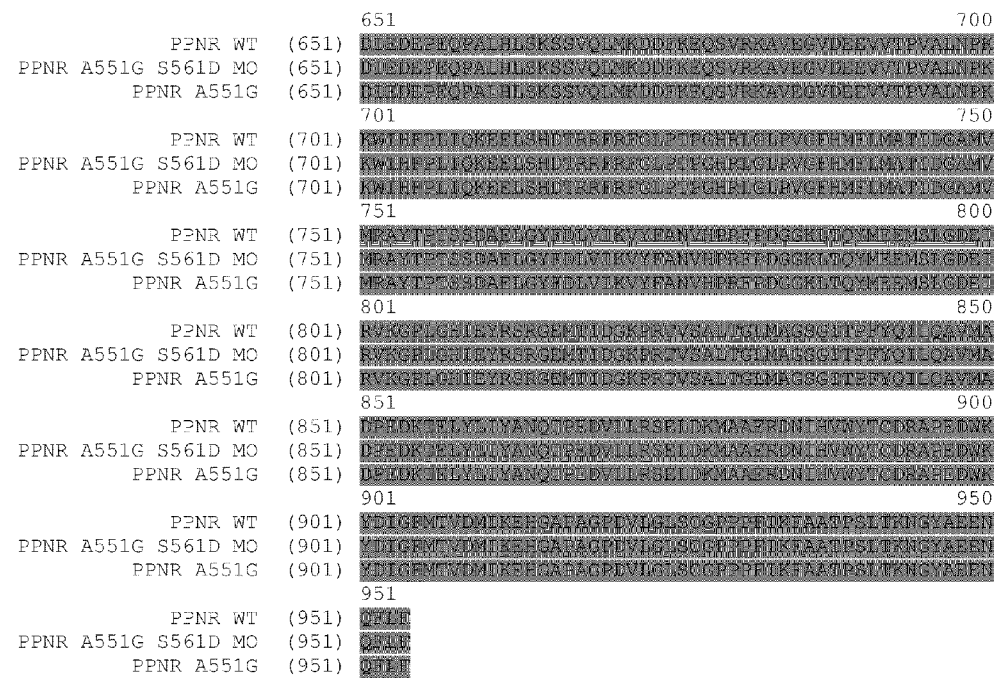

[1]Maize root metallothionein promoter = ZM-RM2; maize NAS2 promoter, banana streak virus promoter truncated version promoter = BSV (TR), maize phosphoenolpyruvate carboxylase promoter = ZM-PEPC; maize ubiquitin promoter = UBI (maize ubiquitin promoter (Christensen et al., *Plant Mol. Biol.* 12: 619-632 (1989) and Christensen et al., Plant Mol. Biol. 18: 675-689 (1992)); ADHI Intron = Intron of alcohol dehydrogenase 1 gene; maize genomic clone of cytokinin oxidase/dehydrogenase gene = ZM-CKXg; PPNR A551G, also referred to as A7G PPNR = wild type red algae nitrate reductase (*Porphyra perforata*) wherein the seventh alanine in the putative allergen site of wild type PPNR has been substituted with a glycine amino acid at position 551; PPNR A551G S561D MO = maize codon optimized wild type red algae nitrate reductase (*Porphyra perforata*) wherein the seventh alanine in the putative allergen site of wild type PPNR has been substituted with a glycine amino acid at position 551 and the serine residue at position 561 has been substituted with aspartic acid amino acid to knock out the putative phosphorylation site. See FIGS. 6 and 7. Wild type PPNR contains a putative allergen peptide with 8 aa residues, Val followed by 7 Alas, Val Ala1 Ala2 Ala3 Ala4 Ala5 Ala6 Ala7. See FIG. 7. In a preferred embodiment, the construct includes YNT1R3FS stacked with a nitrate reductase gene of PPNR A551G.

The PPNR A551G or A7G PPNR and PPNR A551G S561D MO have "NR activity" which refers to an activity exerted by a nitrate reductase (NR) protein, polypeptide or portion thereof as determined in vivo, or in vitro, according to standard techniques. In one aspect, NR activity is the reduction of nitrate to nitrite. In one aspect, NR activity includes but is not limited to increased nitrate reduction rate and/or specificity for nitrate, for example, decreased $K_m$ for nitrate and NADH, increased velocity ($V_{max}$) for nitrate reduction and the like as compared to NR activity of an endogenous NR of a crop plant of interest. In another aspect, NR activity includes but is not limited to increasing NUE and/or plant productivity/yield as compared to a control plant. NUE may be inferred from amount and/or rate of nitrogen uptake from the soil or medium. In another aspect, NR activity includes but is not limited to maintaining NR activity, for example, as compared to a wild type NR, while inactivating post-translational regulation by knocking out the putative serine residue, e.g. Ser 561 of PPNR when consumed as compared to a control plant, e.g. expressing a wild type NR. Methods and techniques for testing for NR activity will be known to one skilled in the art and are also described in U.S. patent application Ser. No. 12/138,477, filed Jun. 13, 2008, herein incorporated by reference in its entirety.

The polynucleotides of the present invention can be used in the transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean and sugarcane plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

This invention can be better understood by reference to the following non-limiting examples. It will be appreciated by those skilled in the art that other embodiments of the invention may be practiced without departing from the spirit and the scope of the invention as herein disclosed and claimed.

The present invention is further defined in the following Examples, in which parts and percentages are by weight and degrees are Celsius, unless otherwise stated. The disclosure of each reference set forth herein is incorporated herein by reference in its entirety.

EXAMPLES

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

Example 1

Cloning of Yeast Nitrate Transporter (YNT1) Coding Sequence from *Pichia angusta* and Test its Functionality in *Pichia pastoris*

PCR was used to obtain the coding sequence of YNT1 gene from *Pichia angusta* genomic DNA based on the published data (Perez M D et al., *Biochem. J.*, (1997) 15:397-403) with BamH I and EcoRI restriction sites at the respective 5'- and 3' ends. The fragment was cloned into pCR-Blunt TOPO vector for sequencing. The functionality of YNT1 was verified using *Pichia pastoris* system developed at Pioneer Hi-Bred Int'l (U.S. patent application Ser. No. 12/136,173). The clone with correct sequence was used to make yeast expression vector pGAPZA-YNT1 via BamHI and EcoRI sites. *Pichia pastoris* strain KM71 (Invitrogen) carrying p3.5GAP-YNR1 (yeast nitrate reductase driven by pGAP promoter integrated into His4 locus) was transformed by pGAPZA-YNT1 via integration into the pGAP promoter region to generate KM71 strain carrying both YNT1 and YNR1 gene expression cassettes. Functional transformants were identified by nitrate uptake assay in vivo (U.S. patent application Ser. No. 12/136,173).

Example 2

YNT1 DNA Shuffling and Functional Screen in *Pichia pastoris*

Multiple rounds of YNT1 shuffled libraries were constructed by incorporating oligo spiked diversities from existing fungal and plant high affinity nitrate transporter genes. The expression of the wild type and shuffled YNT1 variants were under control of a *P. pastoris* promoter (pYPT). (GenBank accession # AF027960.) The shuffled libraries were transformed into a *P. pastoris* host in which a YNR (*P. angusta* nitrate reductase) was expressed. (GenBank accession# Z49110) Incorporation of YNR will allow nitrate to be converted into Nitrite. Nitrite can be quantified by a colorimetric assay called the Griess reaction. Variants from the shuffled libraries were screened for enhanced nitrate uptake activities of whole cell suspension using the Griess reaction. By three rounds of shuffling and screening, we identified several variants with significantly enhanced nitrate uptake activities (up to 5x, see FIG. 5).

Nitrate uptake kinetic comparison among wt and shuffled Nt variants—*Pichia* transformants of wt NT and four shuffled NT variants were grown in a minimal medium (MD:1.34% yeast nitrogen base from Qbiogen and 2% glucose and $4 \times 10^{-5}$% biotin) for over night at 30° C. The yeast cells were washed twice with water and resuspended in 20 mM MOPS (3-(N-morpholino) propanesulfonic acid), 1% glucose pH 6.5 at one half the original culture volume. Cell densities were normalized based their optical density at 600 nm. Uptake assays were performed in a 96-well v-bottom plate by combining 50 □L of suspended cells with 50 □L of sodium nitrate solution (prepared with the abovementioned MOPS buffer) and incubated with shaking at room temperature for 30 min or longer. Nitrite concentration was determined by the Griess Reagent Kit from Promega (Madison, Mich.) following the manufacture's instruction. The optical density at 545 nm of the final reaction was measured using the UV-max plate spectrophotometer (Molecular Device, Sunnyvale, Calif.).)

Example 3

YNT1R3FS Coding Sequence Modification for Maize Expression

To enhance the expression potential in maize, the codon of one of the variant YNT1R3FS coding sequence was optimized. The rare codons were eliminated. The GC composition was targeted to be less than 60%, preferably 54-58% and distributed relative flat over the length of the ORF. At same time, several unwanted features including cryptic intron donor or acceptor sites, RNA instability sites, long homogenous base stretches, and undesired restriction enzymes were removed. The sequence of maize codon optimized YNT1R3FS (YNT1R3FS MO) is set forth in SEQ ID NO:9. Briefly, a maize expression constructs of YNT1R3FS MO driven by root-preferred promoter, e.g. ZM-RM2 promoter and BSV (TR) promoter was prepared by standard cloning techniques.

Example 4

Preparation of a Plant Expression Vector

Two expression vectors for each YNT1 variant driven by maize ZM-RM2 promoter without ADHI Intron (weaker promoter) and with ADHI Intron (stronger promoter) were generated for elite maize line transformation. They are PHP32096, 32097, 32098, 32099, 32101, 32103, 3210373, and 32374. More constructs of YNT1R3FS driven by different promoters were generated for maize transformation. They are PHP40510 (BSV (TR):ADHI Intron:YNT1R3FS) and PHP (BAV (FL):YNT1R3FS).

Several constructs containing YNTR3FS MO were also generated for maize transformation. They are PHP35503 (ZM-RM2:ADHI Intron:YNT1R3FS), PHP40509 (BSV (TR):ADHI Intron:YNT1R3FS), and new PHP (BAV (FL): YNT1R3FS). Stacking constructs including nitrate transporter gene YNT1R3FS and nitrate reductase gene PPNR A551G to improve nitrate uptake and assimilation will be made for elite line transformation to approve the concept.

Example 5

Agrobacterium Mediated Transformation of Maize with NTs

Agrobacterium-mediated transformation of maize is performed essentially as described by Zhao et al., in *Meth. Mol. Biol.* 318:315-323 (2006) (see also Zhao et al., *Mol. Breed.* 8:323-333 (2001) and U.S. Pat. No. 5,981,840 issued Nov. 9, 1999, incorporated herein by reference). The transformation process involves bacterium inoculation, co-cultivation, resting, selection and plant regeneration.

1. Immature Embryo Preparation

Immature embryos are dissected from caryopses and placed in a 2 mL microtube containing 2 mL PHI-A medium.

2. Agrobacterium Infection and Co-Cultivation of Embryos 2.1 Infection Step

PHI-A medium is removed with 1 mL micropipettor and 1 mL Agrobacterium suspension is added. Tube is gently inverted to mix. The mixture is incubated for 5 min at room temperature.

2.2 Co-Culture Step

The Agrobacterium suspension is removed from the infection step with a 1 mL micropipettor. Using a sterile spatula the embryos are scraped from the tube and transferred to a plate of PHI-B medium in a 100×15 mm Petri dish. The embryos are oriented with the embryonic axis down on the surface of the medium. Plates with the embryos are cultured at 20° C., in darkness, for 3 days. L-Cysteine can be used in the co-cultivation phase. With the standard binary vector, the co-cultivation medium supplied with 100-400 mg/L L-cysteine is critical for recovering stable transgenic events.

3. Selection of Putative Transgenic Events

To each plate of PHI-D medium in a 100×15 mm Petri dish, 10 embryos are transferred, maintaining orientation and the dishes are sealed with Parafilm. The plates are incubated in darkness at 28° C. Actively growing putative events, as pale yellow embryonic tissue are expected to be visible in 6-8 weeks. Embryos that produce no events may be brown and necrotic, and little friable tissue growth is evident. Putative transgenic embryonic tissue is subcultured to fresh PHI-D plates at 2-3 week intervals, depending on growth rate. The events are recorded.

4. Regeneration of T0 Plants

Embryonic tissue propagated on PHI-D medium is subcultured to PHI-E medium (somatic embryo maturation medium); in 100×25 mm Petri dishes and incubated at 28° C., in darkness, until somatic embryos mature, for about 10-18 days. Individual, matured somatic embryos with well-defined scutellum and coleoptile are transferred to PHI-F embryo germination medium and incubated at 28° C. in the light (about 80 µE from cool white or equivalent fluorescent lamps). In 7-10 days, regenerated plants, about 10 cm tall, are potted in horticultural mix and hardened-off using standard horticultural methods.

Media for Plant Transformation

1. PHI-A: 4 g/L CHU basal salts, 1.0 mL/L 1000× Eriksson's vitamin mix, 0.5 mg/L thiamin HCL, 1.5 mg/L 2,4-D, 0.69 g/L L-proline, 68.5 g/L sucrose, 36 g/L glucose, pH 5.2. Add 100 µM acetosyringone, filter-sterilized before using.
2. PHI-B: PHI-A without glucose, increased 2,4-D to 2 mg/L, reduced sucrose to 30 g/L and supplemented with 0.85 mg/L silver nitrate (filter-sterilized), 3.0 g/L gelrite, 100 µM acetosyringone (filter-sterilized), 5.8.
3. PHI-C: PHI-B without gelrite and acetosyringone, reduced 2,4-D to 1.5 mg/L and supplemented with 8.0 g/L agar, 0.5 g/L Ms-morpholino ethane sulfonic acid (MES) buffer, 100 mg/L carbenicillin (filter-sterilized).
4. PHI-D: PHI-C supplemented with 3 mg/L bialaphos (filter-sterilized).
5. PHI-E: 4.3 g/L of Murashige and Skoog (MS) salts, (Gibco, BRL 11117-074), 0.5 mg/L nicotinic acid, 0.1 mg/L thiamine HCl, 0.5 mg/L pyridoxine HCl, 2.0 mg/L glycine, 0.1 g/L myo-inositol, 0.5 mg/L zeatin (Sigma, cat. no. Z-0164), 1 mg/L indole acetic acid (IAA), 26.4 µg/L abscisic acid (ABA), 60 g/L sucrose, 3 mg/L bialaphos (filter-sterilized), 100 mg/L carbenicillin (filter-sterilized), 8 g/L agar, pH 5.6.
6. PHI-F: PHI-E without zeatin, IAA, ABA; sucrose reduced to 40 g/L; replacing agar with 1.5 g/L gelrite; pH 5.6.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839). Phenotypic analysis of transgenic T0 plants and T1 plants can be performed.

T1 plants can be analyzed for phenotypic changes. Using image analysis T1 plants can be analyzed for phenotypical changes in plant area, volume, growth rate and color analysis can be taken at multiple times during growth of the plants. Alteration in root architecture can be assayed as described herein.

Subsequent analysis of alterations in agronomic characteristics can be done to determine whether plants containing a NT variant polynucleotide described herein have an improvement of at least one agronomic characteristic, when compared to the control (or reference) plants that do not contain the NT variant polynucleotide. The alterations may also be studied under various environmental conditions.

Expression constructs containing the NT variant polynucleotide that result in a significant alteration in root and/or shoot biomass, improved green color, larger ear at anthesis or yield will be considered evidence that the NT variant polynucleotide functions in maize to alter nitrogen use efficiency or nitrate uptake.

Example 6

Transformation of Maize with NTs Using Particle Bombardment (Prophetic)

Maize plants can be transformed to express or overexpress a NT variant polynucleotide described herein in order to examine the resulting phenotype.

Expression of the gene in maize can be under control of a constitutive promoter such as the maize ubiquitin promoter (Christensen et al., *Plant Mol. Biol.* 12:619-632 (1989) and Christensen et al., *Plant Mol. Biol.* 18:675-689 (1992))

The recombinant DNA construct described above can then be introduced into maize cells by the following procedure. Immature maize embryos can be dissected from developing caryopses derived from crosses of the inbred maize lines H99 and LH132. The embryos are isolated ten to eleven days after pollination when they are 1.0 to 1.5 mm long. The embryos are then placed with the axis-side facing down and in contact with agarose-solidified N6 medium (Chu et al., *Sci. Sin. Peking* 18:659-668 (1975)). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every two to three weeks.

The plasmid, p35S/Ac (obtained from Dr. Peter Eckes, Hoechst Ag, Frankfurt, Germany) may be used in transformation experiments in order to provide for a selectable marker. This plasmid contains the pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from cauliflower mosaic virus (Odell et al., Nature 313:810-812 (1985)) and the 3' region of the nopaline synthase gene from the T-DNA of the Ti plasmid of Agrobacterium tumefaciens.

The particle bombardment method (Klein et al., Nature 327:70-73 (1987)) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After ten minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the maize tissue with a Biolistic® PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialaphos (5 mg per liter) and lacks casein or proline. The tissue continues to grow slowly on this medium. After an additional two weeks the tissue can be transferred to fresh N6 medium containing bialaphos. After six weeks, areas of about 1 cm in diameter of actively growing callus can be identified on some of the plates containing the bialaphos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., Bio/Technology 8:833-839 (1990)). Transgenic T0 plants can be regenerated and their phenotype determined following HTP procedures. T1 seed can be collected.

T1 plants can be grown and analyzed for phenotypic changes. The following parameters can be quantified using image analysis: plant area, volume, growth rate and color analysis can be collected and quantified. Expression constructs that result in an alteration of root architecture or any one of the agronomic characteristics listed above compared to suitable control plants, can be considered evidence that the NT variant polynucleotide functions in maize to alter root architecture or plant architecture.

Furthermore, a recombinant DNA construct containing a NT variant polynucleotide described herein can be introduced into an maize line either by direct transformation or introgression from a separately transformed line.

Transgenic plants, either inbred or hybrid, can undergo more vigorous field-based experiments to study root or plant architecture, yield enhancement and/or resistance to root lodging under various environmental conditions (e.g. variations in nutrient and water availability).

Subsequent yield analysis can also be done to determine whether plants that contain the NT variant polynucleotide have an improvement in yield performance, when compared to the control (or reference) plants that do not contain the NT variant polynucleotide. Plants containing the NT variant polynucleotide would improved yield relative to the control plants, preferably 50% less yield loss under adverse environmental conditions or would have increased yield relative to the control plants under varying environmental conditions.

Example 7

Electroporation of *Agrobacterium tumefaciens* LBA4404 (Prophetic)

Electroporation competent cells (40 μl), such as *Agrobacterium tumefaciens* LBA4404 (containing PHP10523), are thawn on ice (20-30 min). PHP10523 contains VIR genes for T-DNA transfer, an *Agrobacterium* low copy number plasmid origin of replication, a tetracycline resistance gene, and a cos site for in vivo DNA biomolecular recombination. Meanwhile the electroporation cuvette is chilled on ice. The electroporator settings are adjusted to 2.1 kV.

A DNA aliquot (0.5 μL JT (U.S. Pat. No. 7,087,812) parental DNA at a concentration of 0.2 μg-1.0 μg in low salt buffer or twice distilled $H_2O$) is mixed with the thawn *Agrobacterium* cells while still on ice. The mix is transferred to the bottom of electroporation cuvette and kept at rest on ice for 1-2 min. The cells are electroporated (Eppendorf electroporator 2510) by pushing "Pulse" button twice (ideally achieving a 4.0 msec pulse). Subsequently 0.5 ml 2×YT medium (or SOC medium) are added to cuvette and transferred to a 15 ml Falcon tube. The cells are incubated at 28-30° C., 200-250 rpm for 3 h.

Aliquots of 250 μl are spread onto #30B (YM+50 μg/mL Spectinomycin) plates and incubated 3 days at 28-30° C. To increase the number of transformants one of two optional steps can be performed:

Option 1: overlay plates with 30 μl of 15 mg/ml Rifampicin. LBA4404 has a chromosomal resistance gene for Rifampicin. This additional selection eliminates some contaminating colonies observed when using poorer preparations of LBA4404 competent cells.

Option 2: Perform two replicates of the electroporation to compensate for poorer electrocompetent cells.

Identification of Transformants:

Four independent colonies are picked and streaked on AB minimal medium plus 50 mg/mL Spectinomycin plates (#12S medium) for isolation of single colonies. The plated are incubate at 28° C. for 2-3 days.

A single colony for each putative co-integrate is picked and inoculated with 4 ml #60A with 50 mg/l Spectinomycin. The mix is incubated for 24 h at 28° C. with shaking Plasmid DNA from 4 ml of culture is isolated using Qiagen Miniprep+ optional PB wash. The DNA is eluted in 30 µl. Aliquots of 2 µl are used to electroporate 20 µl of DH10b+20 µl of ddH$_2$O as per above.

Optionally a 15 µl aliquot can be used to transform 75-100 µl of Invitrogen™-Library Efficiency DH5α. The cells are spread on LB medium plus 50 mg/mL Spectinomycin plates (#34T medium) and incubated at 37° C. overnight.

Three to four independent colonies are picked for each putative co-integrate and inoculated 4 ml of 2×YT (#60A) with 50 µg/ml Spectinomycin. The cells are incubated at 37° C. overnight with shaking.

The plasmid DNA is isolated from 4 ml of culture using QIAprep® Miniprep with optional PB wash (elute in 50 µl) and 8 µl are used for digestion with SalI (using JT parent and PHP10523 as controls). Three more digestions using restriction enzymes BamHI, EcoRI, and HindIII are performed for 4 plasmids that represent 2 putative co-integrates with correct SalI digestion pattern (using parental DNA and PHP10523 as controls). Electronic gels are recommended for comparison.

Example 8

Transgenic Plants Evaluation Using Uptake Assay in *Arabidopsis*

Wt and shuffled YNT variants were cloned into *Arabidopsis* expression vector (pMAXY5295) under the control of pTUB promoter, a root preferred *Arabidopsis* promoter. Following the standard *agrobacterium* transformation, multiple events were recovered.

Briefly, the construct containing pTUB:YNT1 was transformed into *Agrobacterium tumefaciens* strain C58, grown in LB at 25° C. to OD600~1.0. Cells were then pelleted by centrifugation and resuspended in an equal volume of 5% sucrose/0.05% Silwet L-77 (OSI Specialties, Inc). At early bolting, soil grown *Arabidopsis thaliana* ecotype Col-0 were dipped into the *Agrobacterium* suspension. The plants were then allowed to set seed as normal. The resulting T$_1$ seed were sown on soil, and transgenic seedlings were selected by growing T1 seeds on medium with Kanamycin. The resistant seedlings were transplanted into soil. T2 seeds were collected from T1 plates resistant to Kanamycin selection. T$_2$ seed was collected, The presence of the transgene was analyzed by RT-PCR and Western-blot analysis. Using the protocol detailed in U.S. patent application Ser. No. 12/166,473, filed Jul. 3, 2007, a pH-dye based nitrate uptake seedling assay was performed for those transformant events. Multiple events (3 out of 8) from pTUB-YNT1-R3FS construct demonstrated statistically significant enhancement in nitrate uptake when compared with nitrate uptake of the wild type YNT construct.

Example 9

Low Nitrate Assay in GS3×Gaspe to Determine Shoot and Ear Dry Weight (Prophetic)

Transgenic plants will contain two or three doses of Gaspe Flint-3 with one dose of GS3 (GS3/(Gaspe-3)2× or GS3/(Gaspe-3)3×) and segregate 1:1 for a dominant transgene.

Transgenic GS3×Gaspe T1 seeds will be planted in 4 inch pots containing Turface and watered with nutrient solution (Table 5) containing 1 mM nitrate as the sole nitrogen source for 2 weeks.

TABLE 5

| Nutrient Solution | |
|---|---|
| Nutrient | Concentration |
| KNO$_3$ | 1 mM |
| KCl | 3 mM |
| MgSO$_4$ | 2 mM |
| CaCl$_2$ | 2 mM |
| KH$_2$PO$_4$ | 0.5 mM |
| Chelated Iron | 8.3 g 1001$^{-1}$ |
| MnSO$_4$ | 0.5 µM |
| ZnSO$_4$ | 0.5 µM |
| H$_3$BO$_4$ | 1.5 µM |
| CuSO$_4$ | 0.05 µM |
| H$_2$MoO$_4$ | 0.05 µM |

Three transgenes of PHP32103 (ZM-RM2:ADHI Intron: YNT1R3LS variant), PHP32097 (ZM-RM2:YNT1R2C7 variant), and PHP32099 (ZM-RM2:YNT1R3LS variant) and their respective nulls will be grown in each block. Please indicate which of these variants corresponds with the above PHPnumbers: YNT1-R2AL, YNT1R2C7, YNT1R3FS, or YNT1R3LS.

The nutrients will be replaced 4 times each day to maintain a constant concentration of nutrients. After emergence plants will be sampled to determine which are transgenic and which are nulls. At anthesis plants will be harvested and dried in a 70° C. oven for 72 hr and the shoot and ear dry weight determined. Transgene means will be calculated and compared to the grand mean, the block mean and their respective null means (see Table 6 below). Control plants grown in 1 mM KNO$_3$ medium. Statistical analysis will be performed to determine if observed differences between treatments are significant. Improvements in biomass and ear size at anthesis is indicative of increased nitrogen tolerance.

Example 10

Green House Low Nitrate Assay to Determine Root Dry Weight, Shoot Dry Weight, Root/Shoot Ratio, Total Plant Weight, Total N Concentration and Total Plant N Transgenic T1/T2 Plants were grown in nutrient medium (Table 5) containing 1 mM nitrate as the sole nitrogen source for 2 weeks. After 2 weeks the plants were harvested and root dry weight, shoot dry weight, root/shoot ratio, total plant weight, total N concentration and total plant N determined. Data was analyzed using a nearest neighbor analysis to estimate the variance. Transgenic means were compared to the experiment grand mean, to the block mean after the mean in question was removed from the block mean estimate, and to the corresponding transgenic null mean. Table 6-8 shows the Student's t probability comparing the transgenic means to the corresponding null means. Any mean with a Student's t probability 0.1 or less is listed in the table and any values with a Student's t probability greater than 0.1 are listed as non significant (NS). Student's t probabilities of transgene means greater than the null means are designated with an asterisk (*). The data from PHP32103 (ZM-RM2:ADHI Intron: YNT1R3LS variant), PHP32097 (ZM-RM2:YNT1R2C7 variant), and PHP32099 (ZM-RM2:YNT1R3LS variant), are summarized here:

TABLE 6

GH LN assay PHP32103

| Event | Root Dwt | Root Dwt Null | Sig Level | Shoot Dwt | Shoot Dwt Null | Sig Level | Total Dwt | Total Dwt Null | Sig Level |
|---|---|---|---|---|---|---|---|---|---|
| 1 | 1 | 0.9 | <0.001* | 2.1 | 1.83 | <0.001* | 3.11 | 2.73 | <0.001* |
| 2 | 0.86 | 0.9 | 0.03 | 1.82 | 1.83 | NS | 2.68 | 2.73 | NS |
| 3 | 0.85 | 0.9 | 0.01 | 1.68 | 1.83 | 0.01 | 2.52 | 2.73 | 0.01 |
| 4 | 0.88 | 0.9 | NS | 1.81 | 1.83 | NS | 2.69 | 2.73 | NS |
| 5 | 0.84 | 0.9 | 0.00 | 1.72 | 1.83 | 0.04 | 2.56 | 2.73 | 0.02 |
| 6 | 1.06 | 0.9 | <0.001* | 2.19 | 1.83 | <0.001* | 3.25 | 2.73 | <0.001* |
| 7 | 0.93 | 0.9 | NS | 2.01 | 1.83 | 0.002* | 2.94 | 2.73 | 0.006* |
| 8 | 1.01 | 0.9 | <0.001* | 2.04 | 1.83 | <0.001* | 3.04 | 2.73 | <0.001* |
| 9 | 0.95 | 0.9 | 0.030* | 1.84 | 1.83 | NS | 2.79 | 2.73 | NS |
| 10 | 0.96 | 0.9 | 0.014* | 1.79 | 1.83 | NS | 2.75 | 2.73 | NS |

| Event | Root/ Shoot | Root/ Shoot Null | Sig Level | mg N/g Dwt | mg N/g Dwt Null | Sig Level | Total N (mg) | Total N (mg) Null | Sig Level |
|---|---|---|---|---|---|---|---|---|---|
| 1 | 0.4796 | 0.4997 | 0.03 | 26.5260 | 26.8480 | NS | 81.726 | 73.085 | <0.001* |
| 2 | 0.4741 | 0.4997 | 0.01 | 27.0310 | 26.8480 | NS | 71.436 | 73.085 | NS |
| 3 | 0.5147 | 0.4997 | 0.084* | 26.5140 | 26.8480 | NS | 64.2 | 73.085 | <0.001 |
| 4 | 0.4933 | 0.4997 | NS | 25.5620 | 26.8480 | 0.03 | 68.926 | 73.085 | 0.04 |
| 5 | 0.4996 | 0.4997 | NS | 26.3670 | 26.8480 | NS | 67.035 | 73.085 | 0.01 |
| 6 | 0.4876 | 0.4997 | NS | 24.6030 | 26.8480 | <0.001 | 79.924 | 73.085 | 0.003* |
| 7 | 0.4632 | 0.4997 | <0.001 | 26.9510 | 26.8480 | NS | 79.147 | 73.085 | 0.007* |
| 8 | 0.5004 | 0.4997 | NS | 25.7730 | 26.8480 | 0.06 | 77.872 | 73.085 | 0.024* |
| 9 | 0.5237 | 0.4997 | 0.014* | 23.0590 | 26.8480 | <0.001 | 64.524 | 73.085 | <0.001 |
| 10 | 0.5398 | 0.4997 | <0.001* | 25.5780 | 26.8480 | 0.04 | 70.227 | 73.085 | NS |

TABLE 7

GH LN assay PHP32097

| Event | Root Dwt | Root Dwt Null | Sig Level | Shoot Dwt | Shoot Dwt Null | Sig Level | Total Dwt | Total Dwt Null | Sig Level |
|---|---|---|---|---|---|---|---|---|---|
| 1 | 1.28 | 1.28 | NS | 3.04 | 3.42 | 0.01 | 4.32 | 4.7 | 0.03 |
| 2 | 1.42 | 1.28 | 0.048* | 3.37 | 3.42 | NS | 4.78 | 4.7 | NS |
| 3 | 1.44 | 1.28 | 0.022* | 3.56 | 3.42 | NS | 5 | 4.7 | 0.072* |
| 4 | 1.24 | 1.28 | NS | 3.01 | 3.42 | 0.01 | 4.25 | 4.7 | 0.02 |
| 5 | 1.44 | 1.28 | 0.019* | 3.51 | 3.42 | NS | 4.95 | 4.7 | NS |

| Event | Root/ Shoot | Root/ Shoot Null | Sig Level | mg N/g Dwt | mg N/g Dwt Null | Sig Level | Total N (mg) | Total N (mg) Null | Sig Level |
|---|---|---|---|---|---|---|---|---|---|
| 1 | 0.4241 | 0.3768 | 0.002* | 18.7460 | 17.2690 | 0.053* | 79.0706 | 80.2608 | NS |
| 2 | 0.4222 | 0.3768 | 0.005* | 18.4030 | 17.2690 | NS | 86.3902 | 80.2608 | 0.010* |
| 3 | 0.4027 | 0.3768 | 0.055* | 16.1310 | 17.2690 | NS | 80.3801 | 80.2608 | NS |
| 4 | 0.3943 | 0.3768 | NS | 20.5070 | 17.2690 | 0.001* | 77.5006 | 80.2608 | NS |
| 5 | 0.4102 | 0.3768 | 0.021* | 17.3260 | 17.2690 | NS | 84.4969 | 80.2608 | 0.040* |

TABLE 8

GH LN assay PHP32099

| Event | Root Dwt | Root Dwt Null | Sig Level | Shoot Dwt | Shoot Dwt Null | Sig Level | Total Dwt | Total Dwt Null | Sig Level |
|---|---|---|---|---|---|---|---|---|---|
| 1 | 1.49 | 1.35 | 0.070* | 3.54 | 2.95 | <0.001* | 5.04 | 4.3 | <0.001* |
| 2 | 1.22 | 1.35 | NS | 2.97 | 2.95 | NS | 4.19 | 4.3 | NS |
| 3 | 1.5 | 1.35 | 0.065* | 3.29 | 2.95 | 0.015* | 4.79 | 4.3 | 0.018* |
| 4 | 1.77 | 1.35 | <0.001* | 3.42 | 2.95 | 0.001* | 5.19 | 4.3 | <0.001* |
| 5 | 1.25 | 1.35 | NS | 3.23 | 2.95 | 0.036* | 4.49 | 4.3 | NS |

| Event | Root/ Shoot | Root/ Shoot Null | Sig Level | mg N/g Dwt | mg N/g Dwt Null | Sig Level | Total N (mg) | Total N (mg) Null | Sig Level |
|---|---|---|---|---|---|---|---|---|---|
| 1 | 0.4215 | 0.4446 | NS | 17.1320 | 18.0500 | NS | 85.8591 | 73.3276 | <0.001* |
| 2 | 0.4008 | 0.4446 | 0.05 | 19.4960 | 18.0500 | 0.050* | 77.6323 | 73.3276 | 0.057* |
| 3 | 0.4552 | 0.4446 | NS | 16.0420 | 18.0500 | 0.01 | 76.2291 | 73.3276 | NS |

TABLE 8-continued

GH LN assay PHP32099

| 4 | 0.5369 | 0.4446 | <0.001* | 16.0480 | 18.0500 | 0.01 | 81.224 | 73.3276 | 0.002* |
| 5 | 0.3849 | 0.4446 | 0.02 | 19.1440 | 18.0500 | NS | 82.5614 | 73.3276 | <0.001* |

Example 11

Field Trails Under Nitrogen Stress and Normal Nitrogen Conditions to Determine Grain Yield, Flowering Time, and Staygreen of Events Containing the NT Variant Transgene Corn hybrids containing the transgene were planted in the field under nitrogen stress and normal nitrogen conditions at three locations. Under normal nitrogen, a total of 250 lbs nitrogen was applied in the form of urea ammonium nitrate (UAN). Nitrogen stress was achieved through depletion of soil nitrogen reserves by planting corn with no added nitrogen for two years. Soil nitrate reserves were monitored to assess the level of depletion. To achieve the target level of stress, UAN was applied by fertigation or sidedress between V2 and VT, for a total of 50-150 lbs nitrogen.

Events from the construct were nested together with the null to minimize the spatial effects of field variation; 6 reps were planted in low nitrogen, 4 reps in normal nitrogen. The grain yield of events containing the transgene was compared to the yield of a transgenic null. Flowering time and staygreen were also monitored. Statistical analysis was conducted to assess whether there is a significant improvement in yield compared with the transgenic null, taking into account row and column spatial effects.

The relative yield data to nulls of PHP32101 (ZM-RM2: ADHI Intron:YNT1R3FS) from three locations are summarized in FIG. 3 (under NN) and FIG. 4 (under LN).

Example 12

Screen of Candidate Genes Under Nitrogen Limiting Conditions (Prophetic)

Transgenic seed selected by the presence of selectable marker can also be screened for their tolerance to grow under nitrogen limiting conditions. Transgenic individuals expressing the NTs described herein are plated on Low N medium (0.5×N-Free Hoagland's, 0.4 mM potassium nitrate, 0.1% sucrose, 1 mM MES and 0.25% Phytagel™), such that 32 transgenic individuals are grown next to 32 wild-type individuals on one plate. Plants are evaluated at 10, 11, 12 and 13 days. If a line shows a statistically significant difference from the controls, the line is considered a validated nitrogen-deficiency tolerant line. After masking the plate image to remove background color, two different measurements are collected for each individual: total rosetta area, and the percentage of color that falls into a green color bin. Using hue, saturation and intensity data (HIS), the green color bin consists of hues 50-66. Total rosetta area is used as a measure of plant biomass, whereas the green color bin has been shown by dose-response studies to be an indicator of nitrogen assimilation.

Example 13

Screens to Identify Lines with Altered Root Architecture (Prophetic)

Arabidopsis seedlings, grown under non-limiting nitrogen conditions, may be analyzed for altered root system architecture when compared to control seedlings during early development.

Transgenic NT variant seedlings from in-house screen are subjected to a vertical plate assay to evaluate enhanced root growth. The results are validated using WinRHIZO®, as described below. T2 seeds are sterilized using 50% household bleach 0.01% triton X-100 solution and plated on petri plates containing the following medium: 0.5×N-Free Hoagland's, 60 mM $KNO_3$, 0.1% sucrose, 1 mM MES and 1% Phytagel™ at a density of 4 seeds/plate. Plates are kept for three days at 4° C. to stratify seeds and then held vertically for 11 days at 22° C. light and 20° C. dark. Photoperiod is 16 h; 8 h dark and average light intensity is ~160 µmol/m²/s. Plates are placed vertically into the eight center positions of a 10 plate rack with the first and last position holding blank plates. The racks and the plates within a rack are rotated every other day. Two sets of pictures are taken for each plate. The first set taking place at day 14-16 when the primary roots for most lines are reached the bottom of the plate, the second set of pictures two days later after more lateral roots are developed. The latter set of picture is usually used for data analysis. These seedlings grown on vertical plates are analyzed for root growth with the software WinRHIZO® (Regent Instruments Inc), an image analysis system specifically designed for root measurement. WinRHIZO® uses the contrast in pixels to distinguish the light root from the darker background. To identify the maximum amount of roots without picking up background, the pixel classification is 150-170 and the filter feature is used to remove objects that have a length/width ratio less then 10.0. The area on the plates analyzed is from the edge of the plant's leaves to about 1 cm from the bottom of the plate. The exact same WinRHIZO® settings and area of analysis are used to analyze all plates within a batch. The total root length score given by WinRHIZO® for a plate is divided by the number of plants that are germinated and are grown halfway down the plate. Eight plates for every line are grown and their scores are averaged. This average is then compared to the average of eight plates containing wild type seeds that are grown at the same time.

Lines with enhanced root growth characteristics are expected to lie at the upper extreme of the root area distributions. A sliding window approach is used to estimate the variance in root area for a given rack with the assumption that there could be up to two outliers in the rack. Environmental variations in various factors including growth media, temperature, and humidity can cause significant variation in root growth, especially between sow dates. Therefore the lines are grouped by sow date and shelf for the data analysis. The racks in a particular sow date/shelf group are then sorted by mean root area. Root area distributions for sliding windows are performed by combining data for a rack, $r_i$, with data from the rack with the next lowest, ($r_{i-1}$, and the next highest mean root area, $r_{i+1}$. The variance of the combined distribution is then analyzed to identify outliers in $r_i$ using a Grubbs-type approach (Barnett et al., Outliers in Statistical Data, John Wiley & Sons, $3^{rd}$ edition (1994).

Example 14

NUE Assay Plant Growth (Prophetic)

Seeds of Arabidopsis thaliana (control and transgenic line), ecotype Columbia, are surface sterilized (Sanchez et al., 2002) and then plated on to Murashige and Skoog (MS) medium containing 0.8% (w/v) Bacto-Agar (Difco). Plates are incubated for 3 days in darkness at 4° C. to break dormancy (stratification) and transferred thereafter to growth chambers (Conviron, Manitoba, Canada) at a temperature of 20° C. under a 16-h light/8-h dark cycle. The average light intensity is 120 µE/m2/s. Seedling are grown for 12 days and the transfer to soil based pots. Potted plants are grown on a nutrient-free soil LB2 Metro-Mix 200 (Scott's Sierra Horticultural Products, Marysville, Ohio, USA) in individual 1.5-in pots (*Arabidopsis* system; Lehle Seeds, Round Rock, Tex., USA) in growth chambers, as described above. Plants are watered with 0.6 or 6.5 mM potassium nitrate in the nutrient solution based on Murashige and Skoog (MS free Nitrogen) medium. The relative humidity is maintained around 70%. 16-18 days later plant shoots are collected for evaluation of biomass and SPAD readings. Plants that improve NUE may have increased biomass at either high or low nitrate concentrations.

Example 15

Sucrose Growth Assay (Prophetic)

The Columbia line of *Arabidopsis thaliana* is obtained from the *Arabidopsis* Biological Resource Center (Columbus, Ohio). For early analysis (Columbia and T3 transgenic lines), seed are surface-sterilized with 70% ethanol for 5 min followed by 40% Clorox for 5 min and rinsed with sterile deionized water. Surface-sterilized seed are sown onto square Petri plates (25 cm) containing 95 mL of sterile medium consisting of 0.5 Murashige and Skoog (1962) salts (Life Technologies) and 4% (w/v) phytagel (Sigma). The medium contained no supplemental sucrose. Sucrose is added to medium in 0.1%, 0.5% and 1.5% concentration. Plates are arranged vertically in plastic racks and placed in a cold room for 3 days at 4° C. to synchronize germination. Racks with cold stratified seed are then transferred into growth chambers (Conviron, Manitoba, Canada) with day and night temperatures of 22 and 20° C., respectively. The average light intensity at the level of the rosette is maintained at 110 mol/m2/sec1 during a 16-hr light cycle development beginning at removal from the cold room (day 3 after sowing) until the seedlings are harvested on day 14. Images are taken and total fresh weight of root and shoot are measured. Two experiments will be performed. If expression or overexpression of an NT variant polynucleotide described herein alters the carbon and nitrogen balance, then data may show that the NT variant polynucleotide overexpression transgenic plants are increased or decreased root biomass and/or leaf biomass at different sucrose concentrations when compared to wild-type *Arabidopsis*.

Example 16

Transformation of Gaspe Flint Derived Maize Lines with NT Variant Polynucleotides Described Herein (Prophetic)

Maize plants can be transformed as described in Example 4-6 and overexpressing the NTs, for example using the ones described herein, in order to examine the resulting phenotype. Promoters including but not limited to the tubulin promoter (pTUB); maize ubiquitin promoter (ZM UBI), maize root metallothionein promoter (ZM-RM2); lipid transfer protein 2 promoter (LTP2); banana streak virus promoter truncated version promoter (BSV (TR)), maize NAS2 promoter (ZM-NAS2), and banana streak virus promoter (full version) (BAV (FL)) and others are useful for directing expression of the NTs in maize. Furthermore, a variety of terminators, such as, but not limited to the PINII terminator, can be used to achieve expression of the gene of interest in Gaspe Flint Derived Maize Lines.

Recipient Plants

Recipient plant cells can be from a uniform maize line having a short life cycle ("fast cycling"), a reduced size, and high transformation potential. Typical of these plant cells for maize are plant cells from any of the publicly available Gaspe Flint (GF) line varieties. One possible candidate plant line variety is the F1 hybrid of GF×QTM (Quick Turnaround Maize, a publicly available form of Gaspe Flint selected for growth under greenhouse conditions) disclosed in Tomes et al. U.S. Patent Application Publication No. 2003/0221212. Transgenic plants obtained from this line are of such a reduced size that they can be grown in four inch pots (¼ the space needed for a normal sized maize plant) and mature in less than 2.5 months. (Traditionally 3.5 months is required to obtain transgenic T0 seed once the transgenic plants are acclimated to the greenhouse.) Another suitable line is a double haploid line of GS3 (a highly transformable line) X Gaspe Flint. Yet another suitable line is a transformable elite inbred line carrying a transgene which causes early flowering, reduced stature, or both.

Transformation Protocol

Any suitable method may be used to introduce the transgenes into the maize cells, including but not limited to inoculation type procedures using *Agrobacterium* based vectors as described in Example 3. Transformation may be performed on immature embryos of the recipient (target) plant.

Precision Growth and Plant Tracking

The event population of transgenic (T0) plants resulting from the transformed maize embryos is grown in a controlled greenhouse environment using a modified randomized block design to reduce or eliminate environmental error. A randomized block design is a plant layout in which the experimental plants are divided into groups (e.g., thirty plants per group), referred to as blocks, and each plant is randomly assigned a location with the block.

For a group of thirty plants, twenty-four transformed, experimental plants and six control plants (plants with a set phenotype) (collectively, a "replicate group") are placed in pots which are arranged in an array (a.k.a. a replicate group or block) on a table located inside a greenhouse. Each plant, control or experimental, is randomly assigned to a location with the block which is mapped to a unique, physical greenhouse location as well as to the replicate group. Multiple replicate groups of thirty plants each may be grown in the same greenhouse in a single experiment. The layout (arrangement) of the replicate groups should be determined to minimize space requirements as well as environmental effects within the greenhouse. Such a layout may be referred to as a compressed greenhouse layout.

An alternative to the addition of a specific control group is to identify those transgenic plants that do not express the gene of interest. A variety of techniques such as RT-PCR can be applied to quantitatively assess the expression level of the introduced gene. T0 plants that do not express the transgene can be compared to those which do.

Each plant in the event population is identified and tracked throughout the evaluation process, and the data gathered from that plant is automatically associated with that plant so that the gathered data can be associated with the transgene carried by the plant. For example, each plant container can have a machine readable label (such as a Universal Product Code (UPC) bar code) which includes information about the plant identity, which in turn is correlated to a greenhouse location so that data obtained from the plant can be automatically associated with that plant.

Alternatively any efficient, machine readable, plant identification system can be used, such as two-dimensional matrix codes or even radio frequency identification tags (RFID) in which the data is received and interpreted by a radio frequency receiver/processor. See U.S. Published Patent Application No. 2004/0122592, incorporated herein by reference.

Phenotypic Analysis Using Three-Dimensional Imaging

Each greenhouse plant in the T0 event population, including any control plants, is analyzed for agronomic characteristics of interest, and the agronomic data for each plant is recorded or stored in a manner so that it is associated with the identifying data (see above) for that plant. Confirmation of a phenotype (gene effect) can be accomplished in the T1 generation with a similar experimental design to that described above.

The T0 plants are analyzed at the phenotypic level using quantitative, non-destructive imaging technology throughout the plant's entire greenhouse life cycle to assess the traits of interest. Preferably, a digital imaging analyzer is used for automatic multi-dimensional analyzing of total plants. The imaging may be done inside the greenhouse. Two camera systems, located at the top and side, and an apparatus to rotate the plant, are used to view and image plants from all sides. Images are acquired from the top, front and side of each plant. All three images together provide sufficient information to evaluate the biomass, size and morphology of each plant.

Due to the change in size of the plants from the time the first leaf appears from the soil to the time the plants are at the end of their development, the early stages of plant development are best documented with a higher magnification from the top. This may be accomplished by using a motorized zoom lens system that is fully controlled by the imaging software.

In a single imaging analysis operation, the following events occur: (1) the plant is conveyed inside the analyzer area, rotated 360 degrees so its machine readable label can be read, and left at rest until its leaves stop moving; (2) the side image is taken and entered into a database; (3) the plant is rotated 90 degrees and again left at rest until its leaves stop moving, and (4) the plant is transported out of the analyzer.

Plants are allowed at least six hours of darkness per twenty four hour period in order to have a normal day/night cycle.

Imaging Instrumentation

Any suitable imaging instrumentation may be used, including but not limited to light spectrum digital imaging instrumentation commercially available from LemnaTec GmbH of Wurselen, Germany. The images are taken and analyzed with a LemnaTec Scanalyzer HTS LT-0001-2 having a ½" IT Progressive Scan IEE CCD imaging device. The imaging cameras may be equipped with a motor zoom, motor aperture and motor focus. All camera settings may be made using LemnaTec software. Preferably, the instrumental variance of the imaging analyzer is less than about 5% for major components and less than about 10% for minor components.

Software

The imaging analysis system comprises a LemnaTec HTS Bonit software program for color and architecture analysis and a server database for storing data from about 500,000 analyses, including the analysis dates. The original images and the analyzed images are stored together to allow the user to do as much reanalyzing as desired. The database can be connected to the imaging hardware for automatic data collection and storage. A variety of commercially available software systems (e.g. Matlab, others) can be used for quantitative interpretation of the imaging data, and any of these software systems can be applied to the image data set.

Conveyor System

A conveyor system with a plant rotating device may be used to transport the plants to the imaging area and rotate them during imaging. For example, up to four plants, each with a maximum height of 1.5 m, are loaded onto cars that travel over the circulating conveyor system and through the imaging measurement area. In this case the total footprint of the unit (imaging analyzer and conveyor loop) is about 5 m×5 m.

The conveyor system can be enlarged to accommodate more plants at a time. The plants are transported along the conveyor loop to the imaging area and are analyzed for up to 50 seconds per plant. Three views of the plant are taken. The conveyor system, as well as the imaging equipment, should be capable of being used in greenhouse environmental conditions.

Illumination

Any suitable mode of illumination may be used for the image acquisition. For example, a top light above a black background can be used. Alternatively, a combination of top- and backlight using a white background can be used. The illuminated area should be housed to ensure constant illumination conditions. The housing should be longer than the measurement area so that constant light conditions prevail without requiring the opening and closing or doors. Alternatively, the illumination can be varied to cause excitation of either transgene (e.g., green fluorescent protein (GFP), red fluorescent protein (RFP)) or endogenous (e.g. Chlorophyll) fluorophores.

Biomass Estimation Based on Three-Dimensional Imaging

For best estimation of biomass the plant images should be taken from at least three axes, preferably the top and two side (sides 1 and 2) views. These images are then analyzed to separate the plant from the background, pot and pollen control bag (if applicable). The volume of the plant can be estimated by the calculation:

$$\text{Volume(voxels)} = \sqrt{\text{TopArea(pixels)}} \times \sqrt{\text{Side1Area(pixels)}} \times \sqrt{\text{Side2Area(pixels)}}$$

In the equation above the units of volume and area are "arbitrary units". Arbitrary units are entirely sufficient to detect gene effects on plant size and growth in this system because what is desired is to detect differences (both positive-larger and negative-smaller) from the experimental mean, or control mean. The arbitrary units of size (e.g. area) may be trivially converted to physical measurements by the addition of a physical reference to the imaging process. For instance, a physical reference of known area can be included in both top and side imaging processes. Based on the area of these physical references a conversion factor can be determined to allow conversion from pixels to a unit of area such as square centimeters ($cm^2$). The physical reference may or may not be an independent sample. For instance, the pot, with a known diameter and height, could serve as an adequate physical reference.

Color Classification

The imaging technology may also be used to determine plant color and to assign plant colors to various color classes. The assignment of image colors to color classes is an inherent feature of the LemnaTec software. With other image analysis software systems color classification may be determined by a variety of computational approaches.

For the determination of plant size and growth parameters, a useful classification scheme is to define a simple color scheme including two or three shades of green and, in addition, a color class for chlorosis, necrosis and bleaching, should these conditions occur. A background color class which includes non plant colors in the image (for example pot and soil colors) is also used and these pixels are specifically excluded from the determination of size. The plants are analyzed under controlled constant illumination so that any change within one plant over time, or between plants or different batches of plants (e.g. seasonal differences) can be quantified.

In addition to its usefulness in determining plant size growth, color classification can be used to assess other yield component traits. For these other yield component traits additional color classification schemes may be used. For instance, the trait known as "staygreen", which has been associated with improvements in yield, may be assessed by a color classification that separates shades of green from shades of yellow and brown (which are indicative of senescing tissues). By applying this color classification to images taken toward the end of the T0 or T1 plants' life cycle, plants that have increased amounts of green colors relative to yellow and brown colors (expressed, for instance, as Green/Yellow Ratio) may be identified. Plants with a significant difference in this Green/Yellow ratio can be identified as carrying transgenes which impact this important agronomic trait.

The skilled plant biologist will recognize that other plant colors arise which can indicate plant health or stress response (for instance anthocyanins), and that other color classification schemes can provide further measures of gene action in traits related to these responses.

Plant Architecture Analysis

Transgenes which modify plant architecture parameters may also be identified using the present invention, including such parameters as maximum height and width, internodal distances, angle between leaves and stem, number of leaves starting at nodes and leaf length. The LemnaTec system software may be used to determine plant architecture as follows. The plant is reduced to its main geometric architecture in a first imaging step and then, based on this image, parameterized identification of the different architecture parameters can be performed. Transgenes that modify any of these architecture parameters either singly or in combination can be identified by applying the statistical approaches previously described.

Pollen Shed Date

Pollen shed date is an important parameter to be analyzed in a transformed plant, and may be determined by the first appearance on the plant of an active male flower. To find the male flower object, the upper end of the stem is classified by color to detect yellow or violet anthers. This color classification analysis is then used to define an active flower, which in turn can be used to calculate pollen shed date.

Alternatively, pollen shed date and other easily visually detected plant attributes (e.g. pollination date, first silk date) can be recorded by the personnel responsible for performing plant care. To maximize data integrity and process efficiency this data is tracked by utilizing the same barcodes utilized by the LemnaTec light spectrum digital analyzing device. A computer with a barcode reader, a palm device, or a notebook PC may be used for ease of data capture recording time of observation, plant identifier, and the operator who captured the data.

Orientation of the Plants

Mature maize plants grown at densities approximating commercial planting often have a planar architecture. That is, the plant has a clearly discernable broad side, and a narrow side. The image of the plant from the broadside is determined. To each plant a well defined basic orientation is assigned to obtain the maximum difference between the broadside and edgewise images. The top image is used to determine the main axis of the plant, and an additional rotating device is used to turn the plant to the appropriate orientation prior to starting the main image acquisition.

Example 17

Transgenic Maize Plants (Prophetic)

$T_0$ transgenic maize plants containing the NT variant construct under the control of a promoter will be generated. These plants were grown in greenhouse conditions, under the FAST-CORN system, as detailed in U.S. Patent Application Publication 2003/0221212, U.S. patent application Ser. No. 10/367,417.

Each of the plants was analyzed for measurable alteration in one or more of the following characteristics in the following manner:

$T_1$ progeny derived from self fertilization each $T_0$ plant containing a single copy of each NT variant construct that were found to segregate 1:1 for the transgenic event will be analyzed for improved growth rate in low $KNO_3$. Growth will be monitored up to anthesis when cumulative plant growth, growth rate and ear weight were determined for transgene positive, transgene null, and non-transformed controls events. The distribution of the phenotype of individual plants was compared to the distribution of a control set and to the distribution of all the remaining treatments. Variances for each set will be calculated and compared using an F test, comparing the event variance to a non-transgenic control set variance and to the pooled variance of the remaining events in the experiment. The greater the response to $KNO_3$, the greater the variance within an event set and the greater the F value. Positive results will be compared to the distribution of the transgene within the event to make sure the response segregates with the transgene.

Example 18

Transgenic Event Analysis from Field Plots (Prophetic)

Transgenic events are evaluated in field plots where yield is limited by reducing fertilizer application by 30% or more. Improvements in yield, yield components, or other agronomic traits between transgenic and non-transgenic plants in these reduced nitrogen fertility plots are used to assess improvements in nitrogen utilization contributed by expression of transgenic events. Similar comparisons are made in plots supplemented with recommended nitrogen fertility rates. Effective transgenic events are those that achieve similar yields in the nitrogen-limited and normal nitrogen experiments.

Example 19

Assays to Determine Alterations of Root Architecture in Maize

Transgenic maize plants are assayed for changes in root architecture at seedling stage, flowering time or maturity. Assays to measure alterations of root architecture of maize plants include, but are not limited to the methods outlined below. To facilitate manual or automated assays of root architecture alterations, corn plants can be grown in clear pots.

1. Root mass (dry weights). Plants are grown in Turface, a growth media that allows easy separation of roots. Oven-dried shoot and root tissues are weighed and a root/shoot ratio calculated.
2. Levels of lateral root branching. The extent of lateral root branching (e.g. lateral root number, lateral root length) is determined by sub-sampling a complete root system, imaging with a flat-bed scanner or a digital camera and analyzing with WinRHIZO™ software (Regent Instruments Inc.).
3. Root band width measurements. The root band is the band or mass of roots that forms at the bottom of greenhouse pots as the plants mature. The thickness of the root band is measured in mm at maturity as a rough estimate of root mass.
4. Nodal root count. The number of crown roots coming off the upper nodes can be determined after separating the root from the support medium (e.g. potting mix). In addition the angle of crown roots and/or brace roots can be measured. Digital analysis of the nodal roots and amount of branching of nodal roots form another extension to the aforementioned manual method.

All data taken on root phenotype are subjected to statistical analysis, normally a t-test to compare the transgenic roots with that of non-transgenic sibling plants. One-way ANOVA may also be used in cases where multiple events and/or constructs are involved in the analysis.

Example 20

Soybean Embryo Transformation (Prophetic)

Soybean embryos are bombarded with a plasmid containing an antisense NT variant sequences operably linked to an ubiquitin promoter as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein, et al., (1987) *Nature* (*London*) 327:70-73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell, et al., (1985) *Nature* 313:810-812), the hygromycin phosphotransferase gene from plasmid pJR225 (from *E. coli*; Gritz, et al., (1983) *Gene* 25:179-188), and the 3' region of the nopaline synthase gene from the T-DNA of the Ti plasmid of *Agrobacterium tumefaciens*. The expression cassette comprising an NT variant sequence described herein operably linked to the ubiquitin promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl $CaCl_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 21

Sunflower Meristem Tissue Transformation (Prophetic)

Sunflower meristem tissues are transformed with an expression cassette containing an NT variant sequence described herein operably linked to a ubiquitin promoter as follows (see also, European Patent Number EP 0 486233, herein incorporated by reference, and Malone-Schoneberg, et al., (1994) *Plant Science* 103:199-207). Mature sunflower seed (*Helianthus annuus* L.) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer, et al. (Schrammeijer, et al., (1990) *Plant Cell Rep.* 9:55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige, et al., (1962) *Physiol. Plant.*, 15:473-497), Shepard's vitamin additions (Shepard, (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid ($GA_3$), pH 5.6, and 8 g/l Phytagar.

The explants are subjected to microprojectile bombardment prior to *Agrobacterium* treatment (Bidney, et al., (1992) *Plant Mol. Biol.* 18:301-313). Thirty to forty explants are placed in a circle of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the NT variant polynucleotide operably linked to the ubiquitin promoter is introduced into *Agrobacterium* strain EHA105 via freeze-thawing as described by Holsters, et al., (1978) *Mol. Gen. Genet.* 163:181-187. This plasmid further comprises a kanamycin selectable marker gene (i.e., nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for a modulation in meristem development (i.e., an alteration of size and appearance of shoot and floral meristems).

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by nitrate uptake, NT or NUE activity analysis of leaf extracts while transgenic seeds harvested from NPTII-positive $T_0$ plants are identified by nitrate uptake, NT or NUE activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 µm tungsten particles are resuspended in 150 µl absolute ethanol. After sonication, 8 µl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 µg/l kanamycin is resuspended in an inoculation medium (12.5 mM 2-mM 2-(N-morpholino) ethanesulfonic acid, MES, 1 g/l $NH_4Cl$ and 0.3 g/l $MgSO_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 µg/ml cefotaxime). The plantlets are cultured on the medium for about two weeks under 16-hour day and 26° C. incubation conditions.

Explants (around 2 cm long) from two weeks of culture in 374C medium are screened for a modulation in meristem development (i.e., an alteration of size and appearance of shoot and floral meristems). After positive explants are identified, those shoots that fail to exhibit modified NT activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for modified NT variant expression are grafted to Pioneer hybrid 6440 in vitro-grown sunflower seedling rootstock. The rootstocks are prepared in the following manner. Seeds are dehulled and surface-sterilized for 20 minutes in a 20% Clorox bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

Example 22

Rice Tissue Transformation (Prophetic)

One method for transforming DNA into cells of higher plants that is available to those skilled in the art is high-velocity ballistic bombardment using metal particles coated with the nucleic acid constructs of interest (see, Klein, et al., Nature (1987) (London) 327:70-73, and see U.S. Pat. No. 4,945,050). A Biolistic PDS-1000/He (BioRAD Laboratories, Hercules, Calif.) is used for these complementation experiments. The particle bombardment technique is used to transform the NT variant mutants and wild type rice with DNA fragments The bacterial hygromycin B phosphotransferase (Hpt II) gene from Streptomyces hygroscopicus that confers resistance to the antibiotic is used as the selectable marker for rice transformation. In the vector, pML18, the Hpt II gene was engineered with the 35S promoter from Cauliflower Mosaic Virus and the termination and polyadenylation signals from the octopine synthase gene of Agrobacterium tumefaciens. pML18 was described in WO 97/47731, which was published on Dec. 18, 1997, the disclosure of which is hereby incorporated by reference.

Embryogenic callus cultures derived from the scutellum of germinating rice seeds serve as source material for transformation experiments. This material is generated by germinating sterile rice seeds on a callus initiation media (MS salts, Nitsch and Nitsch vitamins, 1.0 mg/l 2,4-D and 10 µM AgNO$_3$) in the dark at 27-28° C. Embryogenic callus proliferating from the scutellum of the embryos is the transferred to CM media (N6 salts, Nitsch and Nitsch vitamins, 1 mg/l 2,4-D, Chu, et al., 1985, Sci. Sinica 18: 659-668). Callus cultures are maintained on CM by routine sub-culture at two week intervals and used for transformation within 10 weeks of initiation.

Callus is prepared for transformation by subculturing 0.5-1.0 mm pieces approximately 1 mm apart, arranged in a circular area of about 4 cm in diameter, in the center of a circle of Whatman #541 paper placed on CM media. The plates with callus are incubated in the dark at 27-28° C. for 3-5 days. Prior to bombardment, the filters with callus are transferred to CM supplemented with 0.25 M mannitol and 0.25 M sorbitol for 3 hr in the dark. The petri dish lids are then left ajar for 20-45 minutes in a sterile hood to allow moisture on tissue to dissipate.

Each genomic DNA fragment is co-precipitated with pML18 containing the selectable marker for rice transformation onto the surface of gold particles. To accomplish this, a total of 10 µg of DNA at a 2:1 ratio of trait:selectable marker DNAs are added to 50 µl aliquot of gold particles that have been resuspended at a concentration of 60 mg ml$^{-1}$. Calcium chloride (50 µl of a 2.5 M solution) and spermidine (20 µl of a 0.1 M solution) are then added to the gold-DNA suspension as the tube is vortexing for 3 min. The gold particles are centrifuged in a microfuge for 1 sec and the supernatant removed. The gold particles are then washed twice with 1 ml of absolute ethanol and then resuspended in 50 µl of absolute ethanol and sonicated (bath sonicator) for one second to disperse the gold particles. The gold suspension is incubated at −70° C. for five minutes and sonicated (bath sonicator) if needed to disperse the particles. Six µl of the DNA-coated gold particles are then loaded onto mylar macrocarrier disks and the ethanol is allowed to evaporate.

At the end of the drying period, a petri dish containing the tissue is placed in the chamber of the PDS-1000/He. The air in the chamber is then evacuated to a vacuum of 28-29 inches Hg. The macrocarrier is accelerated with a helium shock wave using a rupture membrane that bursts when the He pressure in the shock tube reaches 1080-1100 psi. The tissue is placed approximately 8 cm from the stopping screen and the callus is bombarded two times. Two to four plates of tissue are bombarded in this way with the DNA-coated gold particles. Following bombardment, the callus tissue is transferred to CM media without supplemental sorbitol or mannitol.

Within 3-5 days after bombardment the callus tissue is transferred to SM media (CM medium containing 50 mg/l hygromycin). To accomplish this, callus tissue is transferred from plates to sterile 50 ml conical tubes and weighed. Molten top-agar at 40° C. is added using 2.5 ml of top agar/100 mg of callus. Callus clumps are broken into fragments of less than 2 mm diameter by repeated dispensing through a 10 ml pipet. Three ml aliquots of the callus suspension are plated onto fresh SM media and the plates are incubated in the dark for 4 weeks at 27-28° C. After 4 weeks, transgenic callus events are identified, transferred to fresh SM plates and grown for an additional 2 weeks in the dark at 27-28° C.

Growing callus is transferred to RM1 media (MS salts, Nitsch and Nitsch vitamins, 2% sucrose, 3% sorbitol, 0.4% gelrite+50 ppm hyg B) for 2 weeks in the dark at 25° C. After 2 weeks the callus is transferred to RM2 media (MS salts, Nitsch and Nitsch vitamins, 3% sucrose, 0.4% gelrite+50 ppm hyg B) and placed under cool white light (~40 µEm$^{-2}$s$^{-1}$) with a 12 hr photo period at 25° C. and 30-40% humidity. After 2-4 weeks in the light, callus begin to organize, and form shoots. Shoots are removed from surrounding callus/media and gently transferred to RM3 media (½×MS salts, Nitsch and Nitsch vitamins, 1% sucrose+50 ppm hygromycin B) in phytatrays (Sigma Chemical Co., St. Louis, Mo.) and incubation is continued using the same conditions as described in the previous step.

Plants are transferred from RM3 to 4" pots containing Metro mix 350 after 2-3 weeks, when sufficient root and shoot growth have occurred. The seed obtained from the transgenic plants is examined for genetic complementation of the NT variant mutation with the wild-type genomic DNA containing the NT variant polynucleotide.

Example 23

NUE Assay

Using the protocol detailed in U.S. Patent Application Ser. No. 61/227,276, a triphenyltetrazolium chloride (TTC) assay may be performed to evaluate genes for NUE, for example, increased transport activity in roots, using transgenic maize lines.

Example 24

Variants of NT Variant Sequences (Prophetic)

A. Variant Nucleotide Sequences of NT Variant Proteins that do not Alter the Encoded Amino Acid Sequence The NT variant nucleotide sequences described herein are used to generate variant nucleotide sequences having the nucleotide sequence of the open reading frame with about 70%, 75%, 80%, 85%, 90%, and 95% nucleotide sequence identity when compared to the starting unaltered ORF nucleotide sequence of the corresponding SEQ ID NO:3, 5, 7, 9, or 11. These functional variants are generated using a standard codon table. While the nucleotide sequence of the variants are altered, the amino acid sequence encoded by the open reading frames do not change.

B. Variant Amino Acid Sequences of NT Variant Polypeptides

Variant amino acid sequences of the NT variant polypeptides are generated. In this example, one amino acid is altered. Specifically, the open reading frames are reviewed to determine the appropriate amino acid alteration. The selection of the amino acid to change is made by consulting the protein alignment (with the other orthologs and other gene family members from various species). An amino acid is selected that is deemed not to be under high selection pressure (not highly conserved) and which is rather easily substituted by an amino acid with similar chemical characteristics (i.e., similar functional side-chain). Using the protein alignment, an appropriate amino acid can be changed. Once the targeted amino acid is identified, the procedure outlined in the following section C is followed. Variants having about 70%, 75%, 80%, 85%, 90%, and 95% nucleic acid sequence identity are generated using this method.

C. Additional Variant Amino Acid Sequences of NT Variant Polypeptides

In this example, artificial protein sequences are created having 80%, 85%, 90%, and 95% identity relative to the reference protein sequence. This latter effort requires identifying conserved and variable regions from the alignment and then the judicious application of an amino acid substitutions table. These parts will be discussed in more detail below.

Largely, the determination of which amino acid sequences are altered is made based on the conserved regions among NT variant protein or among the other NT variant polypeptides. Based on the sequence alignment, the various regions of the NT variant polypeptide that can likely be altered are represented in lower case letters, while the conserved regions are represented by capital letters. It is recognized that conservative substitutions can be made in the conserved regions below without altering function. In addition, one of skill will understand that functional variants of the NT variant sequence of the invention can have minor non-conserved amino acid alterations in the conserved domain.

Artificial protein sequences are then created that are different from the original in the intervals of 80-85%, 85-90%, 90-95%, and 95-100% identity. Midpoints of these intervals are targeted, with liberal latitude of plus or minus 1%, for example. The amino acids substitutions will be effected by a custom Perl script. The substitution table is provided below in Table 9.

TABLE 9

Substitution Table

| Amino Acid | Strongly Similar and Optimal Substitution | Rank of Order to Change | Comment |
|---|---|---|---|
| I | L, V | 1 | 50:50 substitution |
| L | I, V | 2 | 50:50 substitution |
| V | I, L | 3 | 50:50 substitution |
| A | G | 4 | |
| G | A | 5 | |
| D | E | 6 | |

TABLE 9-continued

Substitution Table

| Amino Acid | Strongly Similar and Optimal Substitution | Rank of Order to Change | Comment |
|---|---|---|---|
| E | D | 7 | |
| W | Y | 8 | |
| Y | W | 9 | |
| S | T | 10 | |
| T | S | 11 | |
| K | R | 12 | |
| R | K | 13 | |
| N | Q | 14 | |
| Q | N | 15 | |
| F | Y | 16 | |
| M | L | 17 | First methionine cannot change |
| H | | Na | No good substitutes |
| C | | Na | No good substitutes |
| P | | Na | No good substitutes |

First, any conserved amino acids in the protein that should not be changed is identified and "marked off" for insulation from the substitution. The start methionine will of course be added to this list automatically. Next, the changes are made.

H, C, and P are not changed in any circumstance. The changes will occur with isoleucine first, sweeping N-terminal to C-terminal. Then leucine, and so on down the list until the desired target it reached. Interim number substitutions can be made so as not to cause reversal of changes. The list is ordered 1-17, so start with as many isoleucine changes as needed before leucine, and so on down to methionine. Clearly many amino acids will in this manner not need to be changed. L, I and V will involve a 50:50 substitution of the two alternate optimal substitutions.

The variant amino acid sequences are written as output. Perl script is used to calculate the percent identities. Using this procedure, variants of the NT variant polypeptides are generating having about 80%, 85%, 90%, and 95% amino acid identity to the starting unaltered ORF nucleotide sequence of SEQ ID NOS:3, 5, 7, 9, or 11.

Example 25

Nitrate Uptake Assay to Determining Expression Level and Activity of YNT1 Variants as Compared to Wild Type YNT1 in Maize Corn seeds containing the transgene are planted in small pots and water with nutrient solution containing nitrate as the sole nitrogen source. The pots with seedlings are transferred into a larger container containing the same nutrient solution. An aliquot of nutrient solution is removed and the amount of nitrate is determined. Two weeks after transfer the plants are harvested for biomass and total reduced nitrogen measurements. The loss of nitrate from the nutrient solution is used to determine the nitrate uptake.

Example 26

Maize Transient Expression Assay to Determine Protein Expression Level (Prophetic)

Protein expression level can be determined by *Agrobacterium*-mediated transient expression assay in maize. A binary plasmid vector comprising the expression cassette that contains the NT polynucleotide driven by maize ubiquitin promoter or PEPC promoter is introduced into *Agrobacterium* strain LBA4404 via electroporation as that described in Example 6. Maize seedlings, young leaf tissues, or suspension cells are infected by the *Agrobacterium* culture carrying the NT expression cassette by infiltration or vacuum. The infected plant materials are recovered for few days under desired conditions, e.g. green house or growth camber with nutrients/medium. Proteins are extracted from the infected tissues and analyzed by Western blot following the standard procedure.

The article "a" and "an" are used herein to refer to one or more than one (i.e., to at least one) of the grammatical object of the article. By way of example, "an element" means one or more element.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

That which is claimed:

1. An isolated or recombinant polynucleotide comprising a member selected from the group consisting of:
   (a) a polynucleotide that encodes a polypeptide comprising the amino acid sequence set forth in SEQ ID NO:10,
   (b) a polynucleotide comprising the nucleotide sequence set forth in SEQ ID NO:11,
   (c) a polynucleotide encoding a polypeptide having at least 95% sequence identity to the amino acid sequence set forth in SEQ ID NO:10 and wherein the polypeptide has increased velocity ($V_{max}$) for nitrate uptake as compared to YNT1,
   (d) a polynucleotide degenerate from any one of (a) to (c) as a result of the genetic code, and
   (e) a polynucleotide complementary to a polynucleotide of any one of (a) to (d).

2. The isolated or recombinant polynucleotide of claim 1, wherein said polynucleotide encodes a polypeptide that increases a plant's yield relative to the yield of a control plant that does not contain the said polynucleotide.

3. The isolated or recombinant polynucleotide of claim 1 that encodes a polypeptide having a $V_{max}$ that is at least 2-fold greater than the $V_{max}$ of the polypeptide of SEQ ID NO: 2.

4. A vector comprising at least one polynucleotide, or a recombinant expression cassette comprising at least one polynucleotide operably linked to a promoter; wherein the polynucleotide is the polynucleotide of claim 1.

5. A host cell comprising at least one vector or at least one recombinant expression cassette of claim 4.

6. The host cell of claim 5, wherein the host cell is a monocotyledonous plant cell or dicotyledonous plant cell.

7. A transgenic plant comprising stably incorporated in its genome at least one recombinant expression cassette comprising at least one polynucleotide operably linked to a promoter; wherein the polynucleotide comprises a member selected from the group consisting of:
   (a) a polynucleotide that encodes a polypeptide comprising the amino acid sequence set forth in SEQ ID NO:10,
   (b) a polynucleotide comprising the nucleotide sequence set forth in SEQ ID NO:11,
   (c) a polynucleotide encoding a polypeptide having at least 95% sequence identity to the amino acid sequence set forth in SEQ ID NO:10 and wherein the polypeptide has increased velocity ($V_{max}$) for nitrate uptake as compared to YNT1,
   (d) a polynucleotide degenerate from any one of (a) to (c) as a result of the genetic code, and
   (e) a polynucleotide complementary to a polynucleotide of any one of (a) to (d).

8. The transgenic plant of claim 7, wherein the plant is selected from the group consisting of: *Arabidopsis*, maize, soybean, sunflower, sorghum, canola, wheat, alfalfa, cotton, rice, barley, millet, peanut, sugarcane, and cocoa.

9. A seed from the transgenic plant of claim 7, wherein said seed comprises said recombinant expression cassette.

10. An isolated or recombinant polypeptide selected from the group consisting of:
    (a) a polypeptide encoded by the nucleotide sequence set forth in SEQ ID NO:11; and
    (b) a polypeptide having 95% sequence identity to the amino acid sequence set forth in SEQ ID NO:10, wherein the polypeptide has increased velocity ($V_{max}$) for nitrate uptake as compared to YNT1.

* * * * *

SEQUENCE LISTING

```
<160> NUMBER OF SEQ ID NOS: 17

<210> SEQ ID NO 1
<211> LENGTH: 1527
<212> TYPE: DNA
<213> ORGANISM: Pichia angusta

<400> SEQUENCE: 1
atgcaactgt ctaccttatg ggaaccgcca atagtgaatc caagaaacct gaaagcgacc      60
tcaataccaa tttttaacct atggaacgtc tatggaagaa acttcttttt cgggtggttt     120 ggttttttg tttgttttct ttcttggttc gcgtttccgc ctcttctcca tggcatgttg      180
aagaaggacc taagactcac tgcagtggat atatccaata ataacatatg tggactgaca     240
ggaactttac taggcagatt cattttgggg cccttaacg acaagtatgg cccacggatt      300
actttgacag gcgtgctggt tgcaggagca attccgactg catttgttcc tttggttaca     360
aatgttgcag gtctacatgc cattcgcttt tttatcagct ttctaggctc ctcgtttatt     420
tgttgctccc aattctgcgc tgtattttt gataacaaca ttatagggac agcaaatgcc      480
atctctgccg gttggggaaa tgctggagga ggtgtggcat tctttgtcat gcctgccatt     540
tcaaatgcgt tggaaaatag aggttactct ttgcaccatt cttggagcta ctcttttgtg     600
attgggccgt tcttaatttt gatgatcacg gcaatactga tctttgtatt tggaagcgac     660
tgcccgagag gcagatggtc ccttcgtgga gatatccttg gtatcaacat ggataatatg     720
ctcgtgaagt ctgtctctgt cacaaggcac ttctctaagg aaggagagct cacttctgta     780
tttgttgagc ctgttaacgc aattgataag gtcgtggttg agcccaatca agaccaggaa     840
attcttgaag tcgcagatat cataaatggt gacgaaatca ttgaagaccc atcgctcaat     900
gacgtggtca agatctgttt atccccgcgg acaatgctgg tcggactttg ctacatgtgc     960
tcgtttggta ctgagcttgc agtagagtct attatttcca acctgttcgg gcaaaagatg    1020
acaaactgga gcacctctaa agctggagca tggggctcaa tgcttggact cctgaacgtg    1080
gtggcaagac cagctggagg gatcatctcc gattttttat accaaagatt caaaaccaca    1140
aaggctaaaa agttctggat gatcttcact ggcctgatgc agggcatttt tttgatttgg    1200
attggactag ttccggaatt atccatcgcg ggactcatag tgtccgtttc gttttgtgt     1260 ctttggtttg agatgggtaa tggtgcaaat tatgcatgtg ttcccgttgt gaatagacat    1320
cacagtggta ttgtgagtgg agttacggga gcaatgggta acttaggagg catttgttt    1380 agtttagtgt tcaggtacac tatatcaaat ggagtgaaca actacttcaa ggcgttttgg    1440
attataggaa ttgtttgcac tgctgtaaat ctggtctgtg tgcttattcc aattagagag    1500
gagaggccaa ggaaagcgga aaattga                                         1527
```

```
<210> SEQ ID NO 2
<211> LENGTH: 508
<212> TYPE: PRT
<213> ORGANISM: Pichia angusta

<400> SEQUENCE: 2

Met Gln Leu Ser Thr Leu Trp Glu Pro Pro Ile Val Asn Pro Arg Asn
 1               5                  10                  15

Leu Lys Ala Thr Ser Ile Pro Ile Phe Asn Leu Trp Asn Val Tyr Gly
             20                  25                  30

Arg Asn Phe Phe Phe Gly Trp Phe Gly Phe Val Cys Phe Leu Ser
         35                  40                  45

Trp Phe Ala Phe Pro Pro Leu Leu His Gly Met Leu Lys Lys Asp Leu
 50                  55                  60

Arg Leu Thr Ala Val Asp Ile Ser Asn Asn Ile Cys Gly Leu Thr
 65                  70                  75                  80

Gly Thr Leu Leu Gly Arg Phe Ile Leu Gly Pro Leu Asn Asp Lys Tyr
                 85                  90                  95

Gly Pro Arg Ile Thr Leu Thr Gly Val Leu Val Ala Gly Ala Ile Pro
            100                 105                 110

Thr Ala Phe Val Pro Leu Val Thr Asn Val Ala Gly Leu His Ala Ile
            115                 120                 125

Arg Phe Phe Ile Ser Phe Leu Gly Ser Ser Phe Ile Cys Cys Ser Gln
130                 135                 140

Phe Cys Ala Val Phe Phe Asp Asn Asn Ile Ile Gly Thr Ala Asn Ala
145                 150                 155                 160

Ile Ser Ala Gly Trp Gly Asn Ala Gly Gly Gly Val Ala Phe Phe Val
                165                 170                 175

Met Pro Ala Ile Ser Asn Ala Leu Glu Asn Arg Gly Tyr Ser Leu His
            180                 185                 190

His Ser Trp Ser Tyr Ser Phe Val Ile Gly Pro Phe Leu Ile Leu Met
            195                 200                 205

Ile Thr Ala Ile Leu Ile Phe Val Phe Gly Ser Asp Cys Pro Arg Gly
            210                 215                 220

Arg Trp Ser Leu Arg Gly Asp Ile Leu Gly Ile Asn Met Asp Asn Met
225                 230                 235                 240

Leu Val Lys Ser Val Ser Val Thr Arg His Phe Ser Lys Glu Gly Glu
                245                 250                 255

Leu Thr Ser Val Phe Val Glu Pro Val Asn Ala Ile Asp Lys Val Val
            260                 265                 270

Val Glu Pro Asn Gln Asp Gln Glu Ile Leu Glu Val Ala Asp Ile Ile
            275                 280                 285

Asn Gly Asp Glu Ile Ile Glu Asp Pro Ser Leu Asn Asp Val Val Lys
            290                 295                 300

Ile Cys Leu Ser Pro Arg Thr Met Leu Val Gly Leu Cys Tyr Met Cys
305                 310                 315                 320

Ser Phe Gly Thr Glu Leu Ala Val Glu Ser Ile Ile Ser Asn Leu Phe
                325                 330                 335

Gly Gln Lys Met Thr Asn Trp Ser Thr Ser Lys Ala Gly Ala Trp Gly
            340                 345                 350

Ser Met Leu Gly Leu Leu Asn Val Val Ala Arg Pro Ala Gly Gly Ile
            355                 360                 365

Ile Ser Asp Phe Leu Tyr Gln Arg Phe Lys Thr Thr Lys Ala Lys Lys
            370                 375                 380

Phe Trp Met Ile Phe Thr Gly Leu Met Gln Gly Ile Phe Leu Ile Trp
```

|     |     |     |     |     |     |     |     |     |     |     |     |
|---|---|---|---|---|---|---|---|---|---|---|---|
| 385 | | | | | 390 | | | | | 395 | 400 |

Ile Gly Leu Val Pro Glu Leu Ser Ile Ala Gly Leu Ile Val Ser Val
              405                 410                 415

Ser Phe Leu Cys Leu Trp Phe Glu Met Gly Asn Gly Ala Asn Tyr Ala
              420                 425                 430

Cys Val Pro Val Val Asn Arg His His Ser Gly Ile Val Ser Gly Val
              435                 440                 445

Thr Gly Ala Met Gly Asn Leu Gly Gly Ile Leu Phe Ser Leu Val Phe
              450                 455                 460

Arg Tyr Thr Ile Ser Asn Gly Val Asn Asn Tyr Phe Lys Ala Phe Trp
465               470                 475                 480

Ile Ile Gly Ile Val Cys Thr Ala Val Asn Leu Val Cys Val Leu Ile
              485                 490                 495

Pro Ile Arg Glu Glu Arg Pro Arg Lys Ala Glu Asn
              500                 505

<210> SEQ ID NO 3
<211> LENGTH: 1527
<212> TYPE: DNA
<213> ORGANISM: Pichia angusta

<400> SEQUENCE: 3

| | |
|---|---|
| atgcaactgt ctaccttatg ggaaccgcca atagtgaatc caagaaacct gaaagcgacc | 60 |
| tcaataccaa tttttaacct atggaacgtc tatggaagaa acttcttttt cgggtggttt | 120 |
| ggttttttg ttgcttttct ttcttggttc gcgtttccgc ctcttctcca tggcatgttg | 180 |
| aagaaggacc taagactcac tgcagtggat atatccaata ataacatatg ggactgaca | 240 |
| ggaactttac taggcagatt cattttgggg ccccttaacg acaagtatgg cccacggatt | 300 |
| actttggctg cgtgctggt tgcaggagca attccgactg catttgttcc tttggttaca | 360 |
| aatgttgcag tctacatgc cattcgcttt tctatcagct ttctaggctc ctcgtttatt | 420 |
| tgttgctccc aattctgcgc tgtatttttt gataacaaca ttgtggggac agcaaatgcc | 480 |
| gtctctgccg ttggggaaa tgctggagga ggtgtggcat tctttgtcat gcctgccatt | 540 |
| tcaaatgcgt tggaaaatag aggttactct ttgcaccatt cttggagcta ctcttttgtg | 600 |
| attgggccgt tcttaatttt gatgatcacg gcaatactga cctttgtatt tggaagcgac | 660 |
| tgcccgagag gcagatggtc ccttcgtgga gataccctg gtatcaacat ggataatatg | 720 |
| ctcgtgaagt ctgtctctac cacaaggcac ttccctaagg aaggagagct cacttctgta | 780 |
| tttgttgagc ctgttaacgc aattgataag gctgtgtccg agcccaatca agaccaggaa | 840 |
| attcttgaag tcgcagatat cataaatggt gacgaaatca ttgaagaccc atcgctcaat | 900 |
| gacgtggtca agatcctttt tatccccgcg gacaatgctgg tcggactttg ctacatgtgc | 960 |
| tcgtttggta ctgagcttgc ggtagagtct attatttcca acctgttcgg gcaaaagatg | 1020 |
| acaagctgga gcacctctaa agctggagca tggggctcaa tgcttggact cctgaacgtg | 1080 |
| gtggcaagac cagctggagg aatcatctcc gattttttat accaaagatt caaaaccaca | 1140 |
| aaggctaaaa agttctggat gatcttcact ggcctgatgc agggcatttt tttgatttgg | 1200 |
| atcggactag ttccggaatt atctatcgcg ggaatgatag tgtccgtttc gttttttgtgt | 1260 |
| ctttggtttg agatgggtaa tggtgcaaat tatgcatgtg ttcccgttgt gaatagacat | 1320 |
| cacagtggta ttgtgagtgg agttgtagga gcaatgggta acttaggagg cattttgttt | 1380 |
| agtttagtgt tcaggtacac tatatcaaat ggagtgaaca actacttcaa ggcgttttgg | 1440 |
| attataggaa ttgtttgcac tgctgtaaat ctggtctgtg tgcttattcc aattagagag | 1500 | gagaggccaa ggaaagcgga aaattga                                        1527

<210> SEQ ID NO 4
<211> LENGTH: 508
<212> TYPE: PRT
<213> ORGANISM: Pichia angusta

<400> SEQUENCE: 4

Met Gln Leu Ser Thr Leu Trp Glu Pro Pro Ile Val Asn Pro Arg Asn
 1               5                  10                  15

Leu Lys Ala Thr Ser Ile Pro Ile Phe Asn Leu Trp Asn Val Tyr Gly
             20                  25                  30

Arg Asn Phe Phe Phe Gly Trp Phe Gly Phe Val Ala Phe Leu Ser
         35                  40                  45

Trp Phe Ala Phe Pro Pro Leu Leu His Gly Met Leu Lys Lys Asp Leu
     50                  55                  60

Arg Leu Thr Ala Val Asp Ile Ser Asn Asn Ile Cys Gly Leu Thr
 65                  70                  75                  80

Gly Thr Leu Leu Gly Arg Phe Ile Leu Gly Pro Leu Asn Asp Lys Tyr
                 85                  90                  95

Gly Pro Arg Ile Thr Leu Ala Gly Val Leu Ala Gly Ala Ile Pro
            100                 105                 110

Thr Ala Phe Val Pro Leu Val Thr Asn Val Ala Gly Leu His Ala Ile
            115                 120                 125

Arg Phe Ser Ile Ser Phe Leu Gly Ser Ser Phe Ile Cys Cys Ser Gln
            130                 135                 140

Phe Cys Ala Val Phe Phe Asp Asn Asn Ile Val Gly Thr Ala Asn Ala
145                 150                 155                 160

Val Ser Ala Gly Trp Gly Asn Ala Gly Gly Val Ala Phe Phe Val
                165                 170                 175

Met Pro Ala Ile Ser Asn Ala Leu Glu Asn Arg Gly Tyr Ser Leu His
            180                 185                 190

His Ser Trp Ser Tyr Ser Phe Val Ile Gly Pro Phe Leu Ile Leu Met
            195                 200                 205

Ile Thr Ala Ile Leu Thr Phe Val Phe Gly Ser Asp Cys Pro Arg Gly
            210                 215                 220

Arg Trp Ser Leu Arg Gly Asp Thr Leu Gly Ile Asn Met Asp Asn Met
225                 230                 235                 240

Leu Val Lys Ser Val Ser Thr Thr Arg His Phe Pro Lys Glu Gly Glu
                245                 250                 255

Leu Thr Ser Val Phe Val Glu Pro Val Asn Ala Ile Asp Lys Ala Val
            260                 265                 270

Ser Glu Pro Asn Gln Asp Gln Glu Ile Leu Glu Val Ala Asp Ile Ile
            275                 280                 285

Asn Gly Asp Glu Ile Ile Glu Asp Pro Ser Leu Asn Asp Val Val Lys
            290                 295                 300

Ile Leu Leu Ser Pro Arg Thr Met Leu Val Gly Leu Cys Tyr Met Cys
305                 310                 315                 320

Ser Phe Gly Thr Glu Leu Ala Val Glu Ser Ile Ile Ser Asn Leu Phe
                325                 330                 335

Gly Gln Lys Met Thr Ser Trp Ser Thr Ser Lys Ala Gly Ala Trp Gly
            340                 345                 350

Ser Met Leu Gly Leu Leu Asn Val Val Ala Arg Pro Ala Gly Gly Ile
            355                 360                 365

```
Ile Ser Asp Phe Leu Tyr Gln Arg Phe Lys Thr Thr Lys Ala Lys Lys
            370                 375                 380

Phe Trp Met Ile Phe Thr Gly Leu Met Gln Gly Ile Phe Leu Ile Trp
385                 390                 395                 400

Ile Gly Leu Val Pro Glu Leu Ser Ile Ala Gly Met Ile Val Ser Val
                405                 410                 415

Ser Phe Leu Cys Leu Trp Phe Glu Met Gly Asn Gly Ala Asn Tyr Ala
            420                 425                 430

Cys Val Pro Val Val Asn Arg His His Ser Gly Ile Val Ser Gly Val
            435                 440                 445

Val Gly Ala Met Gly Asn Leu Gly Gly Ile Leu Phe Ser Leu Val Phe
        450                 455                 460

Arg Tyr Thr Ile Ser Asn Gly Val Asn Asn Tyr Phe Lys Ala Phe Trp
465                 470                 475                 480

Ile Ile Gly Ile Val Cys Thr Ala Val Asn Leu Val Cys Val Leu Ile
                485                 490                 495

Pro Ile Arg Glu Glu Arg Pro Arg Lys Ala Glu Asn
            500                 505
```

<210> SEQ ID NO 5
<211> LENGTH: 1527
<212> TYPE: DNA
<213> ORGANISM: Pichia angusta

<400> SEQUENCE: 5

```
atgcaactgt ctaccttatg ggaaccgcca acagtgaatc caagaaacct gaaagcgacc        60
tcaataccaa ttttttaacct atggaacgtc tatggaagaa acttcttttt cgggtggttt      120
ggttttttg ttgcttttct ttcttggttc gcgtttccgc ctcttctcca tggcatgttg       180
aagaaggacc taagactcac tgcagtggat atatccaata ataacatatg tggactgaca       240
ggaactttac taggcagatt cattttgggg cccctaacg acaagtatgg cccacggatt        300
actttgactg gcgtgctggt tgcaggagca atcccgactg catttgttcc tttggttaca       360
aatgttgcag tctacatgc cattcgcttt tttatcagct ttctaggctc tcgtttatt         420
tgctgctccc aattctgcgc tgtattttc gataacaaca ttatgggac agcaaatgcc         480
ctttctgccg ttggggaaa tgctggagga ggtgtggcat tctttgtcat gcctgccatt        540
tcaaatgcgt tggaaaatag aggttactct ttgcaccatt cttggagcta ctcttttgtg       600
attgggccgt tcttaatttt gatgatcacg gcaatactga tctctgtatt tggaagcgac       660
tgcccgagag gcagatggtc ccttcgtgga ataccttg gtatcaacat ggataatatg         720
ctcgtgaagt ctgtctctac cacaaggcac ttctctaagg aaggagagct cacttctgaa      780
tttggtgagc tgttaacgc aattgataag actgtggtcg agcccaatca agaccaggag       840
attcttgaag tcgcagatat cataaatggt gacgaaatca ttgaagaccc atcgctcaat      900
gacgtcgtca agatctgttt atccccgcgg acaatgctgg tcggactttg ctacatgtgc      960
tcgtttggta ctgagcttgc aattgagtct attatttcca acctgttcgg gcaaaagatg     1020
acaaactgga gcacctctaa agctggagca tgggctcaa tgcttggact cctgaacgtg      1080
gtggcaagac cagctggagg gatcatctcc gatttttat accaaagatt caaaaccgtc      1140
aaggctaaaa gttctggat gatcttcact ggcctgatgc agggcatttt ttgatttgg      1200
attggactag ttccggaatt atccatcgcg ggactcatag tgtccgtgtc gttttttggca     1260
ctttggttg agatgggtaa tggtgcaaat tatgcatgtg ttcccacgt gaatagacat       1320
cacagtggta ttgtgagtgg agttgtagga gcaatgggta acttaggagg catttttgttt     1380
```

```
agtttagtgt tcaggtacac tatatcaaat ggagtgaaca actacttcaa ggcgttttgg      1440
attataggaa ttgtttgcac tgctgtaaac ctggtctgtg tgcttgttcc aattagagag      1500
gagaggccac ataaagcgga aaattga                                          1527
```

<210> SEQ ID NO 6
<211> LENGTH: 508
<212> TYPE: PRT
<213> ORGANISM: Pichia angusta

<400> SEQUENCE: 6

```
Met Gln Leu Ser Thr Leu Trp Glu Pro Thr Val Asn Pro Arg Asn
  1               5                  10                  15

Leu Lys Ala Thr Ser Ile Pro Ile Phe Asn Leu Trp Asn Val Tyr Gly
                 20                  25                  30

Arg Asn Phe Phe Phe Gly Trp Phe Gly Phe Val Ala Phe Leu Ser
                 35                  40                  45

Trp Phe Ala Phe Pro Pro Leu Leu His Gly Met Leu Lys Lys Asp Leu
 50                  55                  60

Arg Leu Thr Ala Val Asp Ile Ser Asn Asn Ile Cys Gly Leu Thr
 65                  70                  75                  80

Gly Thr Leu Leu Gly Arg Phe Ile Leu Gly Pro Leu Asn Asp Lys Tyr
                 85                  90                  95

Gly Pro Arg Ile Thr Leu Thr Gly Val Leu Val Ala Gly Ala Ile Pro
                100                 105                 110

Thr Ala Phe Val Pro Leu Val Thr Asn Val Ala Gly Leu His Ala Ile
                115                 120                 125

Arg Phe Phe Ile Ser Phe Leu Gly Ser Ser Phe Ile Cys Cys Ser Gln
130                 135                 140

Phe Cys Ala Val Phe Phe Asp Asn Asn Ile Met Gly Thr Ala Asn Ala
145                 150                 155                 160

Leu Ser Ala Gly Trp Gly Asn Ala Gly Gly Gly Val Ala Phe Phe Val
                165                 170                 175

Met Pro Ala Ile Ser Asn Ala Leu Glu Asn Arg Gly Tyr Ser Leu His
                180                 185                 190

His Ser Trp Ser Tyr Ser Phe Val Ile Gly Pro Phe Leu Ile Leu Met
                195                 200                 205

Ile Thr Ala Ile Leu Ile Ser Val Phe Gly Ser Asp Cys Pro Arg Gly
210                 215                 220

Arg Trp Ser Leu Arg Gly Asp Thr Leu Gly Ile Asn Met Asp Asn Met
225                 230                 235                 240

Leu Val Lys Ser Val Ser Thr Thr Arg His Phe Ser Lys Glu Gly Glu
                245                 250                 255

Leu Thr Ser Glu Phe Gly Glu Pro Val Asn Ala Ile Asp Lys Thr Val
                260                 265                 270

Val Glu Pro Asn Gln Asp Gln Glu Ile Leu Glu Val Ala Asp Ile Ile
                275                 280                 285

Asn Gly Asp Glu Ile Ile Glu Asp Pro Ser Leu Asn Asp Val Val Lys
                290                 295                 300

Ile Cys Leu Ser Pro Arg Thr Met Leu Val Gly Leu Cys Tyr Met Cys
305                 310                 315                 320

Ser Phe Gly Thr Glu Leu Ala Ile Glu Ser Ile Ile Ser Asn Leu Phe
                325                 330                 335

Gly Gln Lys Met Thr Asn Trp Ser Thr Ser Lys Ala Gly Ala Trp Gly
                340                 345                 350
```

```
Ser Met Leu Gly Leu Leu Asn Val Val Ala Arg Pro Ala Gly Gly Ile
        355                 360                 365

Ile Ser Asp Phe Leu Tyr Gln Arg Phe Lys Thr Val Lys Ala Lys Lys
370                 375                 380

Phe Trp Met Ile Phe Thr Gly Leu Met Gln Gly Ile Phe Leu Ile Trp
385                 390                 395                 400

Ile Gly Leu Val Pro Glu Leu Ser Ile Ala Gly Leu Ile Val Ser Val
                405                 410                 415

Ser Phe Leu Ala Leu Trp Phe Glu Met Gly Asn Gly Ala Asn Tyr Ala
                420                 425                 430

Cys Val Pro His Val Asn Arg His Ser Gly Ile Val Ser Gly Val
                435                 440                 445

Val Gly Ala Met Gly Asn Leu Gly Gly Ile Leu Phe Ser Leu Val Phe
            450                 455                 460

Arg Tyr Thr Ile Ser Asn Gly Val Asn Asn Tyr Phe Lys Ala Phe Trp
465                 470                 475                 480

Ile Ile Gly Ile Val Cys Thr Ala Val Asn Leu Val Cys Val Leu Val
                485                 490                 495

Pro Ile Arg Glu Glu Arg Pro His Lys Ala Glu Asn
                500                 505

<210> SEQ ID NO 7
<211> LENGTH: 1527
<212> TYPE: DNA
<213> ORGANISM: Pichia angusta

<400> SEQUENCE: 7
atgcaactgt ctaccttatg ggaaccgcca atagtgaatc aagaaacct  gaaagcgacc      60 tcaataccaa ttttttaacct atggaacgtc tatggaagaa acttctttt  cgggtggttt     120 ggttttttg ttgcttttct ttcttggttc gcgtttccgc tcttctcca  tggcatgttg      180 aagaaggacc taagactcac tgcagtggat atatccaata ataacatatg tggactgaca     240
ggaactttac taggcagatt catttttggg cccttaacg  acaagtatgg cccacggatt     300
actttggctg gcgtgctggt tgcaggagca atcccgactg catttgttcc tttggttaca     360
aatgttgcag tctacatgc  cattcgcttt tttatcggct ttctaggctc ctcgtttatt     420
tgctgctccc aattctgcgc tgtatttttc gataacaaca ttatggggac agcaaatgcc     480
ctttctgccg gttgggaaaa tgctggagga ggtgtggcat ctttgtcat  gcctgccatt     540 tcaaatgcgt tggaaaatag aggttactcc ttgcaccatt cttggagcta ctcttttgtg     600
attgggccgt tcttaatttt gatgatcacg gcaatactga cctttgtatt tggaagcgac     660
tgcccgagag gcagatggtc ccttcgtgga gatacccttg gtatcaacat ggataatatg     720
ctcgtgaagt ctgtctctac cacaaggcac ttctctaagg aaggagagct cacttctgta     780
tttgttgagc ctgttaacgc aattgataag gctgtgtccg agcccaatca agaccaggaa     840
attcttgaag tcgcagatat cataaatggt gacgaaatca ttgaagaccc atcgctcaat     900
gacgtggtca agatcctttt atccccgcgg acaatgctgg tcggactttg ctacatgtgc     960
tcgtttggta ctgagcttgc ggtagagtct attatttcca acctgttcgg gcaaaagatg    1020
acaaactgga gcacctctaa agctggagca tggggctcaa tgcttggact cctgaacgtg    1080
gtggcaagac cagctggagg gatcatctcc gattttttat accaaagatt caaaaccgtc    1140
aaggctaaaa agttttggat gatcttcact ggcctgatgc agggcatttt tttgatttgg    1200
attggactag ttccggaatt atccatcgcg ggactcatag tgtccgtgtc gttttttggca   1260
```

```
cttggtttg agatgggtaa tggtgcaaat tatgcatgtg ttcccgttgt gaatagacat    1320
cacagtggta ttgtgagtgg agttgtagga gcaatgggta acttaggagg cattttgttt    1380
agtttagtgt tcaggtacac tatatcaaat ggagtgaaca actacttcaa ggcgttttgg    1440
attataggaa ttgtttgcac tgctgtaaca ctggtctgtg tgcttattcc aattagagag    1500
gagaggccaa ggaaagcgga aaattga                                        1527
```

<210> SEQ ID NO 8
<211> LENGTH: 508
<212> TYPE: PRT
<213> ORGANISM: Pichia angusta

<400> SEQUENCE: 8

```
Met Gln Leu Ser Thr Leu Trp Glu Pro Pro Ile Val Asn Pro Arg Asn
 1               5                  10                  15

Leu Lys Ala Thr Ser Ile Pro Ile Phe Asn Leu Trp Asn Val Tyr Gly
            20                  25                  30

Arg Asn Phe Phe Phe Gly Trp Phe Gly Phe Val Ala Phe Leu Ser
        35                  40                  45

Trp Phe Ala Phe Pro Pro Leu Leu His Gly Met Leu Lys Lys Asp Leu
    50                  55                  60

Arg Leu Thr Ala Val Asp Ile Ser Asn Asn Ile Cys Gly Leu Thr
65                  70                  75                  80

Gly Thr Leu Leu Gly Arg Phe Ile Leu Gly Pro Leu Asn Asp Lys Tyr
                85                  90                  95

Gly Pro Arg Ile Thr Leu Ala Gly Val Leu Val Ala Gly Ala Ile Pro
            100                 105                 110

Thr Ala Phe Val Pro Leu Val Thr Asn Val Ala Gly Leu His Ala Ile
            115                 120                 125

Arg Phe Phe Ile Gly Phe Leu Gly Ser Ser Phe Ile Cys Cys Ser Gln
        130                 135                 140

Phe Cys Ala Val Phe Phe Asp Asn Asn Ile Met Gly Thr Ala Asn Ala
145                 150                 155                 160

Leu Ser Ala Gly Trp Gly Asn Ala Gly Gly Val Ala Phe Phe Val
                165                 170                 175

Met Pro Ala Ile Ser Asn Ala Leu Glu Asn Arg Gly Tyr Ser Leu His
            180                 185                 190

His Ser Trp Ser Tyr Ser Phe Val Ile Gly Pro Phe Leu Ile Leu Met
        195                 200                 205

Ile Thr Ala Ile Leu Thr Phe Val Phe Gly Ser Asp Cys Pro Arg Gly
    210                 215                 220

Arg Trp Ser Leu Arg Gly Asp Thr Leu Gly Ile Asn Met Asp Asn Met
225                 230                 235                 240

Leu Val Lys Ser Val Ser Thr Thr Arg His Phe Ser Lys Glu Gly Glu
                245                 250                 255

Leu Thr Ser Val Phe Val Glu Pro Val Asn Ala Ile Asp Lys Ala Val
            260                 265                 270

Ser Glu Pro Asn Gln Asp Gln Glu Ile Leu Glu Val Ala Asp Ile Ile
        275                 280                 285

Asn Gly Asp Glu Ile Ile Glu Asp Pro Ser Leu Asn Asp Val Val Lys
    290                 295                 300

Ile Leu Leu Ser Pro Arg Thr Met Leu Val Gly Leu Cys Tyr Met Cys
305                 310                 315                 320

Ser Phe Gly Thr Glu Leu Ala Val Glu Ser Ile Ile Ser Asn Leu Phe
```

```
                   325                 330                 335
Gly Gln Lys Met Thr Asn Trp Ser Thr Ser Lys Ala Gly Ala Trp Gly
            340                 345                 350

Ser Met Leu Gly Leu Leu Asn Val Val Ala Arg Pro Ala Gly Gly Ile
            355                 360                 365

Ile Ser Asp Phe Leu Tyr Gln Arg Phe Lys Thr Val Lys Ala Lys Lys
            370                 375                 380

Phe Trp Met Ile Phe Thr Gly Leu Met Gln Gly Ile Phe Leu Ile Trp
385                 390                 395                 400

Ile Gly Leu Val Pro Glu Leu Ser Ile Ala Gly Leu Ile Val Ser Val
                405                 410                 415

Ser Phe Leu Ala Leu Trp Phe Glu Met Gly Asn Gly Ala Asn Tyr Ala
            420                 425                 430

Cys Val Pro Val Val Asn Arg His His Ser Gly Ile Val Ser Gly Val
            435                 440                 445

Val Gly Ala Met Gly Asn Leu Gly Gly Ile Leu Phe Ser Leu Val Phe
            450                 455                 460

Arg Tyr Thr Ile Ser Asn Gly Val Asn Asn Tyr Phe Lys Ala Phe Trp
465                 470                 475                 480

Ile Ile Gly Ile Val Cys Thr Ala Val Thr Leu Val Cys Val Leu Ile
                485                 490                 495

Pro Ile Arg Glu Glu Arg Pro Arg Lys Ala Glu Asn
            500                 505
```

<210> SEQ ID NO 9
<211> LENGTH: 1527
<212> TYPE: DNA
<213> ORGANISM: Artificial Sequence
<220> FEATURE:
<223> OTHER INFORMATION: maize codon optimized

<400> SEQUENCE: 9

```
atgcagttgt ctaccctctg ggagccaccg atcgtgaacc cgcggaacct caaggccacc        60
agcatcccga tcttcaacct ctggaacgtg tacggccgga acttcttctt cggctggttc       120
ggcttcttcg tggccttcct cagctggttc gctttccctc cgctcctgca tggtatgctc       180
aagaaggacc tccgcttgac tgccgtggac atcagcaaca caacatctg cggcctcacc        240
ggtactctcc tcggtcgctt cattctcggc ccactcaatg caagtacgg cccgcgcatc       300
accctcgctg tgttctcgt ggccggtgcc atcccgactg ctttcgttcc gctcgtgacc       360
aacgtggccg gcttgcatgc catccggttc ttcatcggct cctcggcag cagcttcatc       420
tgctgcagcc agttctgcgc cgtgttcttc gacaacaaca tcatgggcac cgccaacgcc       480
ttgtctgctg gctggggcaa tgccggtggc ggtgtggcct tcttcgttat gccggccatc       540
agcaatgccc tcgagaaccg cggctatagc ctccaccaca gctggagcta cagcttcgtg       600
atcggcccgt tcctcatcct catgatcacc gccatcttga ccttcgtgtt cggcagcgac       660
tgtccaagag gccgctggag cctccgcggc gacaccctcg catcaacat ggacaacatg        720
ctcgtgaaga gcgtgagcac caccagacac ttcagcaagg agggcgagct cactagcgtg       780
ttcgtggagc cggtgaacgc catcgacaag gctgttagcg agccgaatca ggaccaggag       840
atcctcgagg tggccgacat catcaacggc acgagatca tcgaggaccc gagcctcaac       900
gacgtggtta agatcctcct cagccctcgc accatgctcg tgggcctctg ctacatgtgc       960
agcttcggca ccgagctcgc tgttgagtct atcatcagca acctcttcgg ccagaagatg      1020
accaattgga gcaccagcaa ggctggtgcc tggggcagca tgctcggttt gctcaacgtg      1080
```

```
gtggccagac ctgctggcgg tatcattagc gacttcctct accagcgctt caagaccgtg    1140
aaggccaaga agttctggat gatcttcacc ggcctcatgc aaggcatctt cctcatctgg    1200
attggcctcg ttccagagct cagcatcgcc ggtctcatcg ttagcgtgag cttcctcgcc    1260
ctctggttcg agatgggtaa cggcgccaac tacgcctgcg tgccagtggt gaatcgccat    1320
catagcggca tcgtgtctgg cgttgtgggt gctatgggca atctcggcgg cattctcttc    1380
agcctcgtgt tccgctacac catcagcaac ggcgtgaaca actacttcaa ggccttctgg    1440
atcatcggca tcgtctgtac cgccgtgacc ctcgtctgtg tgttgatccc gatccgggag    1500
gagcgcccac gcaaggctga gaactag                                        1527

<210> SEQ ID NO 10
<211> LENGTH: 508
<212> TYPE: PRT
<213> ORGANISM: Pichia angusta
<220> FEATURE:
<223> OTHER INFORMATION: maize codon optimized

<400> SEQUENCE: 10
```

Met Gln Leu Ser Thr Leu Trp Glu Pro Pro Thr Val Asn Pro Arg Asn
 1               5                  10                  15

Leu Lys Ala Thr Ser Ile Pro Ile Phe Asn Leu Trp Asn Val Tyr Gly
            20                  25                  30

Arg Asn Phe Phe Phe Gly Trp Phe Gly Phe Val Ala Phe Leu Ser
        35                  40                  45

Trp Phe Ala Phe Pro Pro Leu Leu His Gly Met Leu Lys Lys Asp Leu
    50                  55                  60

Arg Leu Thr Ala Val Asp Ile Ser Asn Asn Ile Cys Gly Leu Thr
65                  70                  75                  80

Gly Thr Leu Leu Gly Arg Phe Ile Leu Gly Pro Leu Asn Asp Lys Tyr
                85                  90                  95

Gly Pro Arg Ile Cys Leu Thr Gly Val Leu Ala Gly Ala Ile Pro
            100                 105                 110

Thr Ala Phe Val Pro Leu Val Thr Asn Val Ala Gly Leu His Ala Ile
        115                 120                 125

Arg Phe Phe Ile Ser Phe Leu Gly Ser Ser Phe Ile Cys Cys Ser Gln
    130                 135                 140

Phe Cys Ala Val Phe Phe Asp Asn Asn Ile Val Gly Thr Ala Asn Ala
145                 150                 155                 160

Val Ser Ala Gly Trp Gly Asn Ala Gly Gly Gly Val Ala Phe Val
                165                 170                 175

Met Pro Ala Ile Ser Asn Ala Leu Glu Asn Arg Gly Tyr Ser Leu His
            180                 185                 190

His Ser Trp Ser Tyr Ser Phe Val Ile Gly Pro Phe Leu Ile Leu Met
        195                 200                 205

Ile Thr Ala Ile Leu Thr Phe Val Phe Gly Ser Asp Cys Pro Arg Gly
    210                 215                 220

Arg Trp Ser Leu Arg Gly Asp Thr Leu Gly Ile Asn Met Asp Asn Met
225                 230                 235                 240

Leu Val Lys Ser Val Ser Thr Thr Arg His Phe Ser Lys Glu Gly Glu
                245                 250                 255

Leu Thr Ser Val Phe Ala Glu Pro Val Asn Ala Ile Asp Lys Asn Val
            260                 265                 270

Val Glu Pro Asn Gln Asp Gln Glu Ile Leu Glu Val Ala Asp Ile Ile
        275                 280                 285

```
Asn Gly Asp Glu Ile Ile Glu Asp Pro Ser Pro Asn Asp Val Val Lys
    290                 295                 300

Ile Cys Leu Ser Pro Arg Thr Met Leu Val Gly Leu Cys Tyr Met Cys
305                 310                 315                 320

Ser Phe Gly Thr Glu Leu Ala Val Glu Ser Ile Ile Ser Asn Leu Phe
                325                 330                 335

Gly Gln Lys Met Thr Asn Trp Ser Thr Ser Lys Ala Gly Ala Trp Gly
            340                 345                 350

Ser Met Leu Gly Leu Leu Asn Val Val Ala Arg Pro Ala Gly Gly Ile
        355                 360                 365

Ile Ser Asp Phe Leu Tyr Gln Lys Phe Lys Thr Thr Lys Ala Lys Lys
    370                 375                 380

Phe Trp Met Ile Phe Thr Gly Leu Met Gln Gly Ile Phe Leu Ile Trp
385                 390                 395                 400

Ile Gly Leu Val Pro Glu Leu Ser Ile Ala Gly Ala Ile Val Ser Val
                405                 410                 415

Ser Phe Leu Cys Leu Trp Phe Glu Met Gly Asn Gly Ala Asn Tyr Ala
                420                 425                 430

Cys Val Pro His Val Asn Arg His His Ser Gly Ile Val Ser Gly Val
            435                 440                 445

Val Gly Ala Met Gly Asn Leu Gly Gly Ile Leu Phe Ser Leu Val Phe
        450                 455                 460

Arg Tyr Thr Ile Ser Asn Gly Val Asn Asn Tyr Phe Lys Ala Phe Trp
465                 470                 475                 480

Ile Ile Gly Ile Val Cys Thr Ala Val Asn Leu Val Cys Val Leu Val
                485                 490                 495

Pro Ile Arg Glu Glu Arg Pro Arg Lys Ala Glu Asn
                500                 505
```

<210> SEQ ID NO 11
<211> LENGTH: 1527
<212> TYPE: DNA
<213> ORGANISM: Pichia angusta

<400> SEQUENCE: 11

```
atgcaactgt ctaccttatg ggaaccgcca acagtgaatc caagaaacct gaaagcgacc       60
tcaataccaa ttttaaccct atggaacgtc tatggaagaa acttcttttt cgggtggttt      120
ggttttttg ttgcctttct ttcttggttc gcgtttccgc ctctcctcca tggcatgttg      180
aagaaggacc taagactcac tgcagtggat atatccaata ataacatatg tggactgaca      240
ggaacttttac taggcagatt cattttgggg cccttaacg acaagtatgg cccacggatt       300
tgtttgacag gcgtgctggt tgcaggagca attccgactg catttgttcc tttggttaca      360
aatgttgcag gtctacatgc cattcgcttt tttatcagct ttctaggctc ctcgtttatt      420
tgctgctccc aattctgcgc tgtatttttt gataacaaca ttgtggggac agcaaatgcc      480
gtctctgccg gttggggaaa tgctggagga ggtgtggcat ctttgtcat gcctgccatt      540
tcaaatgcgt tggaaaatag aggttactct tgcaccatt cttggagcta ctcttttgtg      600
attgggccgt tcttaatttt gatgatcacg gcaatactga cctttgtatt tggaagcgac      660
tgcccgagag gcagatggtc ccttcgtgga gataccctttg gtatcaacat ggataatatg      720
ctcgtgaagt ctgtctctac cacaaggcac ttctctaagg aaggagagct cacttctgta      780
tttgccgagc ctgttaacgc aattgataag aacgtggttg agcccaatca agaccaggag      840
attcttgaag tcgcagatat cataaatggt gacgaaatca ttgaagaccc atcgcccaat      900
```

```
gacgtcgtca agatctgttt atccccgcgg acaatgctgg tcggactttg ctacatgtgc    960
tcgtttggta ctgagcttgc ggtagagtct attatttcca acctgttcgg gcaaaagatg   1020
acaaactgga gcacctctaa agctggggca tggggctcaa tgcttggact cctgaacgtg   1080
gtggcaagac cagctggagg gatcatctcc gatttttat accaaaaatt caaaaccaca   1140
aaggctaaaa agttctggat gatcttcact ggcctgatgc agggcatttt tttgatttgg   1200
attggactag ttccggaatt atccatcgcg ggagcaatag tgtccgtttc gttttgtgt   1260
ctttggtttg agatgggtaa tggtgcaaat tatgcatgtg ttccccacgt gaatagacat   1320
cacagtggta ttgtgagtgg agttgtagga gcaatgggta acttaggagg cattttgttt   1380
agtttagtgt tcaggtacac tatatcaaat ggagtgaaca actacttcaa ggcgttttgg   1440
attataggaa ttgtttgcac tgctgtaaac ctggtctgtg tgcttgttcc aattagagag   1500
gagaggccaa ggaaagcgga aaattga                                       1527

<210> SEQ ID NO 12
<211> LENGTH: 2865
<212> TYPE: DNA
<213> ORGANISM: Porphyra perforata

<400> SEQUENCE: 12
atggaggctg cttctggtgc cctcagtgag ctccggttgg agaagggggt taagggctgg     60
gacccggtca aggtgcccgg ccggagctcc ctcaagagca cgcctatcgc caccccagag    120
ggctccctcc gcggtggctc cctctacacg gcccggtcgc agcacgcggc tggcgccaac    180
gacgtcatgg cggccaatgg ggtgtcggcg tcgagcaccg cgtcggggtt gagctttgct    240
ccttcggacg gcagtggcag tggcagtggc gcgtcgggt ggacggagct gaacgatgct    300
ctgaacgcca agctcgcgtc caagtcgacg atgttggaca gcagcacgt tgcggacgag    360
gtggatgacc gggacgtcaa gacgccagac aactggatcc ccgccaccc ggccttgatc    420
cgtctgacgg gcaagcaccc gttcaactgt gaggcgccgc tgtcgatgct ggtggatcag    480
ggttttatca cccccccatc tctgcacttt gtgcgcaacc acggggctgc accgcagctg    540
tcttttgacg accaccggct ggaggtgacc ggcctcgtcg acactccttt gacgttgtcc    600
atggctgaca tcttggccat gccgagcgtc accatcccgg tcacgctgac gtgcgcggga    660
aaccggcgga aggagcagaa catgacaaag cagacgattg gcttctcgtg gggcgccgcc    720
gccaccagct gcaacttttg gactggcgtg cgcgtacggg atgtgcttca aaaggcgggc    780
atccagatgg acaaggcgcg ccatgtttgc tttgtgggct gtgacaacct gccgggggc    840
aagtacggca cgtcggttga cctggcgacg gccatggacc agttcgggga ggtgatgctt    900
gcgtacgagc agaacggcat ccgcctcacg cccgaccacg gcgcgcccct gcgggtggta    960
attcctgggt ggattggcgg ccgcatggta agtgggtga ccggcctgtc ggtaacgtcg   1020
gaagagtcgc aggagcacta tcactttttt gataaccgca tcctgccacc acacgtggac   1080
gcggagctgg ccaagtctga gggctggtgg tacaagcgcg agtacctgtt caaccagctc   1140
aatatcaact ctgccatcag ctctcctgcc aatggcgaac tgatgtccct gtcgggcgcg   1200
ggggtgtaca ccctcaaggg ttacgcctac tctggcggcg ccgcaaggt cacccgtgtg   1260
gaggtgtcgg tggacggcgg caagacttgg ctgctggcca cgttgaccca ccccgaggag   1320
cggcactcgc acgctccgtc gtatggtcgc tattactgct ggtgcttctg ggagtacacc   1380
attgataagt ttgcgctgct caacgcgcg actagttcgg gcgagttgct ggtgcgtgcg   1440
tgggatgagg gcaacaatac ccagcccgcc aagctgacct ggaacttgat gggtatgggc   1500
```

| | |
|---|---|
| aacaactgct acttccgcgt gacggtggcg cccaagcagt cgtcgggtga atttgcgctc | 1560 |
| gagtttctcc acccgacggt ggcgggcccc gcggagggtg gctggatgcc gccaccgcag | 1620 |
| gagtcggtag ttgcggctgc cgccgcgcg ggagtagcag agacactgaa gcggaccaaa | 1680 |
| tcggcgccgc agatgaacaa gatggaccag caggactcca agacgattac catggaggag | 1740 |
| gtggccaagc acgacacgga agaggactcg tggattgtgg tgcacaacaa ggtgtatgac | 1800 |
| tgtacgcctt tccttaagga ccaccccggt ggtggcgcca gcattgtgat gaacgcgggt | 1860 |
| gcggactgca cggaggagtt tgatgcgatc cactcaacca aggccaagtc catgctggac | 1920 |
| gactactata ttggcgaact ggccgttgag gacattgagg acgagccgga gcaaccagcc | 1980 |
| ctgcacctgt ccaagtcgtc ggtgcagctg atgaaggatg acttcaaaga gcagagcgtg | 2040 |
| cgtaaggctg tggagggtgt ggacgaggag gtcgtgacgc cggtggcact taaccccaag | 2100 |
| aagtggattc actttccgct catccagaag gaggagttga gccatgacac gcggcgcttc | 2160 |
| cgctttgggc tccccactcc tggccaccgg ttgggcctgc ctgtgggctt ccacatgttc | 2220 |
| ttgatggcca ccattgacgg tgcaatggtc atgcgggcat acacaccgac gtcgtcggac | 2280 |
| gcagagctgg gctacttcga cctggtcatc aaggtgtact tgcaaacgt gcaccccagg | 2340 |
| ttccctgacg gtggtaagct cacccagtac atggaggaga tgtcgctggg cgacgagatt | 2400 |
| cgcgtcaagg gcccgcttgg ccacattgag taccgtagcc gcggcgagat gaccattgac | 2460 |
| ggcaagccgc ggacggtaag tgccctgacg ggcctgatgg cgggcagtgg catcacgccc | 2520 |
| ttttaccaga ttctccaggc tgtcatggcc gacccgaggg acaagaccga gctgtacctc | 2580 |
| atctatgcca accagacacc ggaggatgtg ctgctgcggt cagagctgga caagatggcg | 2640 |
| gcagagcgcg acaacatcca tgtctggtac acatgcgacc gcgcgccgga ggactggaag | 2700 |
| tatgacattg gcttcatgac ggtagacatg atcaaggagc atggggcgcc ggcaggcccc | 2760 |
| gatgtgttgg gcctgtcgtg cggaccgccg ccatttatca agtttgcggc gaccccgagc | 2820 |
| ttgaccaaga acggctatgc ggaggagaac cagttcttgt tttag | 2865 |

<210> SEQ ID NO 13
<211> LENGTH: 2865
<212> TYPE: DNA
<213> ORGANISM: Porphyra perforata

<400> SEQUENCE: 13

| | |
|---|---|
| atggaggctg cttctggtgc cctcagtgag ctccggttgg agaagggggt taagggctgg | 60 |
| gacccggtca aggtgcccgg ccggagctcc ctcaagagca cgcctatcgc caccccagag | 120 |
| ggctccctcc gcggtggctc cctctacacg gcccggtcgc agcacgcggc tggcgccaac | 180 |
| gacgtcatgg cggccaatgg ggtgtcggcg tcgagcaccg cgtcgggggtt gagctttgct | 240 |
| ccttcggacg gcagtggcag tggcagtggc cgcgtcgggt ggacggagct gaacgatgct | 300 |
| ctgaacgcca agctcgcgtc caagtcgacg atgttggaca gcagcacgt tgcggacgag | 360 |
| gtggatgacc gggacgtcaa gacgccagac aactggatcc cccgccaccc ggccttgatc | 420 |
| cgtctgacgg gcaagcaccc gttcaactgt gaggcgccgc tgtcgatgct ggtggatcag | 480 |
| ggttttatca ccccccatc tctgcacttt gtgcgcaacc acggggctgc accgcagctg | 540 |
| tcttttgacg accaccggct ggaggtgacc ggcctcgtcg acactccttt gacgttgtcc | 600 |
| atggctgaca tcttggccat gccgagcgtc accatcccgg tcacgctgac gtgcgcggga | 660 |
| aaccggcgga aggagcagaa catgacaaag cagacgattg gcttctcgtg gggcgccgcc | 720 |
| gccaccagct gcaactttgt gactggcgtg cgcgtacggg atgtgcttca aaaggcgggc | 780 |

```
atccagatgg acaaggcgcg ccatgtttgc tttgtgggct gtgacaacct gccgggggc      840
aagtacggca cgtcggttga cctggcgacg gccatggacc agttcgggga ggtgatgctt      900
gcgtacgagc agaacggcat ccgcctcacg cccgaccacg gcgcgcccct gcgggtggta      960
attcctgggt ggattggcgg ccgcatggtg aagtgggtga ccggcctgtc ggtaacgtcg     1020
gaagagtcgc aggagcacta tcactttttt gataaccgca tcctgccacc acacgtggac     1080
gcggagctgg ccaagtctga gggctggtgg tacaagcgcg agtacctgtt caaccagctc     1140
aatatcaact ctgccatcag ctctcctgcc aatggcgaac tgatgtccct gtcgggcgcg     1200
ggggtgtaca ccctcaaggg ttacgcctac tctggcggcg ccgcaaggt cacccgtgtg      1260
gaggtgtcgg tggacggcgg caagacttgg ctgctggcca cgttggacca ccccgaggag     1320
cggcactcgc acgctccgtc gtatggtcgc tattactgct ggtgcttctg ggagtacacc     1380
attgataagt ttgcgctgct caacgcggcg actagttcgg gcgagttgct ggtgcgtgcg     1440
tgggatgagg gcaacaatac ccagcccgcc aagctgacct ggaacttgat gggtatgggc     1500
aacaactgct acttccgcgt gacggtggcg cccaagcagt cgtcgggtga atttgcgctc     1560
gagtttctcc acccgacggt ggcgggcccc gcggagggtg gctggatgcc gccaccgcag     1620
gagtcggtag ttgcggctgc cgccgcggcg gcagtagcag agacactgaa gcggaccaaa     1680
tcggcgccgc agatgaacaa gatgaccag caggactcca agacgattac catggaggag      1740
gtggccaagc acgacacgga agaggactcg tggattgtgg tgcacaacaa ggtgtatgac     1800
tgtacgcctt tccttaagga ccaccccggt ggtggcgcca gcattgtgat gaacgcgggt     1860
gcggactgca cggaggagtt tgatgcgatc cactcaacca aggccaagtc catgctggac     1920
gactactata ttggcgaact ggccgttgag gacattgagg acgagccgga gcaaccagcc     1980
ctgcacctgt ccaagtcgtc ggtgcagctg atgaaggatg acttcaaaga gcagagcgtg     2040
cgtaaggctg tggagggtgt ggacgaggag gtcgtgacgc cggtggcact taaccccaag     2100
aagtggattc acttttccgct catccagaag gaggagttga gccatgacac gcggcgcttc     2160
cgctttgggc tccccactcc tggccaccgg ttgggcctgc ctgtgggctt ccacatgttc     2220
ttgatggcca ccattgacgg tgcaatggtc atgcgggcat acacaccgac gtcgtcggac     2280
gcagagctgg gctacttcga cctggtcatc aaggtgtact ttgcaaacgt gcaccccagg     2340
ttccctgacg gtggtaagct cacccagtac atggaggaga tgtcgctggg cgacgagatt     2400
cgcgtcaagg gcccgcttgg ccacattgag taccgtagcc gcggcgagat gaccattgac     2460
ggcaagccgc ggacggtaag tgccctgacg ggcctgatgg cgggcagtgg catcacgccc     2520
ttttaccaga ttctccaggc tgtcatggcc gaccccgagg acaagaccga gctgtacctc     2580
atctatgcca accagacacc ggaggatgtg ctgctgcggt cagagctgga caagatggcg     2640
gcagagcgcg acaacatcca tgtctggtac acatgcgacc gcgcgccgga ggactggaag     2700
tatgacattg gcttcatgac ggtagacatg atcaaggagc atgggcgcgc ggcaggcccc     2760
gatgtgttgg gcctgtcgtg cggaccgccg ccatttatca agtttgcggc gaccccgagc     2820
ttgaccaaga acggctatgc ggaggagaac cagttcttgt tttag                    2865
```

<210> SEQ ID NO 14
<211> LENGTH: 954
<212> TYPE: PRT
<213> ORGANISM: Porphyra perforata

<400> SEQUENCE: 14

Met Glu Ala Ala Ser Gly Ala Leu Ser Glu Leu Arg Leu Glu Lys Gly

-continued

```
  1               5                  10                 15
Val Lys Gly Trp Asp Pro Val Lys Val Pro Gly Arg Ser Ser Leu Lys
                 20                  25                 30

Ser Thr Pro Ile Ala Thr Pro Glu Gly Ser Leu Arg Gly Gly Ser Leu
                 35                  40             45

Tyr Thr Ala Arg Ser Gln His Ala Ala Gly Ala Asn Asp Val Met Ala
     50                  55                  60

Ala Asn Gly Val Ser Ala Ser Ser Thr Ala Ser Gly Leu Ser Phe Ala
 65                  70                  75                  80

Pro Ser Asp Gly Ser Gly Ser Gly Ser Gly Arg Val Gly Trp Thr Glu
                     85                  90                 95

Leu Asn Asp Ala Leu Asn Ala Lys Leu Ala Ser Lys Ser Thr Met Leu
                100                 105                110

Asp Lys Gln His Val Ala Asp Glu Val Asp Asp Arg Asp Val Lys Thr
                115                 120                 125

Pro Asp Asn Trp Ile Pro Arg His Pro Ala Leu Ile Arg Leu Thr Gly
            130                 135                 140

Lys His Pro Phe Asn Cys Glu Ala Pro Leu Ser Met Leu Val Asp Gln
145                 150                 155                 160

Gly Phe Ile Thr Pro Pro Ser Leu His Phe Val Arg Asn His Gly Ala
                165                 170                 175

Ala Pro Gln Leu Ser Phe Asp Asp His Arg Leu Glu Val Thr Gly Leu
                180                 185                 190

Val Asp Thr Pro Leu Thr Leu Ser Met Ala Asp Ile Leu Ala Met Pro
                195                 200                 205

Ser Val Thr Ile Pro Val Thr Leu Thr Cys Ala Gly Asn Arg Arg Lys
210                 215                 220

Glu Gln Asn Met Thr Lys Gln Thr Ile Gly Phe Ser Trp Gly Ala Ala
225                 230                 235                 240

Ala Thr Ser Cys Asn Phe Trp Thr Gly Val Arg Val Arg Asp Val Leu
                245                 250                 255

Gln Lys Ala Gly Ile Gln Met Asp Lys Ala Arg His Val Cys Phe Val
                260                 265                 270

Gly Cys Asp Asn Leu Pro Gly Gly Lys Tyr Gly Thr Ser Val Asp Leu
            275                 280                 285

Ala Thr Ala Met Asp Gln Phe Gly Glu Val Met Leu Ala Tyr Glu Gln
                290                 295                 300

Asn Gly Ile Arg Leu Thr Pro Asp His Gly Ala Pro Leu Arg Val Val
305                 310                 315                 320

Ile Pro Gly Trp Ile Gly Gly Arg Met Val Lys Trp Val Thr Gly Leu
                325                 330                 335

Ser Val Thr Ser Glu Glu Ser Gln Glu His Tyr His Phe Phe Asp Asn
                340                 345                 350

Arg Ile Leu Pro Pro His Val Asp Ala Glu Leu Ala Lys Ser Glu Gly
            355                 360                 365

Trp Trp Tyr Lys Arg Glu Tyr Leu Phe Asn Gln Leu Asn Ile Asn Ser
370                 375                 380

Ala Ile Ser Ser Pro Ala Asn Gly Glu Leu Met Ser Leu Ser Gly Ala
385                 390                 395                 400

Gly Val Tyr Thr Leu Lys Gly Tyr Ala Tyr Ser Gly Gly Gly Arg Lys
                405                 410                 415

Val Thr Arg Val Glu Val Ser Val Asp Gly Gly Lys Thr Trp Leu Leu
                420                 425                 430
```

```
Ala Thr Leu Asp His Pro Glu Glu Arg His Ser His Ala Pro Ser Tyr
        435                 440                 445

Gly Arg Tyr Tyr Cys Trp Cys Phe Trp Glu Tyr Thr Ile Asp Lys Phe
450                 455                 460

Ala Leu Leu Asn Ala Ala Thr Ser Ser Gly Glu Leu Leu Val Arg Ala
465                 470                 475                 480

Trp Asp Glu Gly Asn Asn Thr Gln Pro Ala Lys Leu Thr Trp Asn Leu
                485                 490                 495

Met Gly Met Gly Asn Asn Cys Tyr Phe Arg Val Thr Val Ala Pro Lys
            500                 505                 510

Gln Ser Ser Gly Glu Phe Ala Leu Glu Phe Leu His Pro Thr Val Ala
        515                 520                 525

Gly Pro Ala Glu Gly Gly Trp Met Pro Pro Gln Glu Ser Val Val
    530                 535                 540

Ala Ala Ala Ala Ala Gly Val Ala Glu Thr Leu Lys Arg Thr Lys
545                 550                 555                 560

Ser Ala Pro Gln Met Asn Lys Met Asp Gln Gln Asp Ser Lys Thr Ile
                565                 570                 575

Thr Met Glu Glu Val Ala Lys His Asp Thr Glu Glu Asp Ser Trp Ile
            580                 585                 590

Val Val His Asn Lys Val Tyr Asp Cys Thr Pro Phe Leu Lys Asp His
        595                 600                 605

Pro Gly Gly Gly Ala Ser Ile Val Met Asn Ala Gly Ala Asp Cys Thr
    610                 615                 620

Glu Glu Phe Asp Ala Ile His Ser Thr Lys Ala Lys Ser Met Leu Asp
625                 630                 635                 640

Asp Tyr Tyr Ile Gly Glu Leu Ala Val Glu Asp Ile Glu Asp Glu Pro
                645                 650                 655

Glu Gln Pro Ala Leu His Leu Ser Lys Ser Ser Val Gln Leu Met Lys
            660                 665                 670

Asp Asp Phe Lys Glu Gln Ser Val Arg Lys Ala Val Glu Gly Val Asp
        675                 680                 685

Glu Glu Val Val Thr Pro Val Ala Leu Asn Pro Lys Lys Trp Ile His
    690                 695                 700

Phe Pro Leu Ile Gln Lys Glu Glu Leu Ser His Asp Thr Arg Arg Phe
705                 710                 715                 720

Arg Phe Gly Leu Pro Thr Pro Gly His Arg Leu Gly Leu Pro Val Gly
                725                 730                 735

Phe His Met Phe Leu Met Ala Thr Ile Asp Gly Ala Met Val Met Arg
            740                 745                 750

Ala Tyr Thr Pro Thr Ser Ser Asp Ala Glu Leu Gly Tyr Phe Asp Leu
        755                 760                 765

Val Ile Lys Val Tyr Phe Ala Asn Val His Pro Arg Phe Pro Asp Gly
    770                 775                 780

Gly Lys Leu Thr Gln Tyr Met Glu Glu Met Ser Leu Gly Asp Glu Ile
785                 790                 795                 800

Arg Val Lys Gly Pro Leu Gly His Ile Glu Tyr Arg Ser Arg Gly Glu
                805                 810                 815

Met Thr Ile Asp Gly Lys Pro Arg Thr Val Ser Ala Leu Thr Gly Leu
            820                 825                 830

Met Ala Gly Ser Gly Ile Thr Pro Phe Tyr Gln Ile Leu Gln Ala Val
        835                 840                 845

Met Ala Asp Pro Glu Asp Lys Thr Glu Leu Tyr Leu Ile Tyr Ala Asn
    850                 855                 860
```

```
Gln Thr Pro Glu Asp Val Leu Leu Arg Ser Glu Leu Asp Lys Met Ala
865                 870                 875                 880

Ala Glu Arg Asp Asn Ile His Val Trp Tyr Thr Cys Asp Arg Ala Pro
                885                 890                 895

Glu Asp Trp Lys Tyr Asp Ile Gly Phe Met Thr Val Asp Met Ile Lys
            900                 905                 910

Glu His Gly Ala Pro Ala Gly Pro Asp Val Leu Gly Leu Ser Cys Gly
        915                 920                 925

Pro Pro Pro Phe Ile Lys Phe Ala Ala Thr Pro Ser Leu Thr Lys Asn
    930                 935                 940

Gly Tyr Ala Glu Glu Asn Gln Phe Leu Phe
945                 950

<210> SEQ ID NO 15
<211> LENGTH: 954
<212> TYPE: PRT
<213> ORGANISM: Porphyra perforata

<400> SEQUENCE: 15

Met Glu Ala Ala Ser Gly Ala Leu Ser Glu Leu Arg Leu Glu Lys Gly
1               5                   10                  15

Val Lys Gly Trp Asp Pro Val Lys Val Pro Gly Arg Ser Ser Leu Lys
            20                  25                  30

Ser Thr Pro Ile Ala Thr Pro Glu Gly Ser Leu Arg Gly Gly Ser Leu
        35                  40                  45

Tyr Thr Ala Arg Ser Gln His Ala Ala Gly Ala Asn Asp Val Met Ala
    50                  55                  60

Ala Asn Gly Val Ser Ala Ser Ser Thr Ala Ser Gly Leu Ser Phe Ala
65                  70                  75                  80

Pro Ser Asp Gly Ser Gly Ser Gly Ser Gly Arg Val Gly Trp Thr Glu
                85                  90                  95

Leu Asn Asp Ala Leu Asn Ala Lys Leu Ala Ser Lys Ser Thr Met Leu
            100                 105                 110

Asp Lys Gln His Val Ala Asp Glu Val Asp Asp Arg Ala Val Lys Thr
        115                 120                 125

Pro Asp Asn Trp Ile Pro Arg His Pro Ala Leu Ile Arg Leu Thr Gly
    130                 135                 140

Lys His Pro Phe Asn Cys Glu Ala Pro Leu Ser Met Leu Val Asp Gln
145                 150                 155                 160

Gly Phe Ile Thr Pro Pro Ser Leu His Phe Val Arg Asn His Gly Ala
                165                 170                 175

Ala Pro Gln Leu Ser Phe Asp Asp His Arg Leu Glu Val Thr Gly Leu
            180                 185                 190

Val Asp Thr Pro Leu Thr Leu Ser Met Ala Asp Ile Leu Ala Met Pro
        195                 200                 205

Ser Val Thr Ile Pro Val Thr Leu Thr Cys Ala Gly Asn Arg Arg Lys
    210                 215                 220

Glu Gln Asn Met Thr Lys Gln Thr Ile Gly Phe Ser Trp Gly Ala Ala
225                 230                 235                 240

Ala Thr Ser Cys Asn Phe Trp Thr Gly Val Arg Val Arg Asp Val Leu
                245                 250                 255

Gln Lys Ala Gly Ile Gln Met Asp Lys Ala Arg His Val Cys Phe Val
            260                 265                 270

Gly Cys Asp Asn Leu Pro Gly Gly Lys Tyr Gly Thr Ser Val Asp Leu
        275                 280                 285
```

```
Ala Thr Ala Met Asp Gln Phe Gly Glu Val Met Leu Ala Tyr Glu Gln
    290                 295                 300

Asn Gly Ile Arg Leu Thr Pro Asp His Gly Ala Pro Leu Arg Val Val
305                 310                 315                 320

Ile Pro Gly Trp Ile Gly Gly Arg Met Val Lys Trp Val Thr Gly Leu
                325                 330                 335

Ser Val Thr Ser Glu Glu Ser Gln Glu His Tyr His Phe Phe Asp Asn
            340                 345                 350

Arg Ile Leu Pro Pro His Val Asp Ala Glu Leu Ala Lys Ser Glu Gly
        355                 360                 365

Trp Trp Tyr Lys Arg Glu Tyr Leu Phe Asn Gln Leu Asn Ile Asn Ser
    370                 375                 380

Ala Ile Ser Ser Pro Ala Asn Gly Glu Leu Met Ser Leu Ser Gly Ala
385                 390                 395                 400

Gly Val Tyr Thr Leu Lys Gly Tyr Ala Tyr Ser Gly Gly Arg Lys
                405                 410                 415

Val Thr Arg Val Glu Val Ser Val Asp Gly Gly Lys Thr Trp Leu Leu
            420                 425                 430

Ala Thr Leu Asp His Pro Glu Glu Arg His Ser His Ala Pro Ser Tyr
        435                 440                 445

Gly Arg Tyr Tyr Cys Trp Cys Phe Trp Glu Tyr Thr Ile Asp Lys Phe
    450                 455                 460

Ala Leu Leu Asn Ala Ala Thr Ser Ser Gly Glu Leu Leu Val Arg Ala
465                 470                 475                 480

Trp Asp Glu Gly Asn Asn Thr Gln Pro Ala Lys Leu Thr Trp Asn Leu
                485                 490                 495

Met Gly Met Gly Asn Asn Cys Tyr Phe Arg Val Thr Val Ala Pro Lys
            500                 505                 510

Gln Ser Ser Gly Glu Phe Ala Leu Glu Phe Leu His Pro Thr Val Ala
        515                 520                 525

Gly Pro Ala Glu Gly Gly Trp Met Pro Pro Gln Glu Ser Val Val
    530                 535                 540

Ala Ala Ala Ala Ala Ala Val Ala Glu Thr Leu Lys Arg Thr Lys
545                 550                 555                 560

Ser Ala Pro Gln Met Asn Lys Met Asp Gln Gln Asp Ser Lys Thr Ile
                565                 570                 575

Thr Met Glu Glu Val Ala Lys His Asp Thr Glu Glu Asp Ser Trp Ile
            580                 585                 590

Val Val His Asn Lys Val Tyr Asp Cys Thr Pro Phe Leu Lys Asp His
        595                 600                 605

Pro Gly Gly Gly Ala Ser Ile Val Met Asn Ala Gly Ala Asp Cys Thr
    610                 615                 620

Glu Glu Phe Asp Ala Ile His Ser Thr Lys Ala Lys Ser Met Leu Asp
625                 630                 635                 640

Asp Tyr Tyr Ile Gly Glu Leu Ala Val Glu Asp Ile Glu Asp Glu Pro
                645                 650                 655

Glu Gln Pro Ala Leu His Leu Ser Lys Ser Ser Val Gln Leu Met Lys
            660                 665                 670

Asp Asp Phe Lys Glu Gln Ser Val Arg Lys Ala Val Glu Gly Val Asp
        675                 680                 685

Glu Glu Val Val Thr Pro Val Ala Leu Asn Pro Lys Lys Trp Ile His
    690                 695                 700

Phe Pro Leu Ile Gln Lys Glu Glu Leu Ser His Asp Thr Arg Arg Phe
```

```
                    705                 710                 715                 720
Arg Phe Gly Leu Pro Thr Pro Gly His Arg Leu Gly Leu Pro Val Gly
                    725                 730                 735

Phe His Met Phe Leu Met Ala Thr Ile Asp Gly Ala Met Val Met Arg
                740                 745                 750

Ala Tyr Thr Pro Thr Ser Ser Asp Ala Glu Leu Gly Tyr Phe Asp Leu
            755                 760                 765

Val Ile Lys Val Tyr Phe Ala Asn Val His Pro Arg Phe Pro Asp Gly
        770                 775                 780

Gly Lys Leu Thr Gln Tyr Met Glu Glu Met Ser Leu Gly Asp Glu Ile
785                 790                 795                 800

Arg Val Lys Gly Pro Leu Gly His Ile Glu Tyr Arg Ser Arg Gly Glu
                805                 810                 815

Met Thr Ile Asp Gly Lys Pro Arg Thr Val Ser Ala Leu Thr Gly Leu
                820                 825                 830

Met Ala Gly Ser Gly Ile Thr Pro Phe Tyr Gln Ile Leu Gln Ala Val
                835                 840                 845

Met Ala Asp Pro Glu Asp Lys Thr Glu Leu Tyr Leu Ile Tyr Ala Asn
850                 855                 860

Gln Thr Pro Glu Asp Val Leu Leu Arg Ser Glu Leu Asp Lys Met Ala
865                 870                 875                 880

Ala Glu Arg Asp Asn Ile His Val Trp Tyr Thr Cys Asp Arg Ala Pro
                885                 890                 895

Glu Asp Trp Lys Tyr Asp Ile Gly Phe Met Thr Val Asp Met Ile Lys
                900                 905                 910

Glu His Gly Ala Pro Ala Gly Pro Asp Val Leu Gly Leu Ser Cys Gly
                915                 920                 925

Pro Pro Pro Phe Ile Lys Phe Ala Ala Thr Pro Ser Leu Thr Lys Asn
    930                 935                 940

Gly Tyr Ala Glu Glu Asn Gln Phe Leu Phe
945                 950

<210> SEQ ID NO 16
<211> LENGTH: 2865
<212> TYPE: DNA
<213> ORGANISM: Porphyra perforata

<400> SEQUENCE: 16
atggaagctg ccagcggcgc tctttcggaa ctgcgcttgg agaagggtgt taagggctgg      60
gacccggtta aggttcctgg caggtcaagc ttgaagagca cgcccatcgc tactcccgag     120
ggctcactcc gcggtggctc tctgtacaca gcgaggtcac aacatgctgc gggcgctaat     180
gacgttatgg ctgccaatgg tgtctctgcg tcttctacgg ccagcgggct gtctttcgct     240
ccttccgatg gttccggtag cggtagcggt cgcgtgggtt ggaccgaact caatgatgcg     300
ctcaacgcta agctggcctc caagtccacc atgctcgata gcagcacgt ggcggacgag      360 gttgatgacc gggacgtgaa gactccggac aactggattc cgcgccatcc tgccctcatc     420
cgcctgaccg ggaagcatcc tttcaactgc gaggctccgc tgtccatgct ggtggatcaa     480
gggttcatca cgccgccgag cctccacttc gttaggaatc acggcgctgc tccgcagttg     540
tccttcgacg accaccgctt ggaggtgact ggccttgtgg acactccgct gactttgagc     600
atggccgata tccttgcgat gccgagcgtc actattcccg tgactcttac ctgcgctggc     660
aaccggcgga aggagcagaa catgaccaag cagacgatcg gcttctcgtg gggtgccgct     720
gcgacctctt gcaacttctg gactggcgtg agggtgcggg atgttcttca gaaggctggc     780
```

```
atccagatgg ataaggcccg ccacgtctgc ttcgttggct gtgacaatct cccgggtggc    840
aagtatggga cgtcggtgga cctggctacc gctatggacc agttcggcga ggtgatgctg    900
gcgtacgagc agaatggcat tcgcctcacg ccagaccacg gtgcccctct tcgcgttgtt    960
atccctgggt ggattggcgg caggatggtt aagtgggtca caggcctcag cgtcactagc   1020
gaggagtccc aggagcacta ccacttcttc gacaaccgca tcttgccgcc tcacgtcgat   1080
gctgaacttg ccaagtccga aggctggtgg tacaagcgcg agtacctctt caaccagctc   1140
aacatcaaca gcgccatctc gagccctgcg aacggcgagc tcatgtcact ctcaggcgct   1200
ggcgtgtaca cccttaaggg ctacgcgtac tcaggtggcg ggaggaaggt tacgagggtt   1260
gaggtcagcg ttgacggcgg taagacttgg cttctggcca ccctcgatca tccggaagag   1320
aggcactctc atgctccttc ctatggccgc tactactgct ggtgcttctg ggagtacacc   1380
attgacaagt tcgccctcct caacgcggcc acgtcctctg cgaactctt ggttcgcgct   1440
tgggacgaag ggaacaatac ccaacccgcg aagctcacct ggaacctgat gggcatgggc   1500
aacaactgct acttccgggt cacggtggcc ccgaagcagt cttccggcga gtttgcgctt   1560
gagtttcttc atcccaccgt tgctggccct gcagaaggcg ggtggatgcc tcctcctcaa   1620
gagtctgtgg ttgctgccgc tgctgctgcg ggtgtggctg aaaccctgaa gcgcactaag   1680
gacgcgccgc agatgaacaa gatgaccag caggactcca agacgatcac gatggaggag   1740
gtcgctaagc atgacaccga ggaggactcc tggatcgtgg tgcacaacaa ggtctacgac   1800
tgcactccgt ttctcaagga ccaccctggc ggcggtgcca gcatcgtcat gaatgctggt   1860
gccgactgca cggaggaatt cgacgctatc cacagcacga aggccaagtc gatgctcgac   1920
gactactaca tcggcgagct ggccgttgag gacatagagg atgagcctga gcagccggct   1980
ctccacctct ccaagtcctc tgtgcagctc atgaaggacg acttcaagga gcagtccgtg   2040
cgcaaggctg ttgaaggcgt ggacgaagag gtcgtgactc ctgtggccct gaaccctaag   2100
aagtggattc acttcccgct catccagaag gaggaactgt cccacgatac gaggcgcttc   2160
cggtttggcc tccctacacc tggtcatcgc cttgggctcc cggtgggctt ccatatgttc   2220
ctgatggcga ccatagacgg tgctatggtg atgagggcct acacgccgac ctcctctgat   2280
gcggagctgg gctacttcga tctcgtgatc aaggtctact tcgccaatgt ccacccgcgc   2340
ttcccggacg gcggtaagtt gacgcagtac atggaggaga tgtcgctggg cgacgagatc   2400
agggttaagg gtccgcttgg ccacatcgag taccgctccc gcggcgagat gaccattgat   2460
ggcaagccaa ggaccgtctc tgctctcact ggtctcatgg ccgggtcagg catcactccc   2520
ttctaccaga tcctccaagc cgtcatggct gacccagagg acaagaccga gctctacctg   2580
atctacgcca atcagacgcc cgaggacgtg ctcctgaggt cagagctgga caagatggcc   2640
gccgagcgcg ataacatcca cgtgtggtac acttgtgaca gggcgcctga ggactggaag   2700
tacgacatcg gcttcatgac ggtggacatg atcaaggagc atggtgctcc ggctggccca   2760
gatgttcttg gcctgtcttg cggtccacca cccttcatca gttcgccgc cactccaagc   2820
ctcaccaaga acggctacgc ggaggagaac cagttcctgt tctag             2865
```

<210> SEQ ID NO 17
<211> LENGTH: 954
<212> TYPE: PRT
<213> ORGANISM: Porphyra perforata

<400> SEQUENCE: 17

Met Glu Ala Ala Ser Gly Ala Leu Ser Glu Leu Arg Leu Glu Lys Gly

```
                1               5                   10                  15
        Val Lys Gly Trp Asp Pro Val Lys Val Pro Gly Arg Ser Ser Leu Lys
                        20                  25                  30

Ser Thr Pro Ile Ala Thr Pro Glu Gly Ser Leu Arg Gly Gly Ser Leu
                        35                  40                  45

Tyr Thr Ala Arg Ser Gln His Ala Ala Gly Ala Asn Asp Val Met Ala
                50                  55                  60

Ala Asn Gly Val Ser Ala Ser Ser Thr Ala Ser Gly Leu Ser Phe Ala
        65                  70                  75                  80

Pro Ser Asp Gly Ser Gly Ser Gly Ser Gly Arg Val Gly Trp Thr Glu
                        85                  90                  95

Leu Asn Asp Ala Leu Asn Ala Lys Leu Ala Ser Lys Ser Thr Met Leu
                        100                 105                 110

Asp Lys Gln His Val Ala Asp Glu Val Asp Asp Arg Asp Val Lys Thr
                        115                 120                 125

Pro Asp Asn Trp Ile Pro Arg His Pro Ala Leu Ile Arg Leu Thr Gly
                        130                 135                 140

Lys His Pro Phe Asn Cys Glu Ala Pro Leu Ser Met Leu Val Asp Gln
        145                 150                 155                 160

Gly Phe Ile Thr Pro Pro Ser Leu His Phe Val Arg Asn His Gly Ala
                        165                 170                 175

Ala Pro Gln Leu Ser Phe Asp Asp His Arg Leu Glu Val Thr Gly Leu
                        180                 185                 190

Val Asp Thr Pro Leu Thr Leu Ser Met Ala Asp Ile Leu Ala Met Pro
                        195                 200                 205

Ser Val Thr Ile Pro Val Thr Leu Thr Cys Ala Gly Asn Arg Arg Lys
                        210                 215                 220

Glu Gln Asn Met Thr Lys Gln Thr Ile Gly Phe Ser Trp Gly Ala Ala
        225                 230                 235                 240

Ala Thr Ser Cys Asn Phe Trp Thr Gly Val Arg Val Arg Asp Val Leu
                        245                 250                 255

Gln Lys Ala Gly Ile Gln Met Asp Lys Ala Arg His Val Cys Phe Val
                        260                 265                 270

Gly Cys Asp Asn Leu Pro Gly Gly Lys Tyr Gly Thr Ser Val Asp Leu
                        275                 280                 285

Ala Thr Ala Met Asp Gln Phe Gly Glu Val Met Leu Ala Tyr Glu Gln
                        290                 295                 300

Asn Gly Ile Arg Leu Thr Pro Asp His Gly Ala Pro Leu Arg Val Val
        305                 310                 315                 320

Ile Pro Gly Trp Ile Gly Gly Arg Met Val Lys Trp Val Thr Gly Leu
                        325                 330                 335

Ser Val Thr Ser Glu Glu Ser Gln Glu His Tyr His Phe Phe Asp Asn
                        340                 345                 350

Arg Ile Leu Pro Pro His Val Asp Ala Glu Leu Ala Lys Ser Glu Gly
                        355                 360                 365

Trp Trp Tyr Lys Arg Glu Tyr Leu Phe Asn Gln Leu Asn Ile Asn Ser
                        370                 375                 380

Ala Ile Ser Ser Pro Ala Asn Gly Glu Leu Met Ser Leu Ser Gly Ala
        385                 390                 395                 400

Gly Val Tyr Thr Leu Lys Gly Tyr Ala Tyr Ser Gly Gly Gly Arg Lys
                        405                 410                 415

Val Thr Arg Val Glu Val Ser Val Asp Gly Gly Lys Thr Trp Leu Leu
                        420                 425                 430
```

```
Ala Thr Leu Asp His Pro Glu Glu Arg His Ser His Ala Pro Ser Tyr
            435                 440                 445

Gly Arg Tyr Tyr Cys Trp Cys Phe Trp Glu Tyr Thr Ile Asp Lys Phe
450                 455                 460

Ala Leu Leu Asn Ala Ala Thr Ser Ser Gly Glu Leu Leu Val Arg Ala
465                 470                 475                 480

Trp Asp Glu Gly Asn Asn Thr Gln Pro Ala Lys Leu Thr Trp Asn Leu
            485                 490                 495

Met Gly Met Gly Asn Asn Cys Tyr Phe Arg Val Thr Val Ala Pro Lys
            500                 505                 510

Gln Ser Ser Gly Glu Phe Ala Leu Glu Phe Leu His Pro Thr Val Ala
            515                 520                 525

Gly Pro Ala Glu Gly Gly Trp Met Pro Pro Gln Glu Ser Val Val
530                 535                 540

Ala Ala Ala Ala Ala Gly Val Ala Glu Thr Leu Lys Arg Thr Lys
545                 550                 555                 560

Asp Ala Pro Gln Met Asn Lys Met Asp Gln Gln Asp Ser Lys Thr Ile
            565                 570                 575

Thr Met Glu Glu Val Ala Lys His Asp Thr Glu Glu Asp Ser Trp Ile
            580                 585                 590

Val Val His Asn Lys Val Tyr Asp Cys Thr Pro Phe Leu Lys Asp His
            595                 600                 605

Pro Gly Gly Gly Ala Ser Ile Val Met Asn Ala Gly Ala Asp Cys Thr
610                 615                 620

Glu Glu Phe Asp Ala Ile His Ser Thr Lys Ala Lys Ser Met Leu Asp
625                 630                 635                 640

Asp Tyr Tyr Ile Gly Glu Leu Ala Val Glu Asp Ile Glu Asp Glu Pro
            645                 650                 655

Glu Gln Pro Ala Leu His Leu Ser Lys Ser Ser Val Gln Leu Met Lys
            660                 665                 670

Asp Asp Phe Lys Glu Gln Ser Val Arg Lys Ala Val Glu Gly Val Asp
            675                 680                 685

Glu Glu Val Val Thr Pro Val Ala Leu Asn Pro Lys Lys Trp Ile His
            690                 695                 700

Phe Pro Leu Ile Gln Lys Glu Glu Leu Ser His Asp Thr Arg Arg Phe
705                 710                 715                 720

Arg Phe Gly Leu Pro Thr Pro Gly His Arg Leu Gly Leu Pro Val Gly
            725                 730                 735

Phe His Met Phe Leu Met Ala Thr Ile Asp Gly Ala Met Val Met Arg
            740                 745                 750

Ala Tyr Thr Pro Thr Ser Ser Asp Ala Glu Leu Gly Tyr Phe Asp Leu
            755                 760                 765

Val Ile Lys Val Tyr Phe Ala Asn Val His Pro Arg Phe Pro Asp Gly
            770                 775                 780

Gly Lys Leu Thr Gln Tyr Met Glu Glu Met Ser Leu Gly Asp Glu Ile
785                 790                 795                 800

Arg Val Lys Gly Pro Leu Gly His Ile Glu Tyr Arg Ser Arg Gly Glu
            805                 810                 815

Met Thr Ile Asp Gly Lys Pro Arg Thr Val Ser Ala Leu Thr Gly Leu
            820                 825                 830

Met Ala Gly Ser Gly Ile Thr Pro Phe Tyr Gln Ile Leu Gln Ala Val
            835                 840                 845

Met Ala Asp Pro Glu Asp Lys Thr Glu Leu Tyr Leu Ile Tyr Ala Asn
            850                 855                 860
```

```
Gln Thr Pro Glu Asp Val Leu Leu Arg Ser Glu Leu Asp Lys Met Ala
865                 870                 875                 880

Ala Glu Arg Asp Asn Ile His Val Trp Tyr Thr Cys Asp Arg Ala Pro
                885                 890                 895

Glu Asp Trp Lys Tyr Asp Ile Gly Phe Met Thr Val Asp Met Ile Lys
            900                 905                 910

Glu His Gly Ala Pro Ala Gly Pro Asp Val Leu Gly Leu Ser Cys Gly
        915                 920                 925

Pro Pro Pro Phe Ile Lys Phe Ala Ala Thr Pro Ser Leu Thr Lys Asn
    930                 935                 940

Gly Tyr Ala Glu Glu Asn Gln Phe Leu Phe
945                 950
```